United States Patent
Xu et al.

(10) Patent No.: US 11,911,390 B2
(45) Date of Patent: *Feb. 27, 2024

(54) PDE5 INHIBITOR POWDER FORMULATIONS AND METHODS RELATING THERETO

(71) Applicant: Respira Therapeutics, Inc., Palo Alto, CA (US)

(72) Inventors: Zhen Xu, Albuquerque, NM (US); Hugh Smyth, West Lake Hills, TX (US); Aileen Gibbons, New York, NY (US); Revati Shreeniwas, Palo Alto, CA (US); Pravin Soni, Sunnyvale, CA (US); Dan Deaton, Apex, NC (US); James Hannon, Albuquerque, NM (US); Stephen Lermer, Austin, TX (US); Robert Curtis, Santa Fe, NM (US); Martin J. Donovan, Austin, TX (US)

(73) Assignee: Respira Therapeutics, Inc., Palo Alto, CA (US)

(*) Notice: Subject to any disclaimer, the term of this patent is extended or adjusted under 35 U.S.C. 154(b) by 24 days.

This patent is subject to a terminal disclaimer.

(21) Appl. No.: 17/211,071

(22) Filed: Mar. 24, 2021

(65) Prior Publication Data

US 2022/0016126 A1    Jan. 20, 2022

Related U.S. Application Data

(63) Continuation of application No. 15/102,957, filed as application No. PCT/US2014/069392 on Dec. 9, 2014, now abandoned.

(60) Provisional application No. 61/913,744, filed on Dec. 9, 2013, provisional application No. 61/913,734, filed on Dec. 9, 2013.

(51) Int. Cl.
| | |
|---|---|
| *A61K 31/53* | (2006.01) |
| *A61K 9/00* | (2006.01) |
| *A61K 31/166* | (2006.01) |
| *A61K 31/4985* | (2006.01) |
| *A61K 31/506* | (2006.01) |
| *A61K 31/519* | (2006.01) |
| *A61K 47/26* | (2006.01) |
| *A61M 15/00* | (2006.01) |

(52) U.S. Cl.
CPC ............ *A61K 31/53* (2013.01); *A61K 9/0075* (2013.01); *A61K 31/166* (2013.01); *A61K 31/4985* (2013.01); *A61K 31/506* (2013.01); *A61K 31/519* (2013.01); *A61K 47/26* (2013.01); *A61M 15/0008* (2014.02); *A61M 2202/064* (2013.01)

(58) Field of Classification Search
CPC ...... A61K 31/53; A61K 9/0075; A61K 47/26; A61K 31/4985; A61K 31/506; A61K 31/519; A61K 31/166; A61M 15/0008; A61M 2202/064
See application file for complete search history.

(56) References Cited

U.S. PATENT DOCUMENTS

| | | | |
|---|---|---|---|
| 8,758,824 B2 * | 6/2014 | Lipp | A61K 31/56 424/680 |
| 2007/0031349 A1 * | 2/2007 | Monteith | A61K 31/4985 424/440 |

FOREIGN PATENT DOCUMENTS

WO    WO 2011/030351    *    3/2011

OTHER PUBLICATIONS

Xian-Ming et al. (J. Pharm Sci. 90(9) (2001); 1424-1434.*
Xian-Ming et al. (International J. Pharmaceuticals 176 (1); (1998) 99-110.*

* cited by examiner

*Primary Examiner* — Shirley V Gembeh
(74) *Attorney, Agent, or Firm* — Jon E. Gordon; Haug Partners LLP

(57) ABSTRACT

Novel dry powder compositions comprising and methods relating thereto are provided. The dry powder compositions comprise PDE5 inhibitors, such as vardenafil, or pharmaceutically acceptable salts or esters thereof. The dry powder compositions may optionally include an carrier/excipient. The concentration of active agent may be at least about 2% by weight. Methods of aerosolizing the dry powder compositions and using them to treat various diseases are also disclosed.

11 Claims, 25 Drawing Sheets

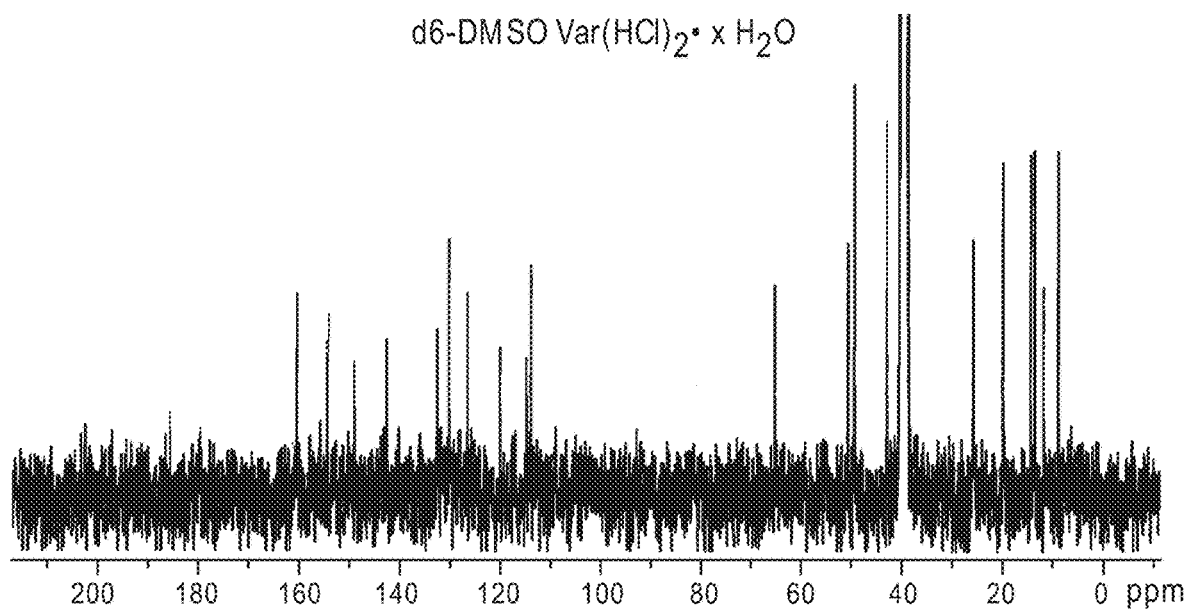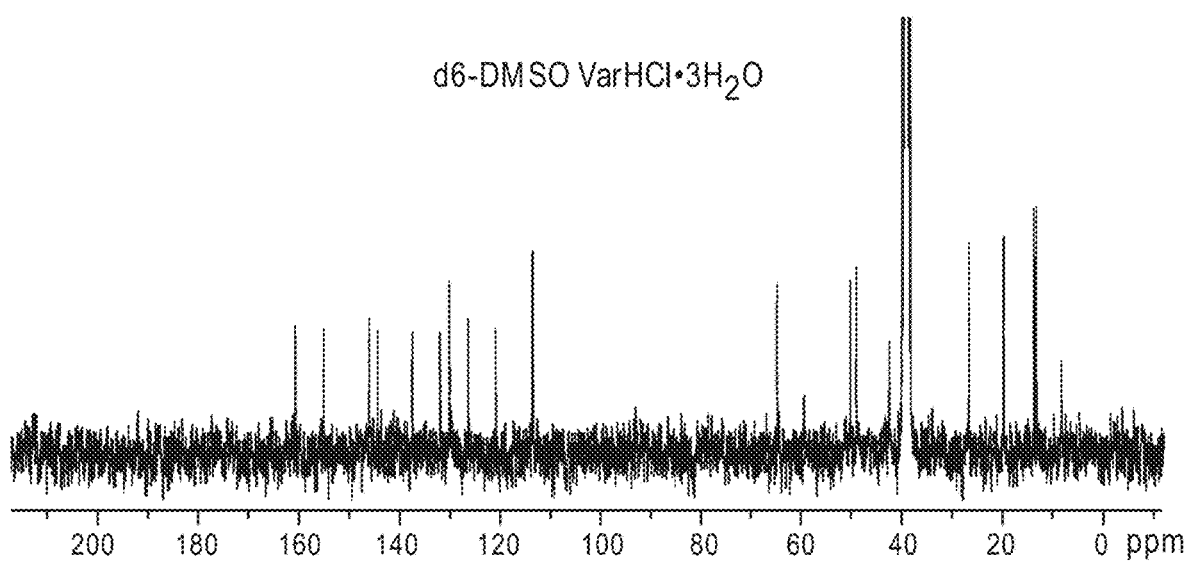
FIG. 2

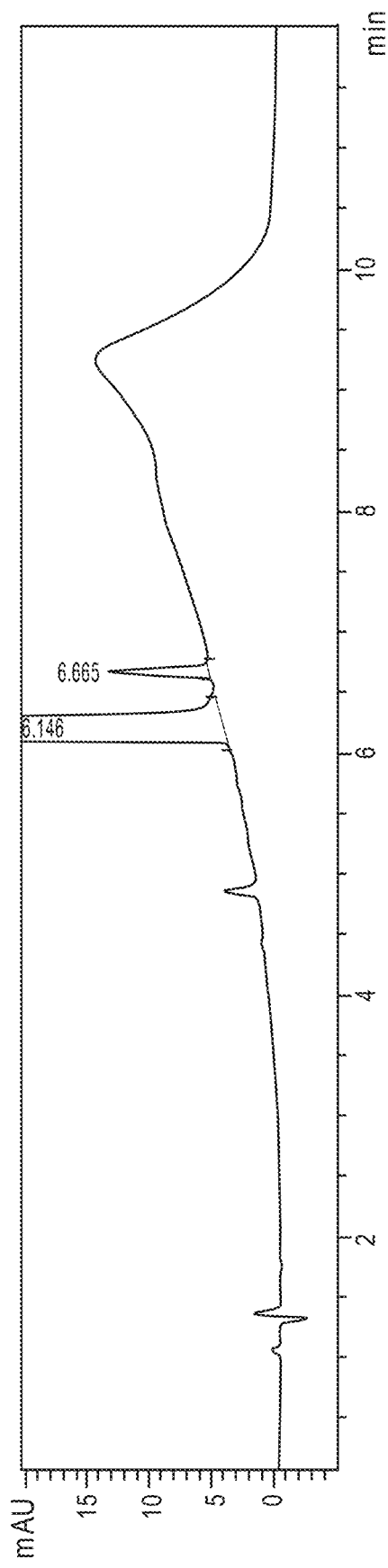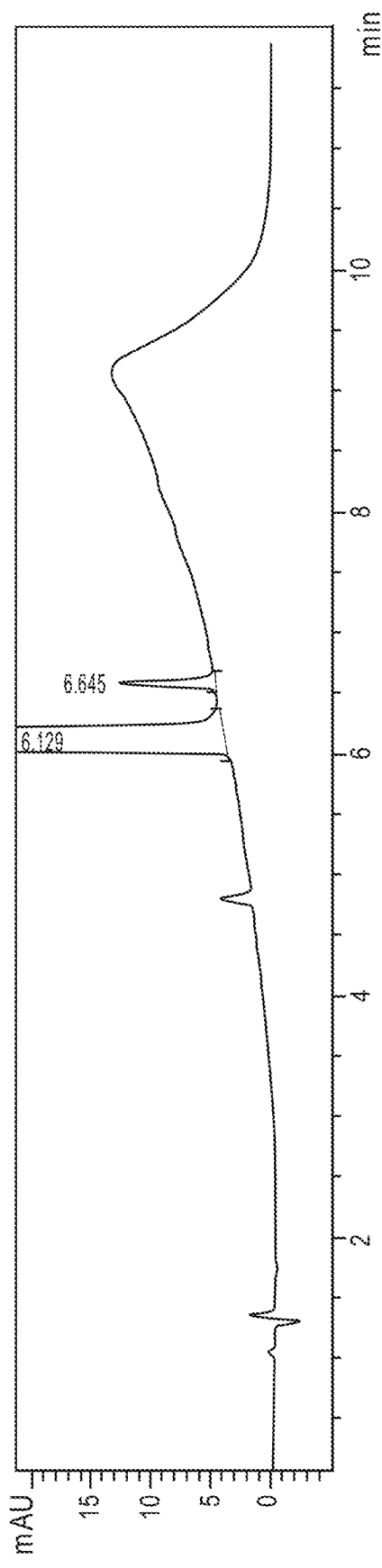

1300

1301 — PROVIDING A POWDER PHARMACEUTICAL COMPOSITION COMPRISING AT LEAST 2 % BY WEIGHT OF A PDE5 INHIBITOR OR A PHARMACEUTICALLY ACCEPTABLE SALT OR ESTER AN A PHARMACEUTICALLY ACCEPTABLE CARRIER

1302 — PROVIDING AN INHALER COMPRISING A DISPERSION CHAMBER HAVING AN INLET AND AN OUTLET, THE DISPERSION CHAMBER CONTAINING AN ACTUATOR THAT IS MOVABLE RECIPROCATABLE ALONG A LONGITUDINAL AXIS OF THE DISPERSION CHAMBER

1303 — INDUCING AIR FLOW THROUGH THE OUTLET CHANNEL TO CAUSE AIR AND THE POWDER PHARMACEUTICAL COMPOSITION TO ENTER INTO THE DISPERSION CHAMBER FROM THE INLET, AND TO CAUSE THE ACTUATOR TO OSCILLATE WITHIN THE DISPERSION CHAMBER TO ASSIST IN DISPERSING THE POWDER PHARMACEUTICAL COMPOSITION FROM THE OUTLET FOR DELIVERY TO A SUBJECT THROUGH THE OUTLET

FIG. 13

PDE5 INHIBITOR POWDER FORMULATIONS AND METHODS RELATING THERETO

CROSS-REFERENCE TO RELATED APPLICATIONS

The present application is a continuation of U.S. application Ser. No. 15/102,957, filed Jun. 9, 2016, which is a 371 national stage application of International Application No. PCT/US2014/069392, filed Dec. 9, 2014, which claims the benefit of U.S. Provisional Application No. 61/913,734, filed Dec. 9, 2013, and U.S. Provisional Application No. 61/913,744, filed Dec. 9, 2013, which applications are hereby incorporated by reference in their entireties.

FIELD

The invention relates to powder formulations of PDE5 inhibitors and methods relating thereto.

BACKGROUND

Phosphodiesterase type 5 inhibitors (PDE5 inhibitors) block the degradative action of cGMP-specific phosphodiesterase type 5 (PDE5) on cyclic GMP in the smooth muscle cells lining the blood vessels supplying the corpus cavernosum of the penis. These drugs, including vardenafil (Levitra™), sildenafil (Viagra™), and tadalafil (Cialis™), are administered orally for the treatment of erectile dysfunction and were the first effective oral treatment available for the condition.

PDE5 inhibitors have also been studied for other clinical use as well, including cardiovascular and heart diseases. For example, because PDE5 is also present in the arterial wall smooth muscle within the lungs, PDE5 inhibitors have also been explored for lung diseases such as pulmonary hypertension and cystic fibrosis. Pulmonary arterial hypertension, a disease characterized by sustained elevations of pulmonary artery pressure, which leads to an increased incidence of failure of the right ventricle of the heart, which in turn can result in the blood vessels in the lungs become overloaded with fluid. Two oral PDE5 inhibitors, sildenafil (Revatio™) and tadalafil (Adcirca™), are approved for the treatment of pulmonary arterial hypertension. PDE5 inhibitors have been found to have activity as both a corrector and potentiator of CFTR protein abnormalities in animal models of cystic fibrosis disease. (Lubamba et al., Am. J. Respir. Crit. Care Med. (2008) 177:506-515, Lubamba et al., J. Cystic Fibrosis (2012) 11:266-273). Sildenafil has also been studied as a potential anti-inflammatory treatment for cystic fibrosis. Oral PDE5 inhibitors have also been reported to have anti-remodeling properties and to improve cardiac inotropism, independent of afterload changes, with a good safety profile. (Giannetta et al., BMC Medicine (2014) 12:185). However, oral administration of PDE5 inhibitors results in poor and variable bioavailability and also extensive metabolism in the liver. (Sandqvist et al., Eur. J. Clin. Pharmacol. (2013) 69:197-207; Mehrotra, Intl. J. Impotence Res. (2007) 19:253-264.) If oral doses are increased beyond certain levels, the incidence of systemic side effects increase which prevents the acceptable use of these drugs. (Levitra EMEA Scientific Discussion Document, 2005)

In view of the limitations presented by oral administration formulations of PDE5 inhibitors, there is a continuing need for further improvement in pharmaceutical preparations that deliver increased drug doses to the lung.

BRIEF SUMMARY

In one aspect, provided is a powder pharmaceutical composition comprising a) at least about 2% by weight of a PDE5 inhibitor or a pharmaceutically acceptable salt or ester thereof relative to the total weight of the overall pharmaceutical composition, and b) at least one pharmaceutically acceptable carrier.

In another aspect, provided is a method of aerosolizing a powder pharmaceutical composition comprising a) at least 2% by weight of a PDE5 inhibitor, or a pharmaceutically acceptable salt or ester thereof, relative to the total weight of the overall pharmaceutical composition, and b) at least one pharmaceutically acceptable carrier, the method comprising: providing an inhaler comprising a dispersion chamber having an inlet and an outlet, the dispersion chamber containing an actuator that is movable reciprocatable along a longitudinal axis of the dispersion chamber; and inducing air flow through the outlet channel to cause air and the powder pharmaceutical composition to enter into the dispersion chamber from the inlet, and to cause the actuator to oscillate within the dispersion chamber to assist in dispersing the powder pharmaceutical composition from the outlet for delivery to a subject through the outlet.

In another aspect, provided is a method of treating a disease in a subject in need thereof, the method comprising administering to the subject via a pulmonary route an effective amount of a powder pharmaceutical composition comprising a) at least about 2% of a PDE5 inhibitor, or a pharmaceutically acceptable salt or ester thereof, by weight relative to the total weight of the overall pharmaceutical composition dose, and b) at least one pharmaceutically acceptable carrier.

It will be appreciated from a review of the remainder of this application that further methods and compositions are also part of the invention.

BRIEF DESCRIPTION OF THE DRAWINGS

FIG. 2 illustrates a $^{13}$C NMR spectrometry spectrum for Var(HCl)$_2$·xH$_2$O (top) and VarHCl·3H$_2$O (bottom) according to certain aspects.

FIG. 4A shows a HPLC trace for VarHCl·3H$_2$O as obtained from the manufacturer.

FIG. 4B and FIG. 4C show HPLC traces for VarHCl·3H$_2$O following acid degradation in 1N HCl at r.t. for 48 hr and in 1N HCl at 60° C. for 4 hr, respectively. FIG. 4D and FIG. 4E show HPLC traces for VarHCl·3H$_2$O following basic degradation in 1N NaOH at r.t. for 48 hr and in 1N NaOH at 60° C. for 4 hr, respectively. FIG. 4F shows an HPLC trace for VarHCl·3H$_2$O following oxidative degradation in 6% H$_2$O$_2$ at r.t. for 48 hr.

FIGS. 5A-5D illustrate the results of VarHCl·3H$_2$O-lactose (1:1) formulation blend stability at different temperatures and humidities as assessed by HPLC according to some aspects. FIG. 5A shows a HPLC trace of the formulation stored pouched at 25° C. and 60% relative humidity (RH). FIG. 5B shows a HPLC trace of the formulation stored pouched at 40° C. and 75% RH. FIG. 5C shows a HPLC trace of the formulation stored open to ambient environment at 40° C. and 75% RH. FIG. 5D shows a HPLC trace of the formulation prior to storage (control).

FIG. 8A shows the DSC thermogram for Var(HCl)$_2$·xH$_2$O. FIG. 8B shows the DSC thermogram for VarBase. FIG. 8C shows the DSC thermogram for VarHCl·xH$_2$O.

FIGS. 9A and 9B show the DVS isotherm plot for micronized Var(HCl)$_2$·xH$_2$O and micronized VarBase, respectively. DVS isotherm plots for micronized VarHCl·xH$_2$O are shown in FIG. 9C and FIG. 9D, with the Y axis reflecting either percent change in mass or the stoichiometric water sorption and desorption profiles (ratio of H$_2$O vapor absorbed to dry VarHCl (mol/mol)).

FIGS. 11A, 11B, and 11C show the diffractograms for micronized Var(HCl)$_2$·xH$_2$O, micronized VarBase, and micronized VarHCl·xH$_2$O, respectively.

FIG. 13 is a block diagram of a method of aerosolizing a pow

Figure 1:
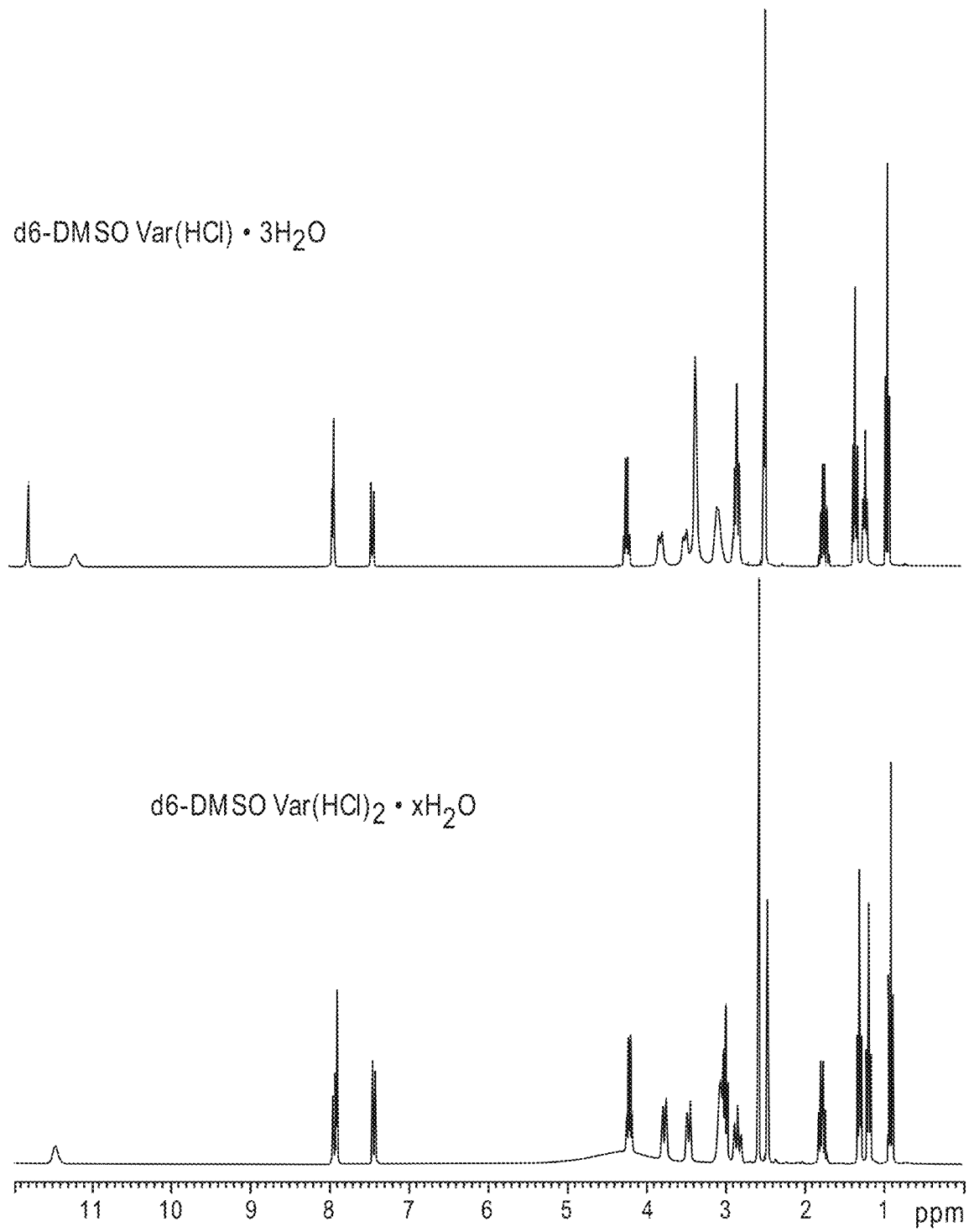
FIG. 1 illustrates a $^1$H NMR spectrometry spectrum for VarHCl·3H$_2$O (top) and Var(HCl)$_2$·xH$_2$O (bottom) according to certain aspects.

As used herein, "subject" refers to a mammal that may benefit from the administration of a drug composition or method of this invention. Examples of subjects include humans, and may also include other animals such as horses, pigs, cattle, dogs, cats, rabbits, rats, mice and aquatic mammals. In one specific aspect, a subject is a human.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, "pharmaceutically acceptable carrier," "carrier," and "excipient" may be used interchangeably, and refer to any inert and pharmaceutically acceptable material that has substantially no biological activity, and makes up a substantial part of the formulation.

As used herein, the terms "administration," and "administering" refer to the manner in which an active agent is presented to a subject. Administration can be accomplished by various art-known routes such as oral, parenteral, transdermal, inhalation, implantation, etc.

The term "pulmonary administration" represents any method of administration in which an active agent can be administered through the pulmonary route by inhaling an aerosolized liquid or powder form (nasally or orally). Such aerosolized liquid or powder forms are traditionally intended to substantially release and or deliver the active agent to the mucosal membrane and epithelium of the lungs. In the context of this disclosure, the active agent is in powder form.

The term "nominal load" or "total load" refers to the total amount of formulation packaged or partitioned for administration to a subject. For example, the nominal load is the total amount of powder formulation that is enclosed in a capsule for use with an inhaler.

The term "nominal dose" or "total dose" refers to the total amount or mass of active agent packaged or partitioned for administration to a subject. For example, the nominal dose is the total amount of active agent that is enclosed in a capsule for use with an inhaler.

The term "emitted dose" (ED(%)) refers to the mass of an active agent that is emitted from a dry powder inhaler aerosolization device as a percentage of a nominal dose mass.

Powder that exhibits high flow rate often results in higher ED(%).

The term "fine particle fraction" or "fine particle fraction from the emitted dose" (% FPF(ED)) refers to the mass of active agent having an aerodynamic diameter below about 5 µm as a percentage of an emitted dose mass. Typically, the cutoff size is less than or equal to an aerodynamic diameter of about 5 µm but, depending on the experimental conditions, can be around 6.4 µm. The FPF is often used to evaluate the efficiency of aerosol deaggregation.

The term "respirable fraction" (RF(%)) is the mass of an active agent that is below a certain aerodynamic cutoff size as a percentage of a nominal dose mass. Also known as the fine particle fraction from the total dose (FPF(TD)). Fine particle fraction may also be calculated as a percentage of the emitted dose (FPF(ED)). The respirable fraction represents the proportion of powder aerosol that can enter the deep respiratory tract. Typically, the RF cutoff size is an aerodynamic diameter of less than about 10 µm, preferably less than about 7 µm, and most preferably less than or about 5 µm. For example, depending on the experimental conditions, the cutoff size RF can be around 6.4 µm. The respirable fraction may be determined using an inertial sampling device.

The aerodynamic diameter ($D_{ae}$) is a spherical equivalent diameter and derives from the equivalence between the inhaled particle and a sphere of unit density ($\rho_o$) undergoing sedimentation at the same rate as per the following formula:

$$D_{ae} = D_v \sqrt{\left(\frac{\rho}{\chi \rho o}\right)} \quad \text{(Eq. 1)}$$

where $D_v$ is the volume-equivalent diameter, $\rho$ is the particle density and $\chi$ is the shape factor. Hence, the aerodynamic behavior depends on particle geometry, density and volume diameter: a small spherical particle with a high density will behave aerodynamically as a bigger particle, being poorly transported in the lower airways. The $D_{ae}$ can be improved reducing the volume diameter and the density or increasing the shape factor of the particles, by means of different processes.

The term "mass median aerodynamic diameter" (MMAD) refers to the mass median aerodynamic diameter of airborne particles at which 50% of particles by mass are larger and 50% are smaller. In other words, it is the median of the aerodynamic particle size distribution as a function of particle mass. The percentages of mass less than the stated aerodynamic diameters versus the aerodynamic diameters are plotted logarithmically. The MMAD is taken as the intersection of the line with the 50% cumulative percent. Computational methods can also be applied.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

II. Formulations

Provided are dry powder pharmaceutical compositions of PDE5 inhibitors and pharmaceutically acceptable salts and esters thereof. The compositions include at least about 2% by weight of active agent and at least one pharmaceutically acceptable carrier.

In one aspect, provided is a powder pharmaceutical composition comprising a) at least about 2% by weight of a PDE5 inhibitor or a pharmaceutically acceptable salt or ester thereof relative to the total weight of the overall pharmaceutical composition, and b) at least one pharmaceutically acceptable carrier. In one aspect, the PDE5 inhibitor may be at least one of vardenafil, sildenafil, tadalafil, avanafil, benzamidenafil, lodenafil, mirodenafil, udenafil, or zaprinast, or a pharmaceutically acceptable salt or ester thereof. In one aspect, the composition may include at least about 2% to about 20% by weight of the PDE5 inhibitor. In one aspect, the composition may include at least about 2% to about 20% by weight of vardenafil or a pharmaceutically acceptable salt or ester thereof. In one aspect, the at least one pharmaceutically acceptable carrier may include lactose, mannitol, trehalose, or starch. In one aspect, the at least one pharmaceutically acceptable carrier may include at least one of a mono-, di- or poly-saccharide, or their derivatives, calcium stearate, magnesium stearate, leucine or its derivatives, lecithin, human serum albumin, polylysine, polyarginine, or other force control agents, or combinations thereof. In one aspect, the PDE5 inhibitor or a pharmaceutically acceptable salt or ester may be micronized. In one aspect, the composition may be packaged to have a nominal load of about 3 mg to 30 mg. In one aspect, the composition may be packaged to have a nominal dose of at least about 0.25 mg. In one aspect, the composition may be packaged to have a delivered dose of at least about 0.075 mg.

In one aspect, provided is a method of aerosolizing a powder pharmaceutical composition comprising a) at least 2% by weight of a PDE5 inhibitor, or a pharmaceutically acceptable salt or ester thereof, relative to the total weight of the overall pharmaceutical composition, and b) at least one pharmaceutically acceptable carrier, the method comprising: providing an inhaler comprising a dispersion chamber having an inlet and an outlet, the dispersion chamber containing an actuator that is movable reciprocatable along a longitudinal axis of the dispersion chamber; and inducing air flow through the outlet channel to cause air and the powder pharmaceutical composition to enter into the dispersion chamber from the inlet, and to cause the actuator to oscillate within the dispersion chamber to assist in dispersing the powder pharmaceutical composition from the outlet for delivery to a subject through the outlet. In various aspects, the powder pharmaceutical composition may have one or more of the properties recited in the previous paragraph. In one aspect, the composition may have a mass median aerodynamic diameter of between 0.5 μm and 5 μm upon aerosolization. In one aspect, the composition may have a fine particle fraction of at least about 20% upon aerosolization. In one aspect, the composition may have an emitted dose of at least about 40% upon aerosolization. In one aspect, the powdered medicament may be stored within a storage compartment (of the inhaler), and wherein the powder pharmaceutical composition is transferred from the storage compartment, through the inlet and into the dispersion chamber. In one aspect, the inlet may be in fluid communication with an initial chamber, and wherein the powder pharmaceutical composition is received into the initial chamber prior to passing through the inlet and into the dispersion chamber.

In one aspect, provided is a method of treating a disease in a subject in need thereof, the method comprising administering to the subject via a pulmonary route an effective amount of a powder pharmaceutical composition comprising a) at least about 2% of a PDE5 inhibitor, or a pharmaceutically acceptable salt or ester thereof, by weight relative to the total weight of the overall pharmaceutical composition dose, and b) at least one pharmaceutically acceptable carrier. In one aspect, the disease may be a lung disease or a heart disease. For example, in some aspects, the lung disease may be pulmonary arterial hypertension or cystic fibrosis. In other aspects, the heart disease may be congestive heart failure. In various aspects, the powder pharmaceutical composition may have one or more of the properties recited in the previous paragraphs. In one aspect, the powder pharmaceutical composition may be administered as an aerosol. In another aspect, the powder pharmaceutical composition may be administered using a dry powder inhaler or a metered dose inhaler. For example, in some aspects, the powder pharmaceutical composition may be administered by providing an inhaler comprising a dispersion chamber having an inlet and an outlet, the dispersion chamber containing an actuator that is movable reciprocatable along a longitudinal axis of the dispersion chamber; and inducing air flow through the outlet channel to cause air and the powder pharmaceutical composition to enter into the dispersion chamber from the inlet, and to cause the actuator to oscillate within the dispersion chamber to assist in dispersing the powder pharmaceutical composition from the outlet for delivery to a subject through the outlet. In one aspect, a delivered dose of about 0.25 mg to about 20 mg may be delivered to the subject upon aerosolization.

Active Agents

In one aspect, the active agent of the pharmaceutical composition may a PDE5 inhibitor. Examples of PDE5 inhibitors include, but are not limited to, vardenafil, sildenafil, tadalafil, avanafil, benzamidenafil, lodenafil, mirodenafil, udenafil, zaprinast, or any of their pharmaceutically acceptable salts, esters, or derivatives. In one aspect, the active agent may be vardenafil, in all of its suitable forms, which has the formula (I):

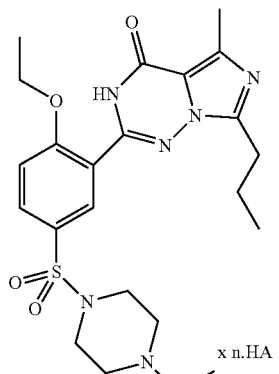

n = 1 or 2
HA = acid

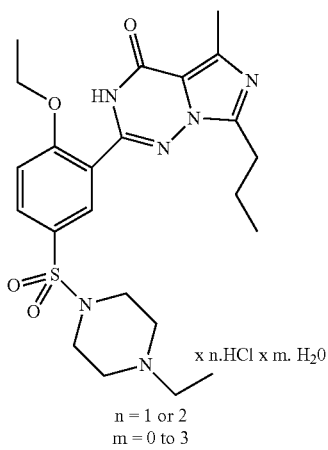

n = 1 or 2
m = 0 to 3

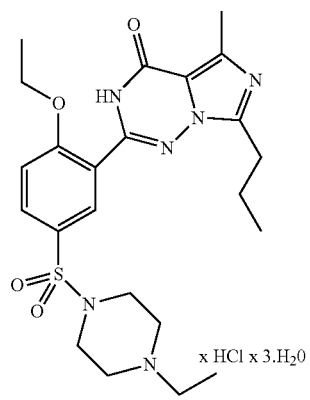

The compound of Formula (I) is chemically identified as 2-[2-ethoxy-5-(4-ethylpiperazin-1-yl)sulfonylphenyl]-5-methyl-7-propyl-1H-imidazo[5,1-i][1,2,4]triazin-4-one. Two polymorphic structures have been known for the free base of vardenafil described by Formula (I) (Form I described in WO/1999/024433 and Form II described in U.S. Pat. No. 7,977,478). Vardenafil can further form salts, which are described by general chemical Formula (II), wherein HA stands for any acid (as described in WO/2013/075680). The majority of solid forms of vardenafil are the respective hydrochlorides and their hydrates (as described in U.S. Pat. Nos. 6,362,178 and 7,977,478; Haning et al., Bioorg. Med. Chem. Lett. 12 (2002) 865-868), which are described by general Formula (III). The hydrochloride trihydrate (as described in U.S. Pat. Nos. 6,362,178 and 8,273,876, WO/2002/050076) described by chemical Formula (IV), is the form of vardenafil that has been used for preparing oral dosage forms (WO/2010/130393, WO/2008/151811, WO/2005/110420, WO/2004/006894). An amorphous form of vardenafil hydrochloride trihydrate has been described (U.S. Pat. No. 7,977,478), as well as a thermodynamically stable crystalline form used in preparing dosage forms (U.S. Pat. No. 8,273,876). The crystalline hydrate according to Formula (IV) is instable due to possible loss of crystal water in using this salt for preparation of a dosage form (U.S. Pat. No. 8,273,876), but also in any inappropriate manipulation with this salt during its preparation.

For example, the active agent may be vardenafil as shown in Formula (I) (also referred to herein as VarBase), sildenafil, tadalafil, avanafil, benzamidenafil, lodenafil, mirodenafil, udenafil, or zaprinast, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, solvates, including hydrates, polymorphs, pseudopolymorphs, esters, etc. In some instances, the term "active agent" includes all pharmaceutically acceptable forms of vardenafil or the other PDE5 inhibitors described herein. For example, the active agent can be in an isomeric mixture. In addition, the active agent can be in a solvated form such as a hydrate. Any form of the active agent is suitable for use in the compositions of the present invention, such as, for example, a pharmaceutically acceptable salt of the active agent, a free acid of the active agent, or a mixture thereof. In some instances, the term "active agent" may include all pharmaceutically acceptable salts, derivatives, esters, and analogs of vardenafil or the other PDE5 inhibitors listed herein, as well as combinations thereof.

In some aspects, the active agent may be a vardenafil compound having the chemical forms as set forth in Formulas (I), (II), (III), or (IV) above. For example, the pharmaceutically acceptable salts of vardenafil may include, without limitation, hydrogen chloride salt forms thereof and the like. For example, where the vardenafil salt (VarSalt) is hydrogen chloride, the mono-hydrogen chloride may be represented by Formulas (II) or (IV). When unhydrated, the mono-hydrogen chloride form may be represented by Formula (II), also referred to herein as VarHCl. When this form in fully hydrated, it is represented by Formula (IV), also referred to herein as VarHCl·3H$_2$O. When partially hydrated, it is represented by Formula (III), also referred to herein as VarHCl·xH$_2$O, where "x" represents undetermined amount of bound water between 0-3. The di-hydrogen chloride form of vardenafil can be represented by Formulas (II) or (III). When unhydrated, the di-hydrogen chloride form may be represented by Formula (II), also referred to herein as Var(HCl)$_2$. When hydrated, this form is represented by Formula (III), which is referred to herein as Var(HCl)$_2$·xH$_2$O, as this form is unstable and readily loses water molecules.

In certain aspects, active agent may be present in different crystal forms. The different crystalline forms of the same compound can have an impact on one or more physical properties, such as stability, solubility, melting point, bulk density, flow properties, bioavailability, etc. For example, vardenafil base as shown in Formula (I) has two polymorphic forms.

The solid powder forms of active agent may be characterized by one or more of several techniques including differential scanning calorimetry (DSC), thermogravimetric analysis (TGA), dynamic vapor sorption (DVS), x-ray powder diffraction (XRPD), and Karl Fischer (KF) titration, and pH titration. The active agents may also be assessed in liquid form by nuclear magnetic resonance (NMR). Further, combinations of such techniques may be used to describe the invention. For example, one or more XRPD patterns combined with one or more DVS plots may be used to describe one or more solid forms of the active agents in a way that differentiates them from each other, including the various forms of different PDE5 inhibitors (such as salts, esters, and hydrates).

Although it characterizes a form, it is not necessary to rely only upon an entire diffraction pattern or spectrum to characterize an active agent. Those of ordinary skill in the pharmaceutical arts recognize that a subset of a diffraction pattern, spectrum, or plot may be used to characterize an active agent provided that subset distinguishes the active agent from the other forms. Thus, one or more X-ray powder diffraction pattern alone may be used to characterize an active agent. Likewise, one or more DVS or DSC plots alone may be used to characterize an active agent. Likewise, one or more pH titration analyses may be used to characterize an active agent. Likewise, one or more NMR spectra alone may be used to characterize an active agent. Such characterizations are done by comparing the XRPD, DSC, DVS, TGA, NMR data amongst the forms to determine characteristic peaks.

One may also combine data from other techniques in such a characterization. Thus, one may rely upon one or more XRPD pattern and, for example, one or more NMR spectrum, HPLC trace, DSC and/or DVS plot, TGA data, Karl Fischer analyses, or pH analyses, to characterize an active agent. For example, if one or more X-ray diffraction peak characterizes an active agent, one could also consider HPLC, DSC, DVS, TGA, NMR, KF titration, and pH titration data to characterize the active agent. In particular, combining multiple techniques for analysis of an active agent forms can be advantageous to confirm chemical identity of the active agent.

For example, as shown in Table 2, HPLC analysis combined with Karl Fischer titration can identify the chemical forms of vardenafil as Var(HCl)$_2$·xH$_2$O and not VarHCl·xH$_2$O. In some instances, elemental analysis of carbon, hydrogen, and nitrogen can identify different chemical forms of vardenafil based on their molecular formulas. For example, for VarBase and vardenafil HCl salts (VarSalts) and hydrates, the following equations may be used:

$$\text{Water equation: } \frac{18y}{488.6 + 36.5y + 18x} \quad \text{(Eq. 2)}$$

$$\text{CHN equation: } \frac{488.6 - 64 - 32 - x + 2y}{488.6 + 36.5y + 18x} \quad \text{(Eq. 3)}$$

where y is the number of HCl molecules bound to the vardenafil molecule and x is the number of water molecules bound to the vardenafil molecule. For other salts, the equations may be modified to account for the elements of the salt. In another example, NMR analysis may be performed to identify chemical shifts characteristic of different vardenafil forms. The NMR analysis may be either $^1$H NMR analysis or $^{13}$C NMR analysis as shown in FIG. 1 and FIG. 2. In some instances, d$_6$-DMSO can be used as a solvent. For example, by $^1$H NMR analysis, VarHCl.3H$_2$O can be identified by a methyl peak shifted to 2.472 ppm and triplet (doublet+singlet) around 8 ppm as shown in FIG. 1. In another example, by $^1$H NMR analysis, Var(HCl)$_2$·xH$_2$O can be identified by a methyl peak shifted to 2.604 ppm and a quintet (triplet+doublet) around 8 ppm as shown in FIG. 1.

Figure 8A:
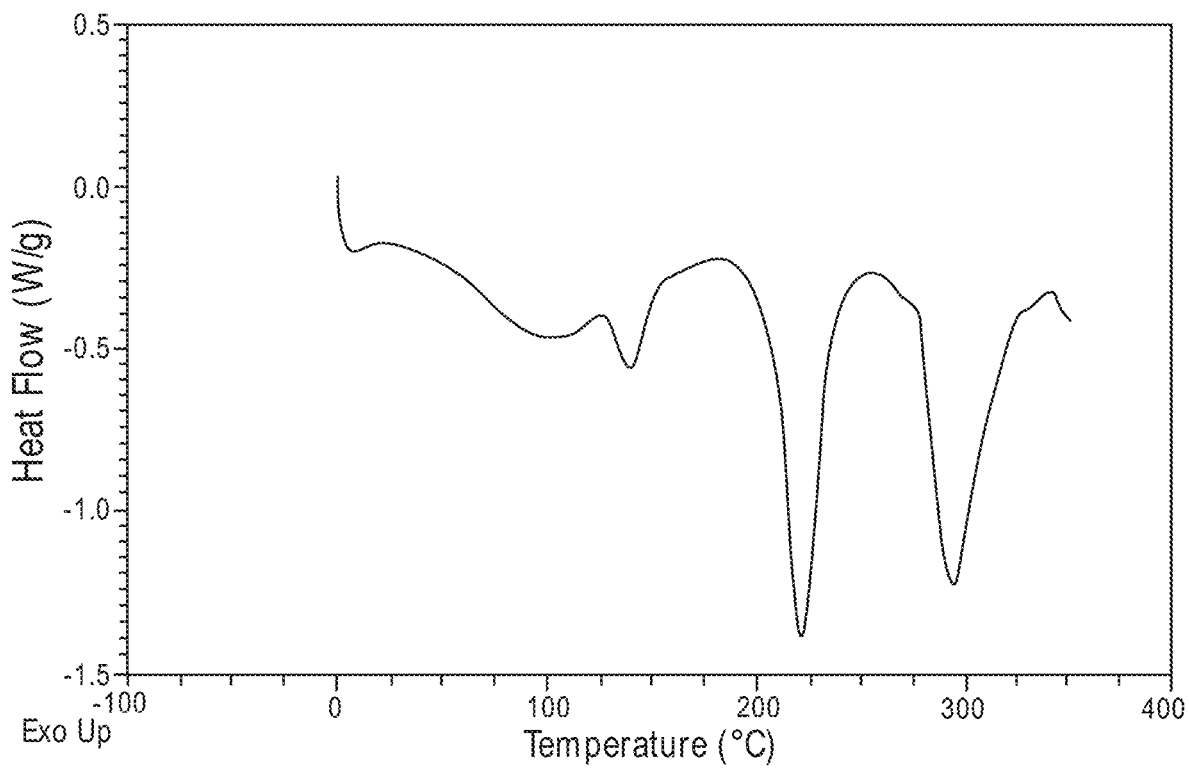
FIGS. 8A-8C illustrate the results of differential scanning calorimetry (DSC) analysis to assess the thermal properties of micronized vardenafil compounds according to certain aspects.
Figure 8B:
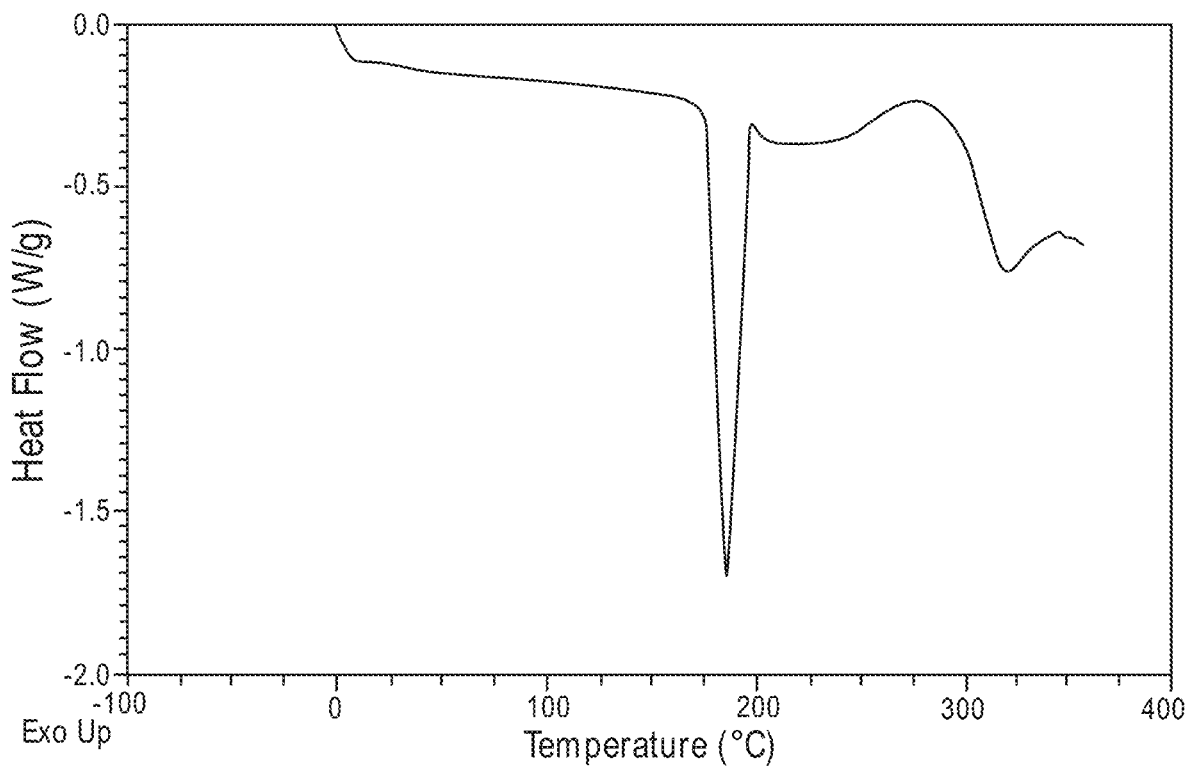
Figure 8C:
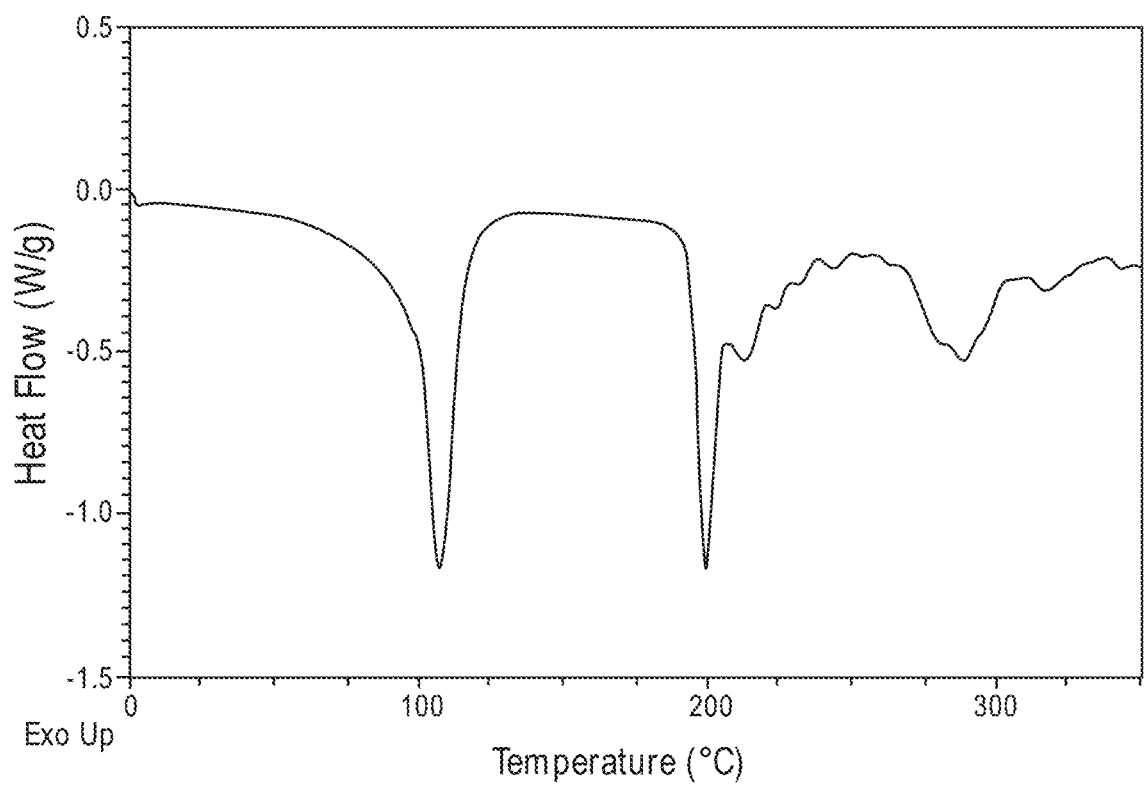
Figure 10:
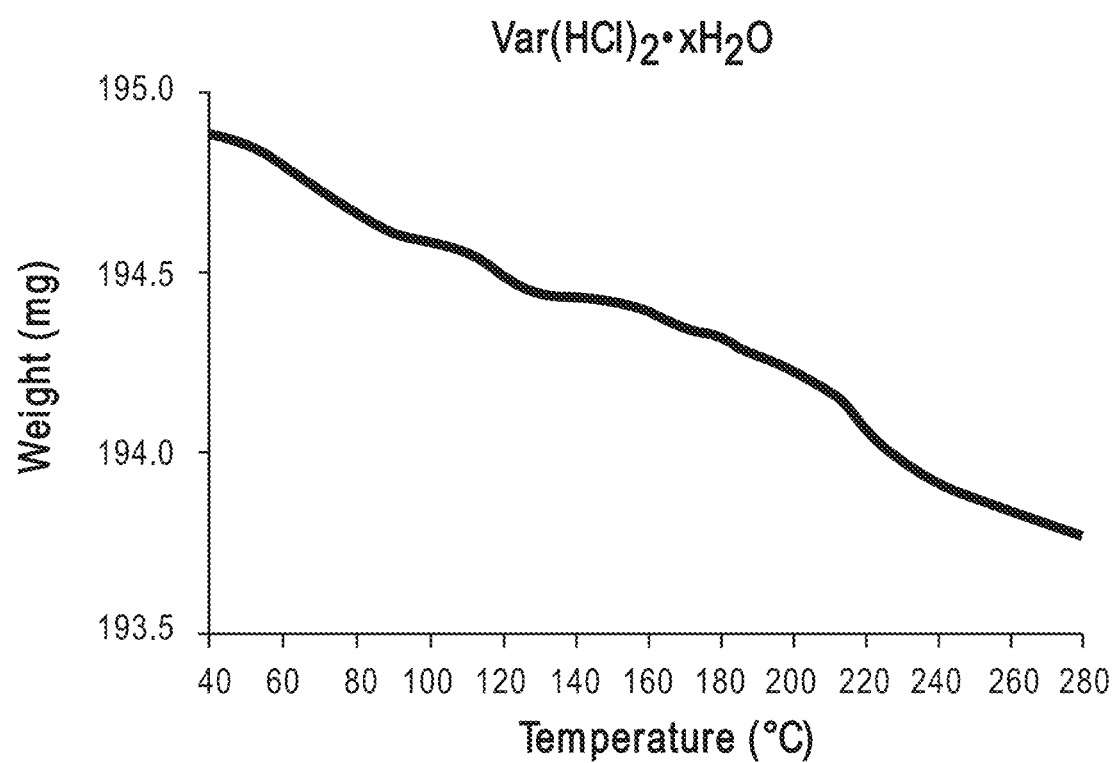
FIG. 10 illustrates thermogravimetric analysis (TGA) of micronized Var(HCl)$_2$·xH$_2$O to assess mass loss according to certain aspects.
Figure 11A:
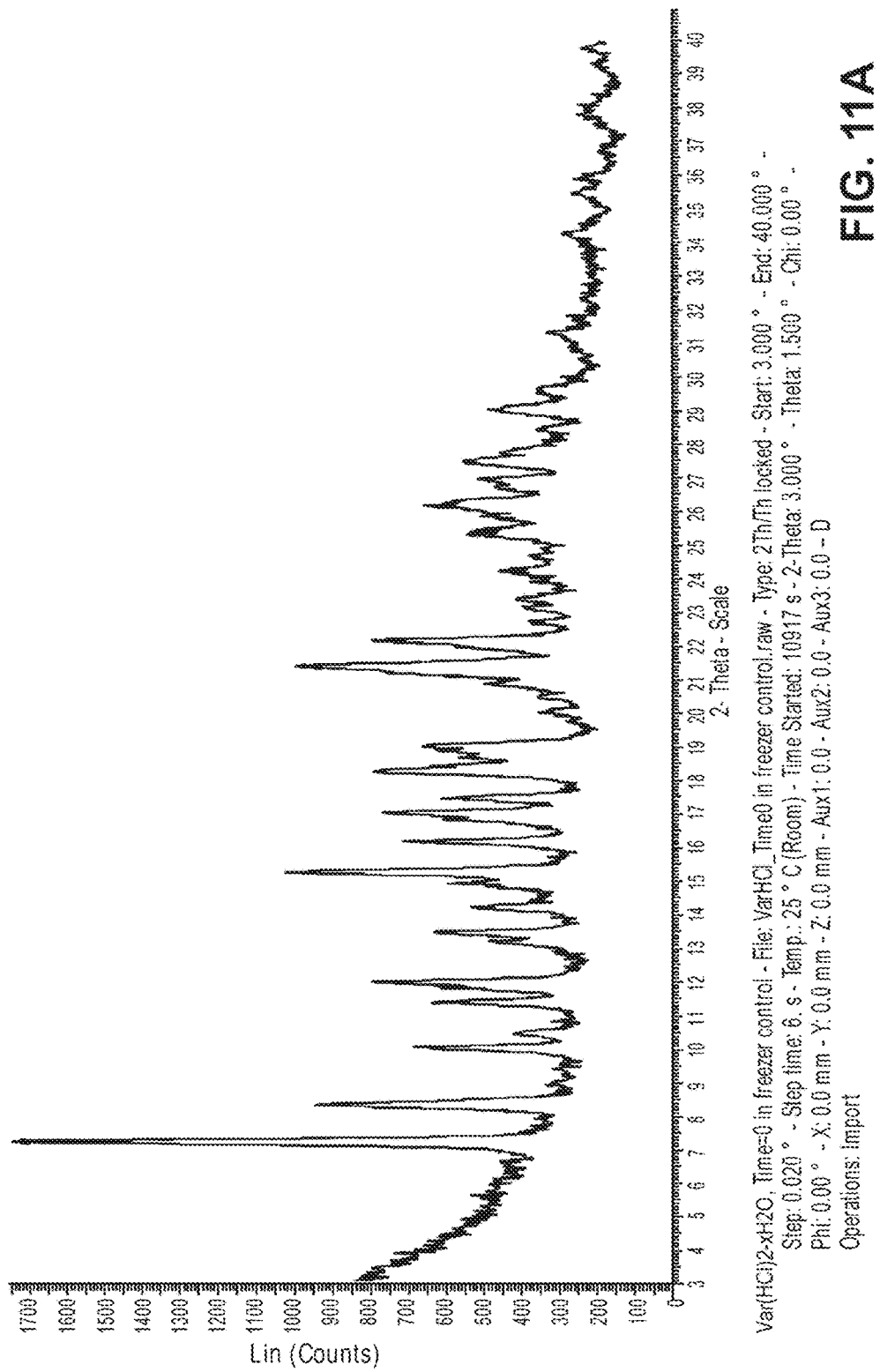
FIGS. 11A-11C illustrate results of x-ray powder diffraction (XRPD) analysis assessing crystalline forms of vardenafil formulations after micronization.
Figure 11B:
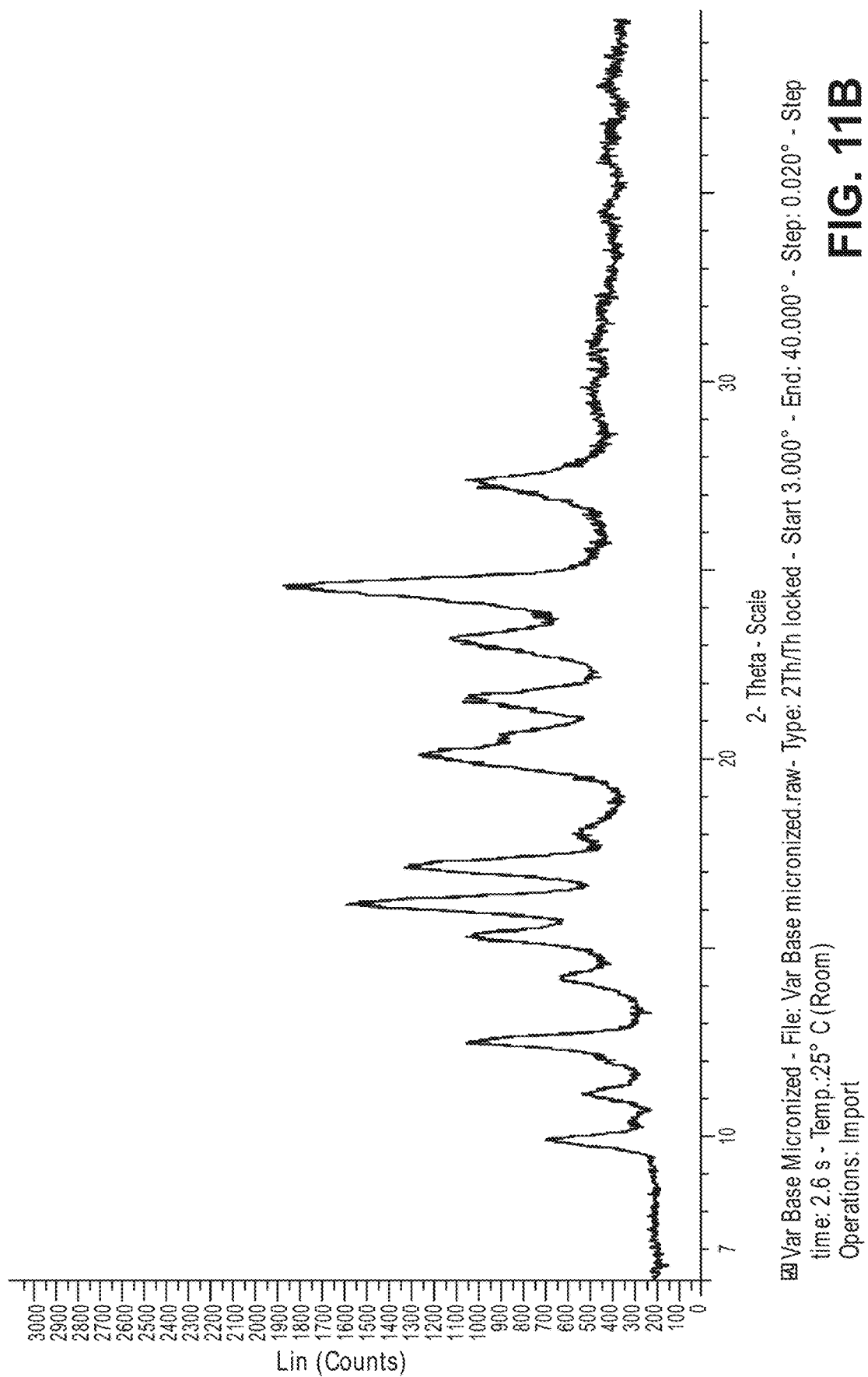
Figure 11C:
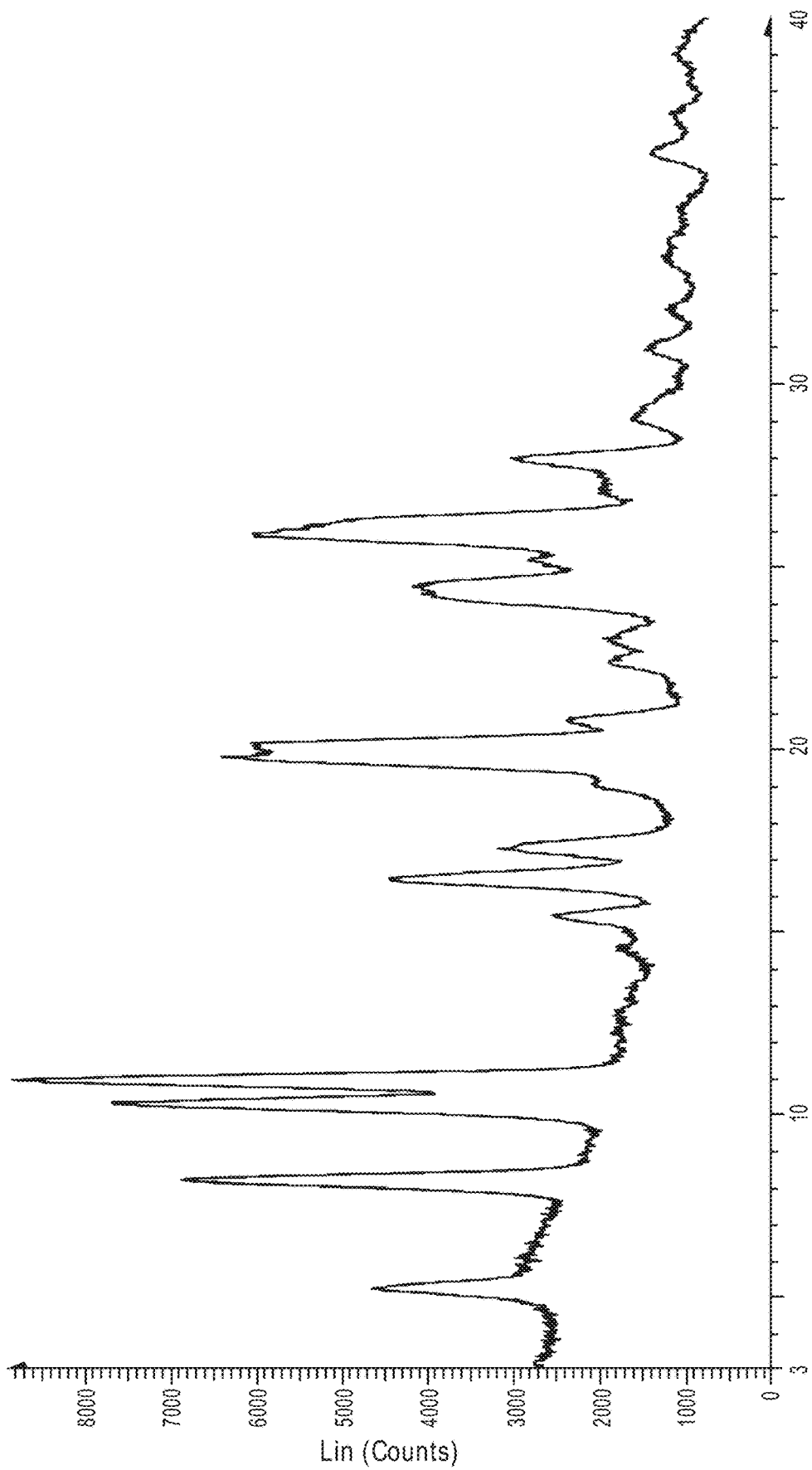

In some instances, active agents may be characterized and distinguished using DSC as shown in FIGS. 8A-8C. For example, Var(HCl)$_2$·xH$_2$O may be characterized by a onset of glass transition at about 50° C. that ended at about 110° C., a small endothermic peak at about 140° C., and two large endothermic peaks at 222° C. and 294° C. In another example, VarBase may be identified by a heat of fusion temperature of 190° C., with an onset temperature of about 177° C. when the scanning rate was set at 10° C./min, and degradation peaks when the temperature is raised above 250° C. In some instances, the melting temperature of the vardenafil forms as determined by DSC may identify different forms of VarBase. In another example, VarHCl·xH$_2$O may be identified by a large endothermic peak at 107° C., and onset temperature of about 50-60° C., and a heat of fusion temperature of about 199° C. In other instances, active agents may be characterized and distinguished using DVS as shown in FIGS. 9A-9D, TGA as shown in FIG. 10, and XRPD as shown in FIGS. 11A-11C.

Excipients

The disclosed dry powder compositions can additionally include a carrier/excipient. Dry powder compositions may contain a powder mix for inhalation of the active ingredient and a suitable powder base (a carrier, a diluent, and/or an excipient substance) such as mono-, di or poly-saccharides (for example, lactose, mannitol, trehalose, or starch). In certain cases, the carrier may form from about 1% to about 95% by weight of the formulation. In some instances, the powder base may act as a carrier, a diluent that aids in dispensing the active agent, and a fluidizing agent to assist dispersion of the active agent.

In some instances, lactose may be a suitable powder base for use with PDE5 inhibitor dry powder compositions. In some instances, lactose is a suitable carrier for vardenafil formulations for pulmonary administration because it does not react with vardenafil as shown, for example, in FIGS. 5A-5D for VarHCl·3H$_2$O. In some cases, vardenafil-lactose blends are chemically stable even though lactose is a reducing sugar that could react via a Maillard chemical reaction with the amines in vardenafil. The lactose may be, for example, alpha-lactose monohydrate, anhydrous alpha-lactose, anhydrous beta-lactose, or a blend thereof (for example, 70-80% anhydrous beta-lactose and 20-30% anhydrous alpha-lactose). In some instances, lactose (or other powder base) may be sieved, milled, micronized, or some combination thereof. The lactose may comprise a fine lactose fraction. The fine lactose fraction is defined as the fraction of lactose having a particle size of less than 7 µm, such as less than 6 µm, for example less than 5 µm. The particle size of the fine lactose fraction may be less than 4.5 µm. The fine lactose fraction, if present, may comprise 2% to 50% by weight of the total lactose component, such as 5% to 10% by weight fine lactose, for example 4.5% by weight fine lactose. In some cases, lactose of different size fractions may be combined in a dry powder composition. In some instances, the particle size of the carrier will be much greater than that of the active agent. For example, the lactose (or other powder base) may have average diameter of between about 2 µm to about 250 µm, more preferably about 5 µm to about 150 µm, or more preferably about 60 µm to about 90 µm. These sizes can be determined by laser diffraction obtaining an equivalent volume diameter, or by other sizing methods such as sieving.

The disclosed dry powder compositions may also include, in addition to the active ingredient and carrier, a further excipient (a ternary agent) such as a mono-, di or polysaccharides and their derivatives, calcium stearate or magnesium stearate, leucine and its derivatives, lecithin, human serum albumin, polylysine, polyarginine, and other force control agents. In some instances, if magnesium stearate is present in the composition, it may be present in an amount of about 0.2% to 2%, such as 0.6% to 2% or 0.5% to 1.75%, or 0.6%, 0.75%, 1%, 1.25% or 1.5% w/w, based on the total weight of the composition. The magnesium stearate may have a particle size in the range 1 µm to 50 µm, and more particularly 1 µm to 20 µm.

Alternatively, in some instances, the dry powder composition contains pure active agent, without any carriers or excipients.

Dosage Forms

In one aspect, the disclosed compositions may take the form of dry powders suitable for pulmonary administration via inhalation.

Dry powder dosage forms of PDE5 inhibitors (such vardenafil, sildenafil, tadalafil, avanafil, benzamidenafil, lodenafil, mirodenafil, udenafil, or zaprinast, or pharmaceutically acceptable salts or esters thereof) and a pharmaceutically acceptable carrier as described herein offer advantages over other traditional formulations for oral administration (such as tablets, capsules, and liquids administered by swallowing). For example, administration by inhalation of the dry powder formulation overcomes the dosing limitations of oral administrations because higher concentrations of the active agent can be delivered to the site of action (lungs) without the side effects seen with systemic administration. Similarly, administration by inhalation may even allow the use of these agents in patients who are unable to tolerate these drugs because of hypotension, drug interactions in the liver or other systemic adverse effects, including systemic toxicities associated with chronic daily use, which arise with traditional dosage forms for oral administration.

As used herein, the term "dosage form" refers to physically discrete units suitable as unitary dosages for human subjects and other mammals, each unit containing a predetermined quantity (nominal dose) of therapeutic agent calculated to produce the desired onset, tolerability, and therapeutic effects, in association with one or more suitable pharmaceutical excipients such as carriers. Methods for preparing such dosage forms are known or will be apparent to those skilled in the art. The dosage form to be administered will, in any event, contain a quantity of the therapeutic agent in a therapeutically effective amount for relief of the condition being treated when administered in accordance with the teachings of this disclosure.

In some instances, the disclosed compositions may comprise from about 2% to about 100%. In some instances, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight of the active agent may be used (in whatever chosen form). In some cases, the compositions comprise about 5% to about 50%, or about 2% to about 20% by weight of the active agent. One skilled in the art understands that the foregoing percentages will vary depending upon the particular source of active agent utilized, the amount of active agent desired in the final formulation, and the aerosol performance of the final formulation.

Figure 15A:
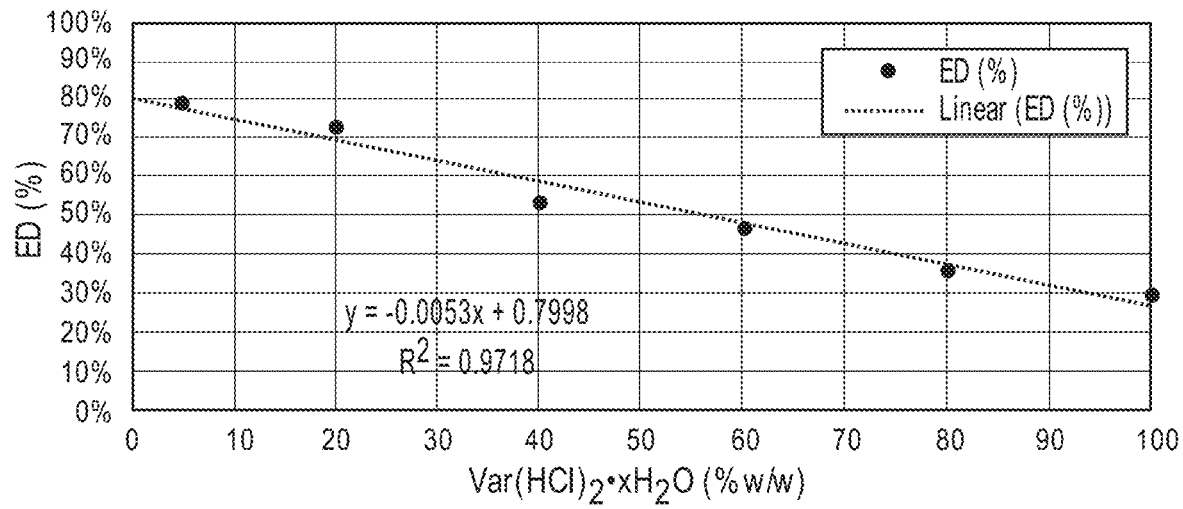

In some instances, the compositions may comprise at least about 2% by weight of the active agent, such as, for example, at least about 2% to about 20% by weight of the active agent. For example, as shown in Tables 6-8, the concentration of the active agent may be 5% to 20% in dry compositions with an acceptable carrier for pulmonary administration (such as lactose). In other instances, the concentration of active agent may be greater than 20%. For example, as shown in FIG. 15A, the active agent concentration may be anywhere from 20% to 100% active agent. For example, in some instances, the composition may 100% pure active agent, or nearly 100% pure active agent as shown, for example, in Table 5. In certain instances, for example as shown in FIG. 15A, the emitted dose of a composition upon aerosolization may decrease as the concentration of active agent increases. In some cases, this may be due to deposition of the active agent onto the inhaler device used for aerosolization as shown, for example in FIG. 15B. However, this may vary based on the configuration of the inhaler device used for aerosolization.

In another aspect, the dry powder formulation may exhibit long term stability. In some instances, this is in contrast to vardenafil in aqueous solutions, which may be more prone to acidic, basic, or oxidative degradation as shown in FIGS. 4A-4F. For example, the dry powder compositions may be stored to reduce the possibility of either dehydration or exposure to moisture in the air. The compositions may also be stable when stored at room temperature. For example, the composition may be stable at room temperature for at least 1 month, or at least 3 months, or at least 6 months as shown in FIGS. 5A-5D. In some instances, the composition may be stable at room temperature for about 1 year or about two years. In some instances, the dry powder composition contain primarily pure active agent. In other instances, the dry powder composition may contain at least 50%, such as, for example, at least 90%, pharmaceutically acceptable carrier/excipient. In some instances, the excipient may include lactose.

The disclosed dry powder compositions are generally aerosolizable for the purposes of administration as a dry powder dispersion. Suitable devices for aerosolization include dry powder inhaler and metered dose inhalers. Such devices function to emit a dispersion of the formulation contained within the device. The characteristics of the emitted dispersion, particularly the aerosol performance of the composition, are properties that relate in part to the dry powder composition.

Preparation of Dry Powder Formulations

Any suitable methods can be used to mix the formulation comprising the active agent as described, for example, in Remington: The Science and Practice of Pharmacy, 25$^{th}$ Edition. In some instances, the active agent and carrier are combined, mixed and the mixture may be directly packaged for aerosolization (such as in a capsule). In certain instances, the active agent and carrier are combined and mixed using the method of geometric dilution as generally known in the art. In one aspect, disclosed is a method of producing a powder pharmaceutical composition comprising the active agent, by contacting at least about 2% of the active agent by weight relative to the total weight of the overall pharmaceutical composition with at least one pharmaceutically acceptable carrier. In some instances, the active agent may be a PDE5 inhibitor, such as vardenafil, or a pharmaceutically acceptable salt, ester, or solvate thereof as described herein. In some instances, the active agent may be at least about 2% by weight of the composition, or some other amount as described above.

Active ingredients for administration by inhalation generally have a controlled particle size. The optimum particle size for inhalation into the bronchial system is usually 1-10 preferably 1-5 µm. Particles having a size above 20 µm are generally too large when inhaled to reach the small airways. To achieve the desired particle size for the active agent, the compound as produced may be size reduced by conventional means, such as by micronization. Micronization of the active agent or of all formulation components can be performed using any suitable commercially available apparatus such as those described in Remington: The Science and Practice of Pharmacy, 25$^{th}$ Edition. For example, micronization may be performed by air-jet micronization, spiral milling, controlled precipitation, high-pressure homogenization, spray drying, or cryo-milling. The desired fraction may be separated out by air classification or sieving. Preferably, the active agent particles will be crystalline. In some instances, the active agent alone can be micronized prior to mixing. In some instances, as shown in FIGS. 6A-6C and summarized in Table 3, vardenafil compounds may be micronized within the respirable range. For example, the $D_{V50}$ of the micronized particles may be between about 1 μm and about 2 μm with a span of about 0.25 to about 1.6.

In certain cases, it may be desirable to increase the particle size of the active agent (for example, after micronization), which can be performed, for example, by granulation.

In some aspects, mixing is performed by agitating the components of the dry powder formulations to produce a mixture having a uniform concentration of active agent. For example, the components may be combined and then mixed such as by a low shear or high shear blender and/or agitated at high speed using a mechanical mixer. In some instances, the components may be mixed at an agitation speed of about 20 rpm, about 50 rpm, or about 100 rpm. In some instances, the components are mixed at an agitation speed of about 99-100 rpm. The components should be mixed for a sufficient time to ensure uniformity of the blend. For example, the components may be mixed for at least 5 min, 10 min, 15 min, or 20 min. In some instances, after an initial mixing step, blend uniformity of the mixture may be assessed and, if necessary, the mixture may be agitated for an additional period of time until the desired blend uniformity is achieved. Blend uniformity may be assessed as the coefficient of variation for samples assessed throughout the mixture. In some instances, the dry powder composition after mixing has a coefficient of variation of no more than about 5% or, in some instances, no more than about 10%. In one example, as shown in FIG. 12, a 5% blend of $Var(HCl)_2 \cdot xH_2O$ and lactose had a blend uniformity (% coefficient of variation) less than about 5% when mixed for about 5-20 min at about 100 rpm.

Following mixing, a relaxation or de-energizing step may be performed to allow the powder blend to discharge built up electrostatic charges from handling. This step may involve incubation at a certain temperature from room temperature to near 50° C. for a predetermined time from 1 day to 30 days, or exposure to a controlled humidity air source for a controlled time period, or some other method of charge dissipation commonly known. Alternatively, an ionizing source that produces approximately equal amounts of positive and negative ions may be used to dissipate charge.

Once the dry powder composition is obtained, it may be packaged into individual doses suitable for administration via inhalation. The formulation may be transferred into individual doses using a dosing system that is commonly used to fill capsules, blister cavities, reservoirs, and containers. Following filling of the doses, the powder is ready for dosing from an inhaler device. In some instances, the formulation may be packaged in a blister dose containment system. For example, capsule material may include a gelatin or HPMC (hydroxypropylmethylcellulose) capsule dose containment system. In general, the capsules may each contain one dose, or multiple capsules can be used to contain the equivalent of one dose. Examples of commercial dry powder inhaler products where the powder is stored in capsules include the FORADIL® Aerolizer®, the SPIRIVA® HandiHaler®, and the VENTOLIN® Rotahaler (GSK). In some instances, the formulation may be packaged in individual blisters, where one blister may contain one dose. Examples of commercial dry powder inhaler products where the powder is stored in blister dose containment systems include the FLOVENT® Diskus®, SEREVENT® Diskus®, and the ADVAIR® Diskus®. In some instances, the formulation may be packaged into a reservoir, where a particular reservoir may contain sufficient powder for multiple doses. Examples of commercial dry powder inhaler products where the powder is stored in reservoirs include the ASMANEX® Twisthaler®, SYMBICORT® Turbuhaler® and the Budelin® Novolizer®. Still other embodiments are possible. In some instances, the composition may be packaged to have a nominal load of about 3 mg to 30 mg. Based on the aerosol performance properties and concentration of the active agent in the dry powder composition, the composition may be packaged to have a delivered dose of at least about 0.1 mg to about 20 mg, or at least about 0.25 mg to about 20 mg, or at least about 0.5 mg to about 10 mg, or at least about 0.1 mg, about 0.25 mg, 0.5 mg, about 1 mg, about 5 mg, about 10 mg, about 15 mg, or about 20 mg. In some instances, the composition may be packaged to have a delivered dose of about 0.25 mg to 20 mg, including delivered doses in the range of about 0.25 mg to about 5 mg, about 0.25 mg to about 2 mg, about 0.25 mg to about 3 mg, about 0.25 mg to about 4 mg, about 1 mg to about 5 mg, about 2 mg to about 8 mg, about 2 mg to about 12 mg, and about 5 mg to about 15 mg.

III. Methods of Administration

The compositions disclosed herein are useful in therapeutic applications, such as for treating pulmonary hypertension, cystic fibrosis, and congestive heart failure. Importantly, the compositions of the present invention provide the rapid and predictable delivery of an active agent in the lungs that should increase the bioavailability of the active agent, overcoming the limitations of oral dosing and reducing risk of drug interactions and systemic side effects. In particular, the delivery of the therapeutic agent optimizes absorption within the lungs. As a result, the therapeutic agent can reach the site of action locally in the lung, or in systemic circulation, in a substantially shorter period of time and at a substantially higher local lung concentration than with traditional oral (for example, tablet) administration. Also, as elevated oral doses may be associated with increased systemic side effects, administration of the dry powder composition via the pulmonary route may permit higher concentrations of active agent to be administered than with oral administration.

In addition, the dry powder compositions disclosed herein offer advantages over compositions for oral administration. In particular, vardenafil exhibits a good balance between lipophilicity (relatively low) and solubility (relatively high), which is desirable for a dry powder formulation for pulmonary delivery to facilitate cellular uptake, lung residence time, and metabolism within the airways. An advantage of inhaled compositions over oral dosage forms may be the short time until effects are observed. The short onset of action can be important for many diseases. Another advantage of dry powder formulations for inhalation is avoiding metabolism in the liver and side effects associated therewith at high concentrations of active agent.

Administration of the compositions disclosed herein is preferably carried out via any of the accepted modes of pulmonary administration, particularly oral dry powder inhalation. In some instances, the composition may be administered through the mouth or through the nasal passages. Suitable devices for administration of the dry powder composition include dry powder inhalers and metered dose inhalers.

FIG. 13 is a block diagram illustrating methods for aerosolizing such dry powder compositions according to certain aspects. As a first step 1301 of the method 1300, a powder pharmaceutical composition comprising a) at least 2% by weight of a PDE5 inhibitor, or a pharmaceutically acceptable salt or ester thereof, relative to the total weight of the overall pharmaceutical composition, and b) at least one pharmaceutically acceptable carrier may be provided. Step 1302 illustrates that an inhaler comprising a dispersion chamber having an inlet and an outlet, the dispersion chamber containing an actuator that is movable reciprocatable along a longitudinal axis of the dispersion chamber may be provided. Steps 1301 and 1302 may be performed in any order or simultaneously. As shown in step 1303, air flow is induced through the outlet channel to cause air and the powder pharmaceutical composition to enter into the dispersion chamber from the inlet, and to cause the actuator to oscillate within the dispersion chamber to assist in dispersing the powder pharmaceutical composition from the outlet for delivery to a subject through the outlet. In some instances, the powdered medicament may be stored within a storage compartment (of the inhaler), and wherein the powder pharmaceutical composition is transferred from the storage compartment, through the inlet and into the dispersion chamber. In certain cases, the inlet may be in fluid communication with an initial chamber, and wherein the powder pharmaceutical composition is received into the initial chamber prior to passing through the inlet and into the dispersion chamber.

In practice, a patient may prime an aerosolization device by puncturing the container holding the formulation (such as a capsule or blister) that is contained within a powder reservoir, or the patient may transfer drug from the powder reservoir into the inhalation portion of the device, and then inhale. Inhalation by a patient draws the powder through the inhaler device where powder entrainment results in dilation, fluidization, and at least the partial de-agglomerating of powder aggregates and micro aggregates and then dispersion of the API powder aerosol (in other words, aerosolization). This approach may be useful for effectively dispersing both pure drug-powder formulations where there are no carrier particles are present and traditional binary or ternary carrier-based formulations.

Exemplary devices for use in administering the dry powder composition include dry powder inhalers and metered dose inhalers such as, but not limited to Twisthaler® (Merck), Diskus® (GSK), Handihaler® (BI), Aerolizer®, Turbuhaler® (AstraZeneca), Flexhaler® (Astrazeneca), Neohaler® (Breezhaler®) (Novartis), Easyhaler® (Orion), Novolizer® (Meda Pharma), Rotahaler® (GSK), and others. As known to those skilled in the art, difference devices will have different performance characteristics based on the device resistance, deaggregation mechanisms, adhesion of drug to the internal flow channels, ability of the patient to coordinate and inhale, among other factors.

Figure 14A:
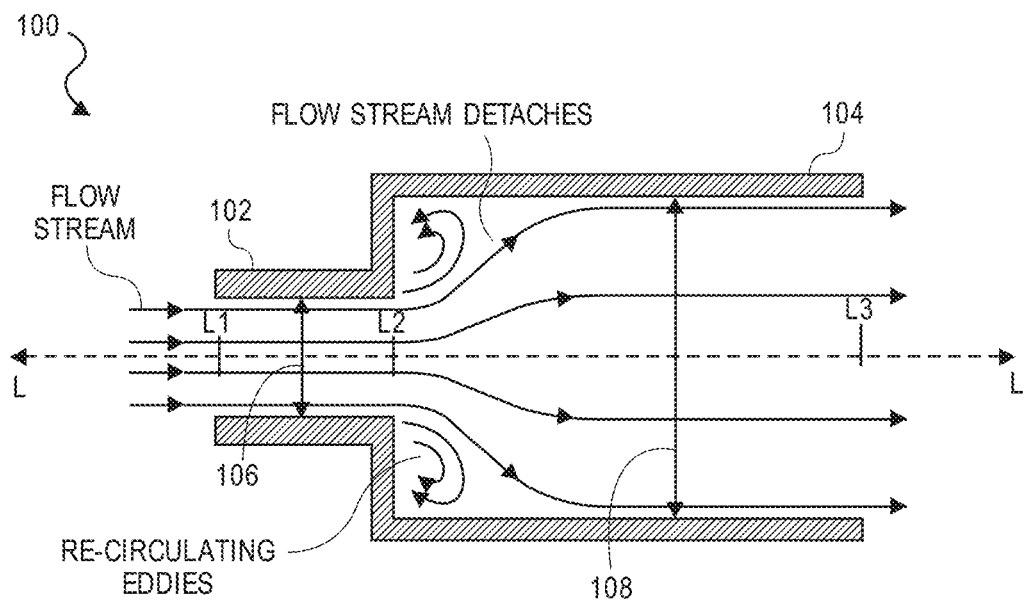

In another aspect, the dry powder compositions may be administered using a dry powder inhaler or a metered dose inhaler that comprises a dry powder deaggregator, also referred to as a powder dispersion mechanism. Exemplary powder dispersion mechanisms are described in U.S. Patent Publication Nos. 2013/0340754 and 2013/0340747, which are incorporated herein by reference in their entirety. In some instances, such powder dispersion mechanisms may comprise of a bead positioned within a chamber that is arranged and configured to induce a sudden, rapid, or otherwise abrupt expansion of a flow stream upon entering the chamber. In general, the chamber may be coupled to any form or type of dose containment system or source that supplies powdered active agent into the chamber. Referring now to FIG. 14A, a cross-section of an example tubular body 100 having an inlet 102 and a dispersion chamber 104 is shown according to the principles of the present disclosure. In this example, a fluid (air) flow path of the inlet 102 is defined by a first internal diameter 106, and a fluid (air) flow path of the chamber 104 is defined by a second internal diameter 108. Although shown approximately constant in FIG. 14A, at least one of the first internal diameter 106 and the second internal diameter 108 may vary in dimension as defined with respect to a longitudinal axis L of the tubular body 100. In addition to providing desirable fluid flow characteristics, as discussed further below, these configurable dimensions may be defined such as to provide for a draft angle for injection molding.

Figure 14B:
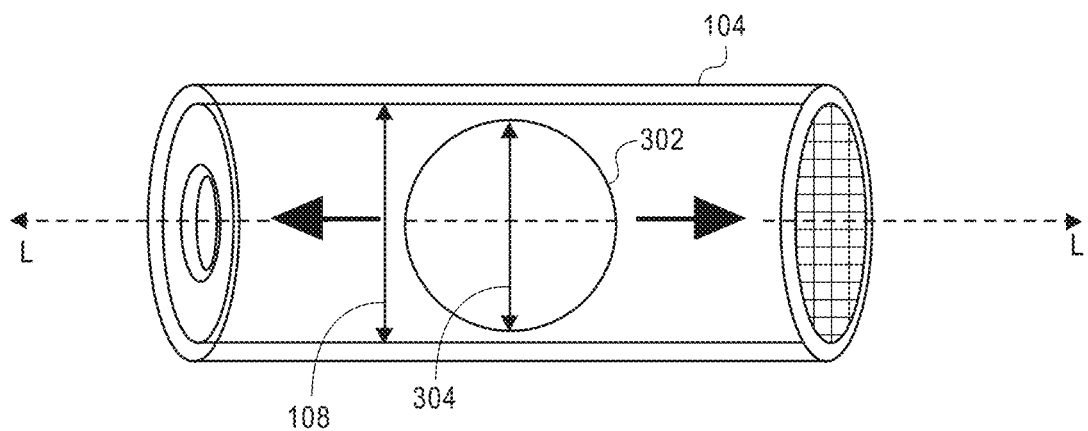

For example, referring now additionally to FIG. 14B, a bead 302 may be positioned within the chamber 104 of the tubular body 100 of FIG. 14A. In this example, the bead 302 may be approximately spherical, at least on the macroscale, and oscillate in a manner similar to that described in U.S. Pat. No. 8,651,104, which is herein incorporated by reference in its entirety. Further, a relationship between the diameter 304 of the bead 302, the first internal diameter 106 of the inlet 102, and the second internal diameter 108 of the chamber 104 may be as described in U.S. Patent Publication Nos. 2013/0340754 and 2013/0340747, which are incorporated herein by reference in their entirety.

In some instances, the powder dispersion mechanism may be coupled to a dry powder inhaler or metered dose inhaler such as a commercially available device. The dispersion mechansim (dispersion chamber) may be adapted to receive an aerosolized powdered active agent from an inlet channel such as described, for example, in U.S. Patent Publication Nos. 2013/0340754, which is incorporated herein by reference in its entirety. The powder dispersion mechanism (dry powder deaggregator) may be adapted to receive at least a portion of the aerosolized powdered active agent from the first chamber of the inhaler. The powder dispersion mechanism may include a dispersion chamber that may hold an actuator that is movable within the dispersion chamber along a longitudinal axis. The dry powder inhaler may include an outlet channel through which air and powdered active agent exit the inhaler to be delivered to a subject. A geometry of the inhaler may be such that a flow profile is generated within the dispersion chamber that causes the actuator to oscillate along the longitudinal axis, enabling the oscillating actuator to effectively disperse powdered medicament received in the dispersion chamber for delivery to the patient through the outlet channel.

In one example, the powder dispersion mechanism may have an inlet diameter of about 2.72 mm and an oscillation chamber length and diameter of about 10 mm and about 5.89 mm, respectively. In some instances, the powder dispersion mechanism may include a bead having a diameter of 4 mm in the chamber. In some instances, the bead may have a density of about 0.9 mg/mm$^3$. In some instances, the bead may be made of polypropylene or a similar material. In some instances, the powder dispersion mechanism can be coupled with a commercial inhaler or other component to form a delivery system for aerosolization of the dry powder compositions. In some cases, the delivery system may work at effectively at different airflow rates and pressure drops within the range of normal physiological inhalation for a subject such as, for example, about 40 to about 60 L/min and about 2 to about 4 kPa.

In certain instances, a dry powder inhaler system may be used to aerosolize and administer the dry powder formulation. The dry powder inhaler system may include a receptacle containing an amount of powdered active agent. The dry powder inhaler system may include an inlet channel that is adapted to receive air and powdered active agent from the receptacle. The dry powder inhaler system may include a first chamber that is adapted to receive air and powdered active agent from the inlet channel. A volume of the first chamber may be greater than volume of the inlet channel. The dry powder inhaler system may include a dispersion chamber that is adapted to receive air and powdered medicament from the first chamber. The dispersion chamber may hold an actuator that is movable within the dispersion chamber along a longitudinal axis. The dry powder inhaler system may include an outlet channel through which air and powdered active agent exit the dispersion chamber to be delivered to a patient. A geometry of the system may be such that a flow profile is generated within the system that causes the actuator to oscillate along the longitudinal axis, enabling the oscillating actuator to effectively disperse powdered medicament received in the dispersion chamber for delivery to the patient through the outlet channel.

In one aspect, a method for aerosolizing a powdered medicament is disclosed. The method may include providing an inhaler comprising a first chamber, and a dispersion chamber, the dispersion chamber containing an actuator that is movable within the dispersion chamber along a longitudinal axis, and an outlet channel. The method may include inducing air flow through the outlet channel to cause air and powdered medicament to enter into the first chamber through the inlet channel into the dispersion chamber, and to cause the actuator to oscillate within the dispersion chamber to effectively disperse powdered medicament passing through the first chamber and the dispersion chamber to be entrained by the air and delivered to the patient through the outlet channel.

Several different parameters are used as measures of the aerosol performance of a dry powder formulation under certain airflow and pressure drop conditions. For example, the emitted dose" (ED(%)) of a formulation refers to the mass of an active agent that is emitted from a dry powder inhaler aerosolization device as a percentage of a nominal dose mass. Powder formulations that exhibit better powder flow properties often result in higher ED(%). Another parameter is the respirable fraction (RF(%)) of the formulation, which is the mass of an active agent that is below a certain aerodynamic cutoff size as a percentage of a nominal dose mass. Fine particle fraction is the mass of active agent having an aerodynamic diameter below about about 5 μm as a percentage of an emitted dose mass. This response is often used to evaluate the efficiency of aerosol deaggregation. For example, the % FPF(ED) may be the percentage of an active agent of a formulation having an aerodynamic diameter at or below about 5 μm. The respirable fraction represents the proportion of powder aerosol active agent that can enter the deep respiratory tract. Another parameter is mass median aerodynamic diameter (MMAD). The MMAD is the median of the distribution of airborne particle mass with respect to the aerodynamic diameter. Airflow conditions are generally selected to span the range of physiological inhalation capabilities of a subject. For example, for a human subject, the pressure drop for an inhalation may be in the range of about 0.5 kPa to about 8 kPa, more typically within the range of about 1 kPa to about 4 kPa, and including airflow rates of about 5 L/min to about 120 L/min, more typically in the range of about 15 L/min to about 100 L/min.

In some instances, the dry powder composition may have an emitted dose of at least about 20%, about 25%, about 30%, about 35%, about 40%, about 50%, about 55%, about 60%, about 65%, about 70%, about 75%, about 80%, about 85%, about 90%, or about 95% upon aerosolization. In one example, as shown in Table 5, pure active agent compositions may have an emitted dose of at least about 65% for VarBase, at least about 25% for Var(HCl)$_2$·xH$_2$O, at least about 70% for Var(HCl)$_2$·xH$_2$O (rehydrated), and at least about 40% for VarHCl·xH$_2$O. In some cases, the active agent may be micronized. In some instances, nominal dose may not impact emitted dose of pure active agent compositions. In another example, as shown in Tables 6-8, dry powder compositions of vardenafil compounds plus a carrier, such as lactose, may have emitted doses that are, on average, somewhat higher than the pure active agent compositions. For example, a 5% Var(HCl)$_2$.xH$_2$O composition may have an emitted dose of at least about 75% regardless of whether the nominal load used for aerosolization was 10 mg or 20 mg as shown in Table 6. In another example, 5% and 20% Var (HCl)$_2$·xH$_2$O compositions may have an emitted dose of at least about 80% as shown in Table 7. In another example, 5% and 20% VarBase and VarHCl.xH$_2$O compositions may have emitted doses of at least about 70% as shown in Table 8.

In certain cases, the dry powder composition may have a fine particle fraction of at least about 20%, about 25%, about 30%, about 35%, about 40%, about 50%, about 55%, about 60%, about 65%, about 70%, about 75%, about 80%, about 85%, about 90%, or about 95% upon aerosolization. In some instances, composition of pure active agent may have a fine particle fraction of at least about 20% as shown in Table 5. For example, as shown in Table 5, pure active agent compositions may have an emitted dose of at least about 35-60% for VarBase, at least about 85-90% for Var(HCl)$_2$·xH$_2$O, at least about 60-65% for Var(HCl)$_2$.xH$_2$O (rehydrated), and at least about 65-70% for VarHCl·xH$_2$O. In some cases, a composition of a vardenafil compound and a carrier (such as lactose) may have a fine particle fraction of at least about 40-50% as shown in Tables 6-8. For example, a 5% Var (HCl)$_2$.xH$_2$O composition may have a fine particle fraction of at least about 65-70% regardless of whether the nominal load used for aerosolization was 10 mg or 20 mg as shown in Table 6. In another example, 5% and 20% Var(HCl)$_2$· xH$_2$O compositions may have a fine particle fraction of at least about 65-80% as shown in Table 7. In some instances, increasing the concentration of active agent (such as Var (HCl)$_2$·xH$_2$O) in the composition may increase the fine particle fraction upon aerosolization. In another example, 5% and 20% VarBase and VarHCl·xH$_2$O compositions may have a fine particle fractions of at least about 40-70% as shown in Table 8. In some instances, increasing the active agent (such as VarBase and VarHCl·xH$_2$O) in the composition may increase the fine particle fraction upon aerosolization. In some instances, VarHCl·xH$_2$O has a slightly higher respirable fraction upon aerosolization than VarBase.

In certain cases, the dry powder composition may have a respirable fraction of at least about 20%, about 25%, about 30%, about 35%, about 40%, about 50%, about 55%, about 60%, about 65%, or about 70%, upon aerosolization. In one example, as shown in Table 5, pure active agent compositions may have a respirable fraction of at least about 25% or 45% for VarBase depending on nominal dose (10 mg vs 3 mg), at least about 20% for Var(HCl)$_2$·xH$_2$O (regardless of nominal dose, 10 mg vs 3 mg), at least about 45% for Var(HCl)$_2$·xH$_2$O (rehydrated), and at least about 30% for VarHCl·xH$_2$O. In some cases, the active agent may be micronized. In another example, a 5% Var(HCl)$_2$·xH$_2$O composition may have a respirable fraction of at least about 50% regardless of whether the nominal load used for aerosolization was 10 mg or 20 mg as shown in Table 6. In another example, 5% and 20% Var(HCl)$_2$.xH$_2$O compositions may have a respirable fraction of at least about 50-60% as shown in Table 7. In some instances, increasing the concentration of the active agent may diminish the respirable fraction of the composition (such as VarHCl.xH$_2$O) upon aerosolization. In another example, 5% and 20% VarBase and VarHCl·xH$_2$O compositions may have respirable fractions of at least about 25-50% as shown in Table 8. In some instances, increasing the concentration of the active agent (such as VarBase and VarHCl·xH$_2$O) may diminish the respirable fraction of the composition upon aerosolization.

In some instances, the MMAD of the composition is less than about 10 μm, less than about 5 μm, or less than about 3 μm, upon aerosolization. For example, upon aerosolization, the compositions may have a mass median aerodynamic diameter (MMAD) of between about 0.5 μm and about 8 μm, such as, for example, between about 1 μm and about 2 μm, between about 1 μm and about 3 μm, between about 0.5 μm and about 4 μm, or between about 0.5 μm and about 5 μm, or other ranges therein. In some instances, as shown in Tables 6-7 and 9, the composition may have a relatively small MMAD of about 0.7 to about 1.5 μm, including about 0.7 μm to about 1. 5 μm, about 0.8 μm to about 0.85 μm, about 0.8 μm to about 0.95 μm, and about 0.9 μm to about 1.2 μm.

In certain cases, the dry composition formulations may have similar aerosolization properties at both high and low airflow rates. This may reduce variability in dosing (due to inhalation variability). For example, as shown in Table 9, a 5% Var(HCl)$_2$·xH$_2$O composition has similar emitted dose and respirable fraction upon aerosolization at both 2 kPa and 4 kPa airflow using a dry powder inhaler.

Upon inhalation, some portion of the dry powder composition, particularly the active agent, is emitted from a delivery system, such as an inhaler, upon aerosolization of the dry powder composition. Generally, the term delivered dose refers to the percentage mass emitted dose (ED(%)) as a function of the nominal dose mass in the delivery system. In some instances, upon aerosolization and inhalation, the composition may have a delivered dose of about 0.25 mg to 20 mg, including delivered doses in the range of about 0.25 mg to about 5 mg, about 0.25 mg to about 2 mg, about 0.25 mg to about 3 mg, about 0.25 mg to about 4 mg, about 1 mg to about 5 mg, about 2 mg to about 8 mg, about 2 mg to about 12 mg, and about 5 mg to about 15 mg. In some instances, upon aerosolization, the composition may have a delivered dose of at least about 0.1 mg to about 20 mg, or at least about 0.25 mg to about 20 mg, or at least about 0.5 mg to about 10 mg, or at least about 0.1 mg, about 0.25 mg, 0.5 mg, about 1 mg, about 5 mg, about 10 mg, about 15 mg, or about 20 mg.

Figure 15B:
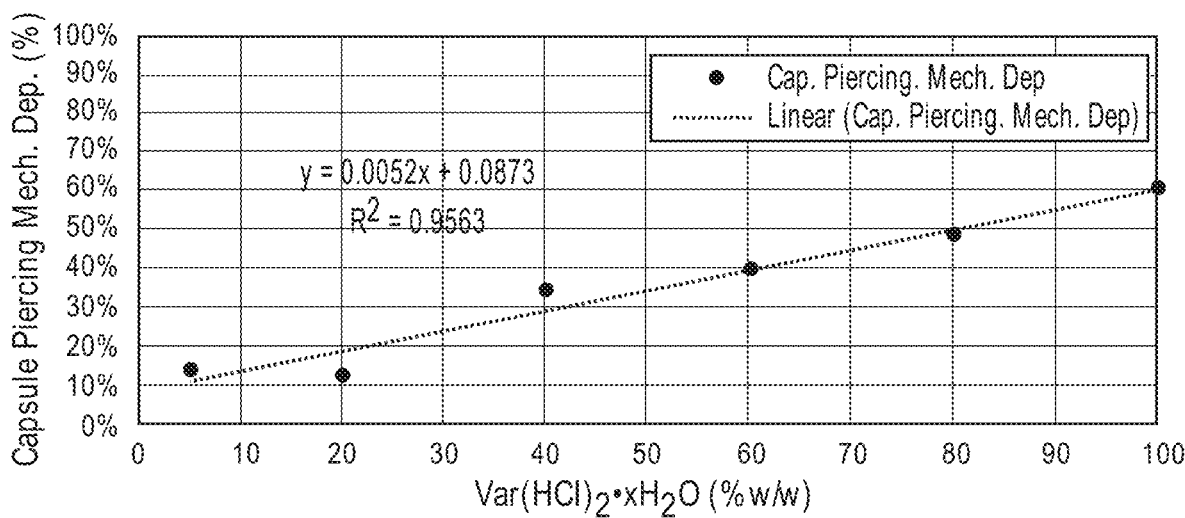

One issue relating to use of inhalers for pulmonary administration of dry powder composition is that, in some instances, depending on the mechanism by which the inhaler components operate (for example, the capsule piercing mechanism), an amount of the composition may be deposited within the device and not emitted. For example, as shown in FIGS. 15A and 15B, deposition of active agent increased approximately linearly as active agent concentration increased for one type of dry powder inhaler.

In some instances, the dry powder composition is formulated and packaged to have substantial delivered (emitted) dose uniformity. The uniformity of the emitted dose reflects the safety, quality, and efficacy of the dry powder compositions. In some instances, the composition may have a delivered dose uniformity of about 75% to about 125% target dose over 2-60 inhalations.

The percent recovery (% recvy) is a way to check the mass balance before and after dose delivery by capturing and measuring the amount of drug discharged from an inhaler to verify accuracy of analysis. In some instances, the total mass of drug collected in all of the components divided by the total number of minimum recommended doses discharged is not less than 75% and not more than 125% of the average minimum recommended dose determined during testing for delivered-dose uniformity. See USP <601>. In some instances, the percent recovery of the dry powder formulation is at least about 95% or at least about 100%, for example, as shown in Table 5 and Table 8, for various dry compositions with different active agents and concentrations and nominal loads.

IV. Methods of Treatment

The compositions disclosed herein have particular utility in the area of human and veterinary therapeutics. In one aspect, a method of treating a disease in a mammal in need thereof is provided, the method comprising administering to the mammal via a pulmonary route an effective amount of a powder pharmaceutical composition comprising a) at least about 2% of a PDE5 inhibitor, or a pharmaceutically acceptable salt or ester thereof, by weight relative to the total weight of the overall pharmaceutical composition dose, and b) at least one pharmaceutically acceptable carrier. The dry powder formulations and methods described herein provide improved methods of treating certain diseases that are currently treated only with oral formulations that are swallowed. In some instances, the disease may be a lung disease such as pulmonary hypertension or cystic fibrosis. For example the lung disease may be pulmonary arterial hypertension. In some cases, the disease may be a heart disease. For example, the heart disease may be congestive heart failure/disease.

PDE5 inhibitors are used to augment the action of endogenous nitric oxide resulting in vasodilatation and reduction of smooth muscle proliferation in patients with pulmonary hypertension. Pulmonary hypertension includes, but is not limited to, pulmonary arterial hypertension, primary pulmonary hypertension, secondary pulmonary hypertension, familial pulmonary hypertension, sporadic pulmonary hypertension, precapillary pulmonary hypertension, pulmonary artery hypertension, idiopathic pulmonary hypertension, thrombotic pulmonary arteriopathy, plexogenic pulmonary arteriopathy and pulmonary hypertension associated with or related to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, congenital heart disease, pulmonary venus hypertension, chronic obstructive pulmonary disease, interstitial lung disease, lung fibrosis, sleep-disordered breathing, alveolarhyperventilation disorder, chronic exposure to high altitude, neonatal lung disease, alveolar-capillary dysplasia, sickle cell disease, other coagulation disorders, chronic thromboemboli, connective tissue disease, lupus, schistosomiasis, sarcoidosis or pulmonary capillary hemangiomatosis.

Cystic fibrosis is caused by a defective or missing CFTR protein resulting from mutations in the CFTR gene. There are more than 1,800 The F508del mutation, results in a "trafficking" defect, in which the CFTR protein does not reach the cell surface in sufficient quantities. The absence of working CFTR proteins results in poor flow of salt and water into and out of cells in a number of organs, which results in a thick, sticky mucus that builds up and blocks the airways of in the lungs, causing chronic lung infections, inflammation and progressive lung damage. While cystic fibrosis is caused by mutations in the CTFR gene, cGMP has a key role in the cell and regulates many aspects of proper CFTR functioning. cGMP is metabolized by the PDE5 enzyme. Thus, in some instances, PDE5 inhibitors may maintain and control levels of cGMP, which, in turn, may modulate CFTR and improve CTFR function. PDE5 inhibitors have also been shown to exhibit anti-inflammatory and anti-pseudomonal activity in preclinical models. (Poschet et al. 2007 Lung Cell. Molec. Physiol. 293(3):L712-L719) For example, oral sildenafil, a PDE5i, has reduced biomarkers of lung inflammation in clinical trials in adult CF patients with F508del mutation. (Taylor-Cousar et al., Abstract A94, Therapeutic & Diagnostic Adv. Cystic Fibrosis 2013, p. A2066.)

PDE5 expression appears to be increased in a number of myocardial disease states, including chronic myopathies involving myocyte or ventricular hypertrophy. (Schwartz et al. 2012 JACC 59(1):9-15) In hypertrophied myocardium, PDE5 inhibitors increase cGMP, which inhibits phosphodiesterase-3 and thereby increases cyclic adenosine monophosphate.(cAMP). cAMP in turn activates protein kinase A, which increases intracellular calcium and contractility (Schwartz). PDE5 inhibitors were found to improve hemodynamic and clinical parameters in patients with congestive heart disease in a number of small trials (Schwartz). Small trials in patients with congestive heart disease demonstrated the greatest benefit of PDE5Is in patients with secondary PAH and right ventricular failure (Lewis et al. 2007 Circulation 116:1555-1562; Melenovsky et al. 2009 J. Am. Coll. Cardiol. 54:595-600.).

In some cases, the delivery of dry powder formulations of PDE5 inhibitors may be more efficient that oral dose formulations by creating a high local lung concentration of the active agent, potentially yielding a quicker onset of action with likely comparable or enhanced efficacy with fewer side effects.

Local delivery of PDE5i directly into the lung may circumvent poor oral bioavailability and provide even greater selectivity of effect by delivering high local lung concentrations with lower total dose exposure with the potential for greater efficacy. Administration of dry powder formulations via inhalation are also advantageous because the route of administration allows avoidance of extensive first pass hepatic metabolism and drug-drug interaction with CYP3A inducers/inhibitors. Many drugs used to treat lung diseases (such a cystic fibrosis and pulmonary hypertension) can be metabolized using this enzyme system and, therefore, are susceptible to interactions or contraindications. Inhalation delivery may avoid the severity of these interactions because avoidance of first pass metabolism, while the lower administered dose (but higher lung tissue dose) may minimize the potential for interactions. Inhalation delivery may also avoid adverse side effects associated with orally administered PDE5 inhibitor formulations, such as hypotension, hearing or visual improvement, headache, dyspepsia, flushing, insomnia, erythema, dyspnea, rhinitis, diarrhea, myalgia, pyrexia, gastritis, sinusitis, paraesthesia. For example, in many chronic obstructive pulmonary disease (COPD) patients, ventilation/perfusion (V/Q) mismatch may preclude the use of oral PDE5 inhibitor formulations as these patients generally have some degree of hypoxic vasoconstriction that can be worsened by the action of PDE5 inhibitors and other adverse effects, particularly in patients with moderately severe COPD. In some instances, a dry powder PDE5 inhibitor formulation with low oral and throat deposition and swallowing may better target the active agent to the ventilated areas of the lung, controlling the pulmonary hypertension while avoiding increasing V/Q mismatch and hypoxia. Thus, in some instances, administration of PDE5 inhibitors via a pulmonary route may be useful for treating subjects who are unable to tolerate clinically useful doses of oral formulations because of hypotension, drug interactions or other systemic adverse effects.

In some instances, lower doses of dry powder formulations (as compared to oral doses for swallowing) may be administered to a subject. In some instances, similar doses of the dry powder formulations as used for oral doses for swallowing may be administered to a subject, wherein, because the drug is administered directly to the target site, there may be a reduction in systemic drug levels using a dry powder inhaler formulation. This may lead to a reduction of systemic toxicities associated with chronic daily use (headache, lowered blood pressure, cardiovascular effects anterior ischemic optic neuropathy, priapism, vaso-occlusive crises.

In general, orally administered PDE5 inhibitors dissolve in the digestive tract and are absorbed into the blood stream. Upon reaching the pulmonary circulation, the PDE5 compound diffuses across the vascular endothelium into the surrounding smooth muscle cells, where it inhibits the PDE5 enzyme present in the intracellular fluid of the muscle cells, resulting in a dilatory effect on the pulmonary arteries and arterioles. In contrast, in some instances, inhaled powder formulation of PDE5 inhibitors are expected to take a more direct route after deposition in the lumen of pulmonary airways, diffusing across the airway walls into the vascular smooth muscle cells where it acts on the PDE5 enzyme and may result in a dilatory effect on the pulmonary arteries and arterioles. Thus, in some instances, for example, in the context of pulmonary hypertension, the target area of the lung for powder delivery is the deep lung where the pulmonary vasculature has smooth muscle cells upon which the active agent can exert its pharmacological effects. In some instances, effective delivery to this area of the lung may require smaller aerodynamic particle size ranges (typically greater than 1 micron on average, for example, between 1-5 microns MMAD, or between about 1-3 microns MMAD) for the aerosolized active agent. In other instances, for example, in the context of cystic fibrosis, the target tissue is the airway epithelial (such as the ciliated airways), particularly those affected by defective CFTR protein. In some instances, effective delivery to this area of the lung may require aerodynamic particle size ranges of between about 1 to about 5 microns in aerodynamic diameter, about 2 to about 6 microns. or about 2 to about 7 microns. In some instances, the dry powder formulations provided in this disclosure have an MMAD in the appropriate size range for delivery to the deeper parts of the lung.

In some instances, pulmonary delivery with higher aerosolization efficiencies (such as, for example, about 70% FPF), may allow less mouth and throat deposition upon aerosolization and inhalation by a subject. As mouth and throat deposited drug is swallowed and will be absorbed similarly to orally administered formulation, reducing swallowing by achieving efficient aerosolization may reduce the incidence of systemic effects.

In certain instances, a delivered dose of about 0.25 mg to about 20 mg may be delivered to the subject upon aerosolization. For example, in some instances, typical doses for treatment of pulmonary hypertension will be about 0.5 mg to about 20 mg of active agent, depending on patient disease category, disease stage, and other health aspects of the subjects such as, for example, medication, patient age, etc. In some instances, the inhaled dose required to attain efficacy in a human subject with pulmonary hypertension delivered via a high efficiency inhaler device may be about 1/10th to 1/20th the oral dose, or 0.25 mg to 0.5 mg, possibly 0.1 mg to 3 mg of active agent delivered to the deep lung. In another example, in some instances, typical doses for treatment of cystic fibrosis will be about 0.5 mg to about 30 mg of active agent, depending on patient genetic factors (such as type of CTFR mutation), disease stage, and other health aspects of the subjects suhc as, for example, medication, patient age, etc. For example, in some instances, typical doses for treatment of myocardial diseases will be about 0.5 mg to about 20 mg of active agent, depending on patient disease category, disease stage, and other health aspects of the subjects such as, for example, medication, patient age, etc.

FIG. 16 is a block diagram illustrating methods of treating a disease in a mammal in need thereof according to some aspects. As shown in step 1801 of method 1800, a subject with a disease in need of treatment is provided. In one aspect, the disease may be a lung disease or a heart disease. For example, in some aspects, the lung disease may be pulmonary hypertension or cystic fibrosis. In other aspects, the heart disease may be congestive heart failure. As shown in step 1802, the method further includes administering to the subject via a pulmonary route an effective amount of a powder pharmaceutical composition comprising a) at least about 2% of a PDE5 inhibitor, or a pharmaceutically acceptable salt or ester thereof, by weight relative to the total weight of the overall pharmaceutical composition dose, and b) at least one pharmaceutically acceptable carrier. In some instances, the powder pharmaceutical composition may be administered as an aerosol. For example, in some cases, the powder pharmaceutical composition may be administered using a dry powder inhaler or a metered dose inhaler. For example, in some instances, the powder pharmaceutical composition may be administered by providing an inhaler comprising a dispersion chamber having an inlet and an outlet, the dispersion chamber containing an actuator that is movable reciprocatable along a longitudinal axis of the dispersion chamber; and inducing air flow through the outlet channel to cause air and the powder pharmaceutical composition to enter into the dispersion chamber from the inlet, and to cause the actuator to oscillate within the dispersion chamber to assist in dispersing the powder pharmaceutical composition from the outlet for delivery to a subject through the outlet.

The foregoing description of certain aspects and features, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. Certain features that are described in this specification in the context of separate embodiments can also be implemented in combination in a single implementation. Conversely, various features that are described in the context of a single implementation can also be implemented in multiple ways separately or in any suitable subcombination. Moreover, although features may be described above as acting in certain combinations, one or more features from a combination can in some cases be excised from the combination, and the combination may be directed to a subcombination or variation of a subcombination. Thus, particular embodiments have been described. Other embodiments are within the scope of the disclosure.

The following examples are intended for illustration only, are not intended to limit the scope of this disclosure. The contents of all U.S. patents and other references referred to in this application are hereby incorporated by reference herein in their entirety.

EXAMPLES

Example 1. Identification of Vardenafil Compounds

In view of the range of vardenafil forms, including salts and hydrates, as well as the limitation of conventional chemical identification methods, it is not straightforward to identify the form of vardenafil sold commercially or described in the art. For example, both anhydrous VarHCl (vardenafil hydrochloride) and $Var(HCl)_2$ (vardenafil dihydrochloride) can stoichiometrically obtain 1-3 bound water molecules to form hydrates. Among them, crystalline $VarHCl \cdot 3H_2O$ is the thermodynamically stable form that has been used in commercial formulations. However, VarHCl and $Var(HCl)_2$ can be difficult to differentiate from each other by each individual analytical method such as high performance liquid chromatography (HPLC), ultraviolet spectrophotometer (UV), mass spectroscopy (MS), Infra-red (IR), elemental analysis (CHN) and chloride ion analysis. For example, the molecular weight of $Var(HCl)_2 \cdot H_2O$ (579.55 g/mol) and $VarHCl \cdot 3H_2O$ (579.12 g/mol) are nearly identical. As such, differentiating between these molecules by any individual mass related analytical techniques reliably may not be possible. In fact, Applicants have found that several reputable chemical suppliers have mistakenly sold $Var(HCl)_2 \cdot xH_2O$ (vardenafil dihydrochloride hydrate) as $VarHCl \cdot 3H_2O$ (vardenafil hydrochloride trihydrate).

Testing methods were developed to ensure the ability to identify and differentiate the chemical identity of vardenafil forms for use in preparation of formulations. As described further below, the methods are: HPLC quantification coupled with Karl Fischer (KF) titration (Section A), elemental analysis (C, H, N) coupled with KF (Section B), NMR CH and $^{13}C$) (Section C), and pH titration assessment (Section D). For example, as shown below, these methods were used to differentiate $Var(HCl)_2 \cdot xH_2O$ and $VarHCl.xH_2O$.

A. HPLC Quantification Coupled with Karl Fischer (KF) Titration

While HPLC columns can be used to separate vardenafil compounds (active pharmaceutical ingredients; APIs) based on their polarity, this is not how HPLC was used to characterize the vardenafil compounds. The principle of this method is that the HPLC area under the curve (AUC) for the vardenafil portion of VarHCl and Var(HCl)$_2$ are the same as VarBase (488.61 g/mol) when the same mass of compounds are compared. The H$^+$ and Cl$^-$ ions in the vardenafil compounds will not be detected and reflected in AUC. Thus, when the same mass of the vardenafil compounds are weighed and analyzed by HPLC, the values of AUC quantified by HPLC will show VarBase>VarHCl >Var(HCl)$_2$ because part of the mass (H$^+$ and Cl$^-$) in VarHCl and Var(HCl)$_2$ will not contribute to the AUC, as shown below in Table 1. By comparing the AUC ratio of VarHCl/VarBase or Var(HCl)$_2$/VarBase, the number of HCl in vardenafil salts can be determined. Karl Fischer titration was performed using coulometric titration to determine trace amounts of water in the sample.

TABLE 1

Exemplary Vardenafil Forms and Theoretical Water Content

| Substance | MW (g/mol) | % VarBase | Water (%) |
|---|---|---|---|
| VarBase | 488.61 | 100.0 | 0 |
| VarHCl | 525.07 | 93.1 | 0 |
| VarHCl•H$_2$O | 543.09 | 90.0 | 3.32 |
| VarHCl•2H$_2$O | 561.10 | 87.1 | 6.42 |
| VarHCl•3H$_2$O | 579.12 | 84.4 | 9.33 |
| Var(HCl)$_2$ | 561.54 | 87.0 | 0 |
| Var(HCl)$_2$•H$_2$O | 579.55 | 84.3 | 3.11 |
| Var(HCl)$_2$•2H$_2$O | 597.57 | 81.8 | 6.03 |
| Var(HCl)$_2$•3H$_2$O | 615.59 | 79.4 | 8.78 |

There are four assumptions for applying this method:
1) All APIs are 100% pure.
2) The API dry weight (anhydrate VarHCl and Var(HCl)$_2$) is used for the mass calculation. This requires dehydration of raw material by heating in vacuo.
3) If there are any residual water contents (both unbound and bound water), they can be accurately quantified by KF.
4) The HPLC method (column, mobile phase, buffer, etc.) does not change throughout the testing.

HPLC analysis was performed using an Agilent 1260 Infinity series module HPLC system with appropriate columns and buffers (acidic aqueous and acidic organic mobile phases). The column temperature was maintained at 40° C. and the detection was monitored at a wavelength of 215 nm.

VarBase and a vardenafil salt hydrate (VarSalt) were purchased and analyzed using the above-described method. The results are shown in Table 2. Based on the dry weight and AUC, the amount of vardenafil in the salt is 87.2% of that in VarBase. This is consistent with the percent API of Var(HCl)$_2$, which is calculated to have a percent API of 87.1% as shown in Table 1 above. Thus, although the VarSalt was claimed to VarHCl.3H$_2$O, this analysis shows that the compound was actually Var(HCl)$_2$·xH$_2$O.

TABLE 2

HPLC + KF Analysis of VarSalt and VarBase

| | VarSalt | VarBase |
|---|---|---|
| API Weight (mg) | 3.002 | 3.008 |
| Water Content (%) | 3.485 | 1.658 |
| API Dry Weight (mg) | 2.897 | 2.958 |
| Diluent Volume (mL) | 20 | 20 |
| API Concentration (mcg/mL) | 144.9 | 147.9 |

TABLE 2-continued

HPLC + KF Analysis of VarSalt and VarBase

| | VarSalt | VarBase |
|---|---|---|
| AUC | 4707.8 | 5509.1 |
| AUC/mcg/mL | 32.5 | 37.2 |
| AUC/mcg/mL ratio (VarSalt/VarBase) | 0.872 | N/A |

B. Elemental Analysis of C, N, and H Coupled with Karl Fischer (KF) Titration

Elemental analysis can determine the mass fraction of carbon, hydrogen, nitrogen and other heteroatoms (generally referred to as CHNX). The most common elemental analysis accomplished by combustion analysis is for carbon, hydrogen, nitrogen, which is referred to herein as CHN analysis. Commercial VarSalt was purchased for this analysis. The amount of water in the vardenafil compound was also accurately determined by KF titration before the CHN analysis was performed to ensure accuracy. The elemental analysis showed a % C value of 45.88, a % H value of 5.92 and a % N value of 13.87, within an error margin of ±0.3%. The water content was measured using a coulometric KF titrator, and the result was 6.92%. Based on this analysis, the VarSalt appeared to have approximately 2 HCl molecules and 2 water molecules, indicating that the VarSalt was likely Var(HCl)$_2$·2H$_2$O (or possibly a mixture of dihydrate and trihydrate forms).

C. Nuclear Magnetic Resonance (NMR) ($^1$H and $^{13}$C)

VarHCl·3H$_2$O and Var(HCl)$_2$·xH$_2$O (VarHCl and Var (HCl)$_2$ in solution) have generally been deemed as indistinguishable using NMR. For example, U.S. Pat. No. 6,362,178 describes that the chemical shift for VarHCl.3H$_2$O (Example 20) and Var(HCl)$_2$·xH$_2$O (Example 337) are identical by $^1$H NMR, as set forth below.

200 MHz $^1$H-NMR (DMSO-d$_6$) 0.96, t, 3H; 1.22, t, 3H; 1.36, t, 3H, 1.82, sex, 2H; 2.61, s, 3H; 2.88, m, 2H; 3.08, m, 6H; 3.50, m, 2H; 3.70, m, 2H; 4:25, quart., 2H; 748, d, 1H; 7.95, m, 2H, 11.42, s, 1H; 12.45, s, 1H.

This is problematic because many vendors provide only the $^1$H NMR in the Certificate of Analysis for vardenafil and, thus, may not be correctly distinguishing between VarHCl.3H$_2$O and Var(HCl)$_2$·xH$_2$O.

To identify spectral characteristics that could be used to identify VarHCl·3H$_2$O and Var(HCl)$_2$·xH$_2$O, both $^1$H and $^{13}$C NMR were performed. The spectra are shown in FIG. 1. The results showed that VarHCl·3H$_2$O (top) and Var(HCl)$_2$·xH$_2$O (bottom) can be readily distinguished from NMR, using d$_6$-DMSO as solvent. For example, in the $^1$H NMR, a characteristic methyl peak showed a chemical shift of 2.472 ppm for VarHCl·3H$_2$O, while the same methyl peak shifted to 2.604 ppm for Var(HCl)$_2$·xH$_2$O. De-shielding causes a methyl group shift from 2.472 to 2.604. At around 8 ppm, two of the three protons in the benzene ring of vardenafil showed a triplet (doublet+singlet) for VarHCl·3H$_2$O, while the same protons showed a quintet (triplet+doublet) for Var(HCl)$_2$·xH$_2$O.

The result of $^{13}$C NMR clearly shows that the chemical shift of a large number of carbon signals at different ppm. Spectra for $^{13}$C NMR in d$_6$-DMSO analysis of Var(HCl)$_2$· xH$_2$O (top) and VarHCl·3H$_2$O (bottom) are shown in FIG. 2.

This is the first reporting of differences in the NMR spectrum of VarHCl·3H$_2$O and Var(HCl)$_2$·xH$_2$O. This method can be used, alone or in conjunction with other analytical methods to identify and characterize vardenafil compound preparations. For example, based on this analytical method, it is apparent that the vardenafil salt described in U.S. Pat. No. 6,362,178 (Example 20) is misidentified and is actually $Var(HCl)_2 \cdot xH_2O$.

D. pH Titration

Figure 3:
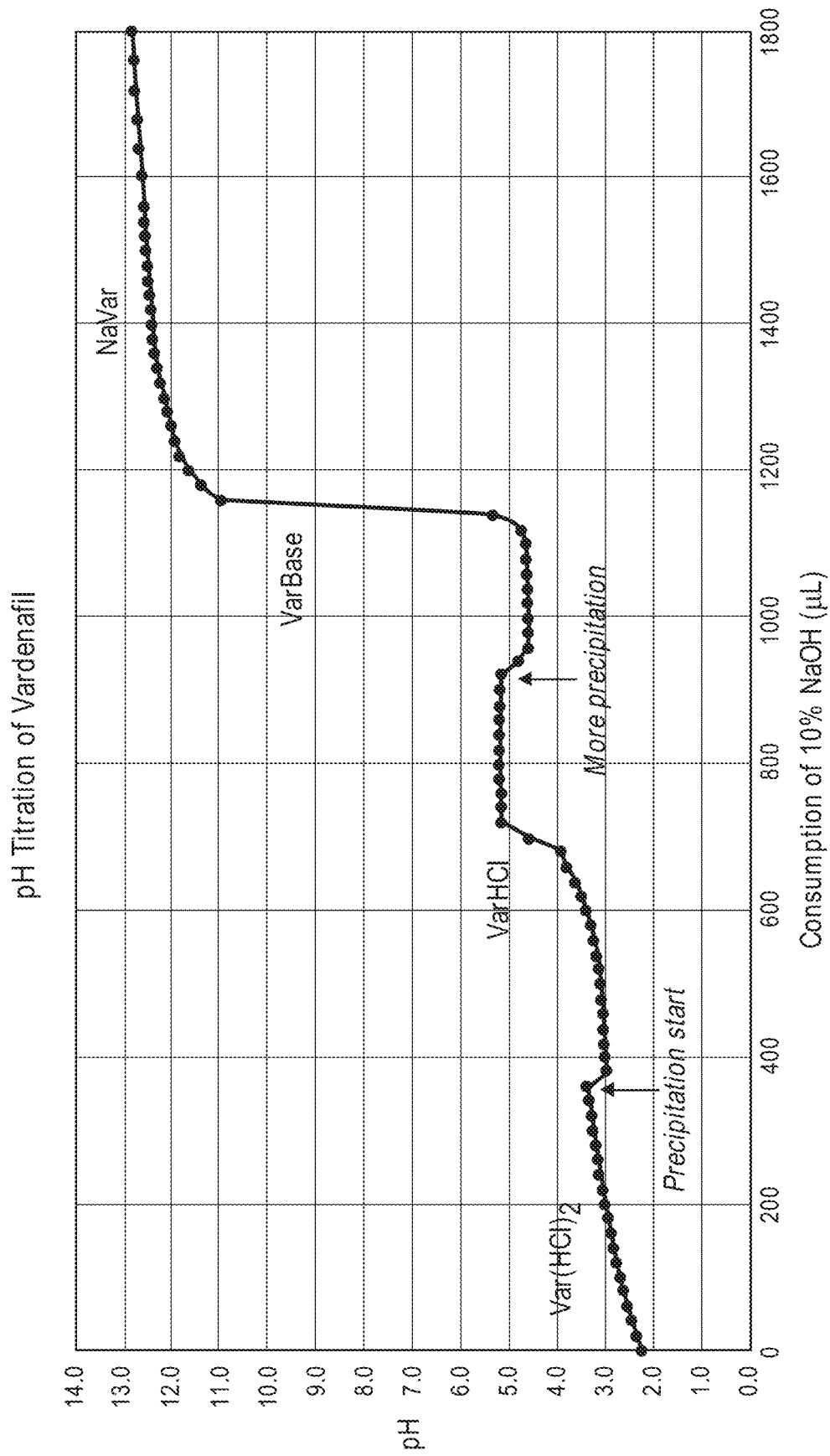
FIG. 3 illustrates the results of pH titration analysis for Var(HCl)$_2$, VarHCl, and VarBase according to some aspects.

Perhaps the easiest way to distinguish $Var(HCl)_2$, VarHCl, and VarBase is by means of pH titration analysis. The experiment was performed at ambient condition (22.5° C. and 31% RH). One gram of $Var(HCl)_2 \cdot xH_2O$ was dissolved in 15 mL pure $H_2O$ in a beaker. NaOH solution (10%) was added in 20 μL stepwise increments while the solution was stirred vigorously. The pH and temperature was recorded 20 sec after each addition of NaOH solution. The results of this analysis are shown in FIG. 3.

The result showed that the initial pH was 2.15 at 22.5° C. The pH increased slowly until precipitation appeared. The pH dropped accordingly when VarHCl was gradually precipitated from the solution until the pH reached 3.9. A rapid increase in pH was observed, indicating all VarHCl was precipitated. The pH reached a plateau at 5.2 and dropped to 4.6, indicating the conversion of VarHCl to VarBase. All VarBase was precipitated when a sharp change of pH occurred from 5.3 to 10.9. Continued addition of 10% NaOH resulted in the dissolution of all precipitate and the conversion of VarBase to the sodium salt of vardenafil (NaVar). Thus, in addition to being useful for chemical identification purposes, pH titration can also be used for the conversion and preparation of desired salt forms of vardenafil.

Example 2. Intrinsic Stability Assessment of Vardenafil Compounds

The intrinsic stability of vardenifil compounds can be assessed to aid in identification of suitable conditions for preparation of pharmaceutically acceptable formulations. Characterization of the degradation pathways for vardenafil compounds provides information useful to the development of pharmaceutically acceptable formulations for long term storage. Described below are exemplary experiments relating to characterization of $VarHCl \cdot 3H_2O$.

Materials: $VarHCl \cdot 3H_2O$, HPLC grade water, 36.5% HCl, NaOH pellets, 6% $H_2O_2$ were all purchased. 1N HCl and 1N NaOH were prepared in house.

Method: $VarHCl \cdot 3H_2O$, HPLC grade water, 36.5% HCl, NaOH pellets, 6% $H_2O_2$ were all purchased, and 1N HCl and 1N NaOH were prepared in house. Intrinsic stability testing was performed according to International Conference on Harmonization (ICH) Guidance for Industry Q1A(R2) Stability Testing of New Drug Substances and Products (November 2003, Rev. 2). Briefly, the compound was tested for acid hydrolysis (1N HCl) and base hydrolysis (1N NaOH) at r.t. for 48 hr and at 60° C. for 4 hr. Oxidation assessment (6% $H_2O_2$) was performed at r.t. for 48 hr. The stability of $VarHCl.3H_2O$ in solution was assessed using HPLC analysis as described above in Example 1, Section A.

Starting material (control): The HPLC trace for the starting material showed single peak as expected ($R_T$=6.050 min; Area %=100). See FIG. 4A.

Figure 4A:
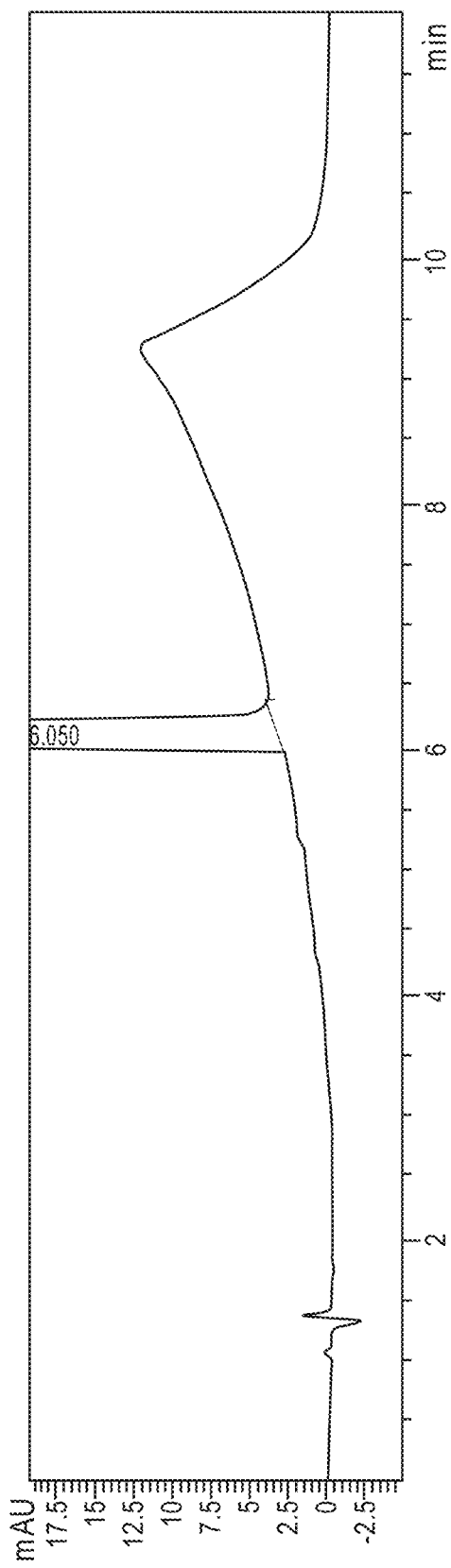
FIGS. 4A-4F illustrates the results of instrinsic stability testing of VarHCl·3H$_2$O as assessed by a HPLC high performance liquid chromatography (HPLC) according to certain aspects.
Figure 4B:
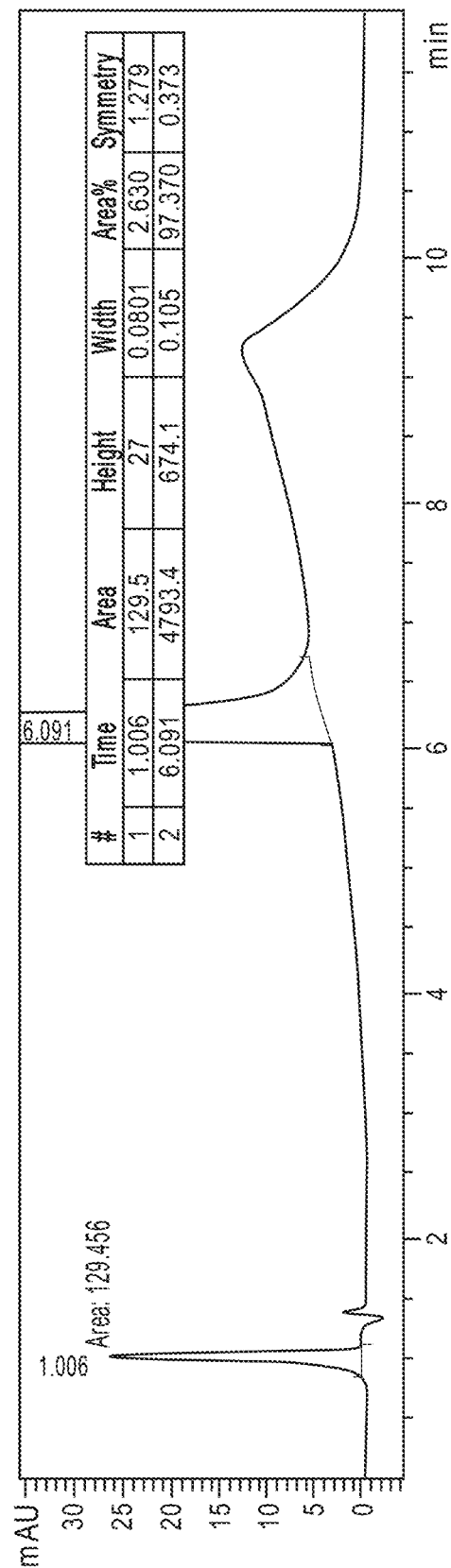
Figure 4C:
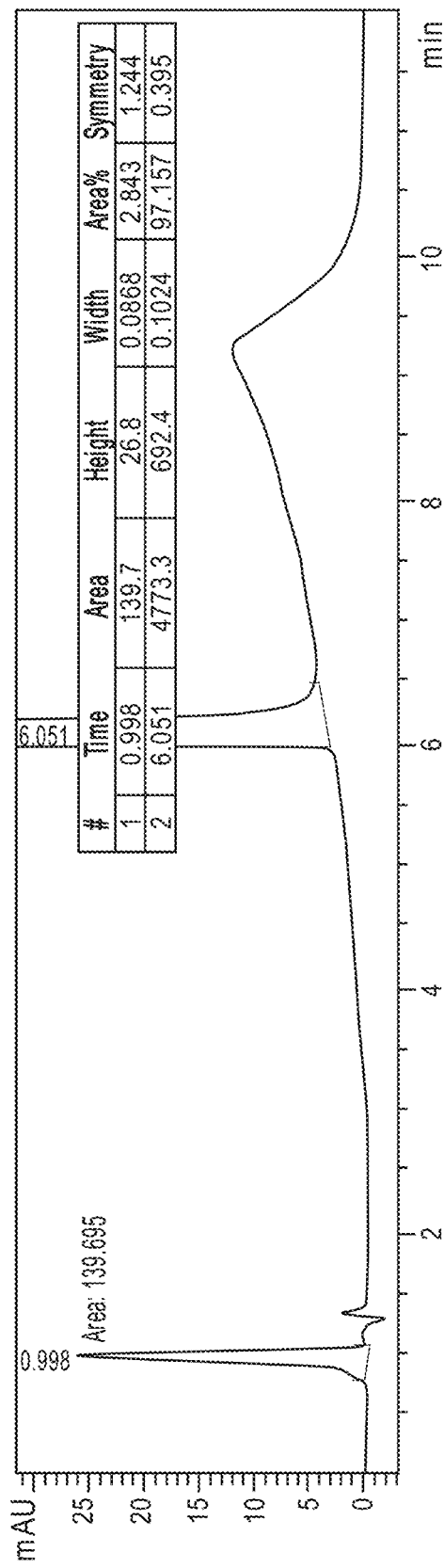

Degradation in acidic solution: In 1N HCl at r.t. after 48 hr, a single degradation peak ($R_T$=1.006 min; Area %=2.630) was observed. A similar degradation peak was observed in 1N HCl at 60° C. for four hours ($R_T$=0.998 min; Area %=2.843). The degree of degradation was comparable in both acidic conditions. The HPLC traces for these experiments are shown in FIG. 4B (48 hr at r.t.) and FIG. 4C (4 hr at 60° C.).

Figure 4D:
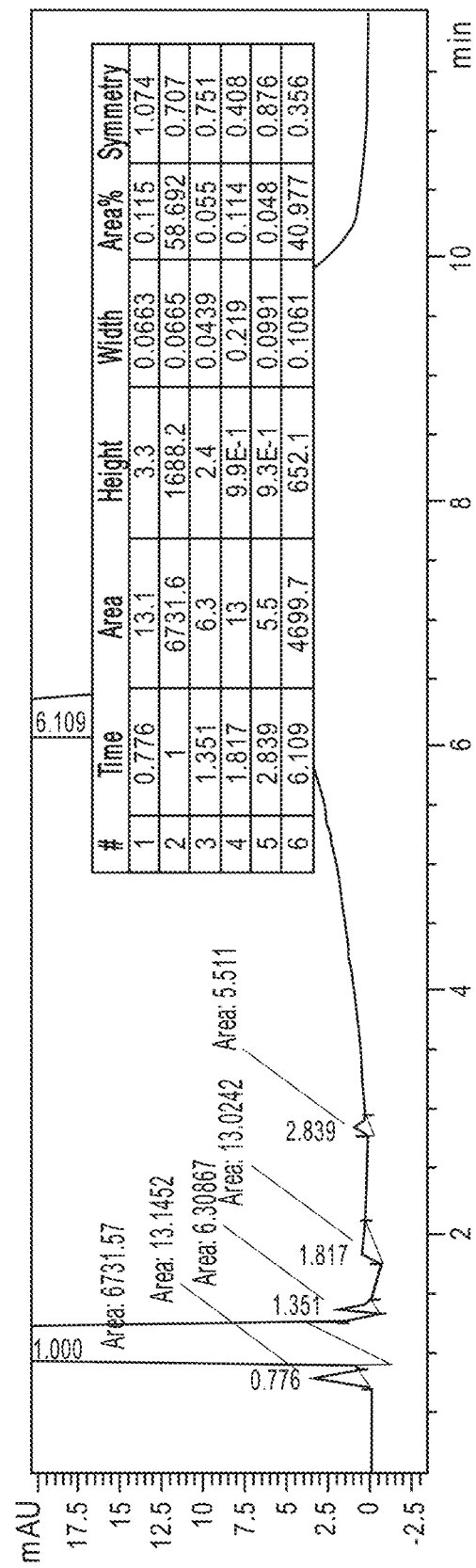
Figure 4E:
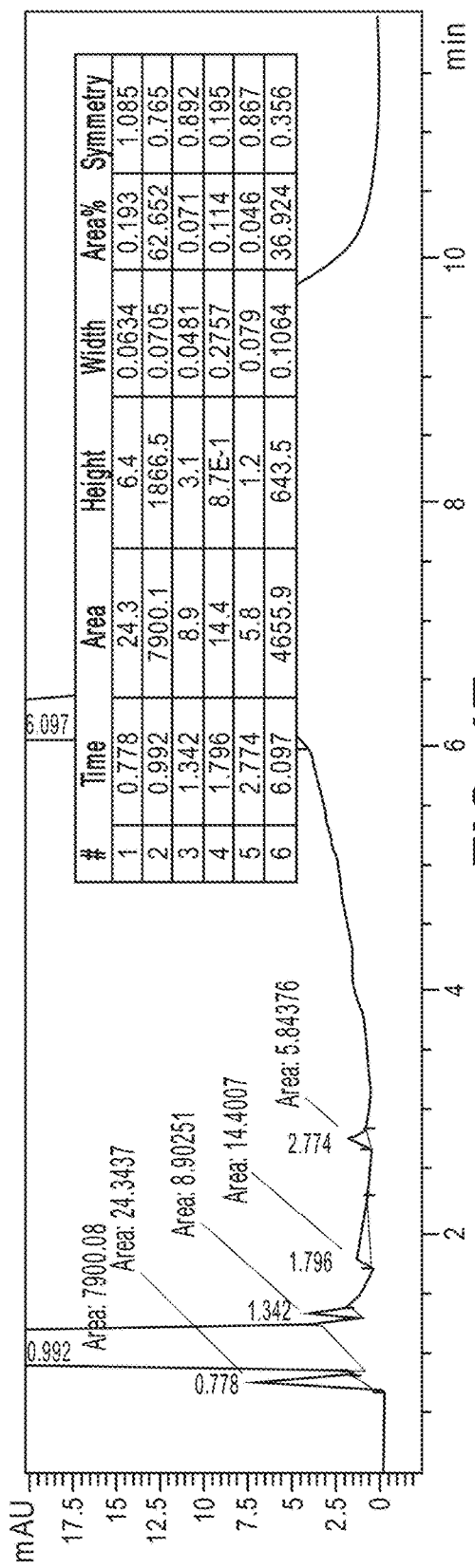

Degradation in basic solution: In 1N NaOH at r.t. after 48 hr, a major degradation peak ($R_{T1}$=1.000 min; Area %=58.692) was observed and corresponded with four additional small degradation peaks ($R_{T2}$=0.776; Area %=0.1115; $R_{T3}$=1.351; Area %=0.055; $R_{T4}$=2.839; Area %=0.048). When exposed in 1N NaOH 60° C. condition for 4 hrs, a similar degradation pattern was observed: a major degradation peak ($R_{T1}$=0.992 min; Area %=62.652) and corresponded with four additional small degradation peaks ($R_{T2}$=0.778; Area %=0.193; $R_{T3}$=1.342; Area %=0.071; $R_{T4}$=2.774; Area %=0.046). The HPLC traces for these experiments are shown in FIG. 4D (48 hr at r.t.) and FIG. 4E (4 hr at 60° C.).

Figure 4F:
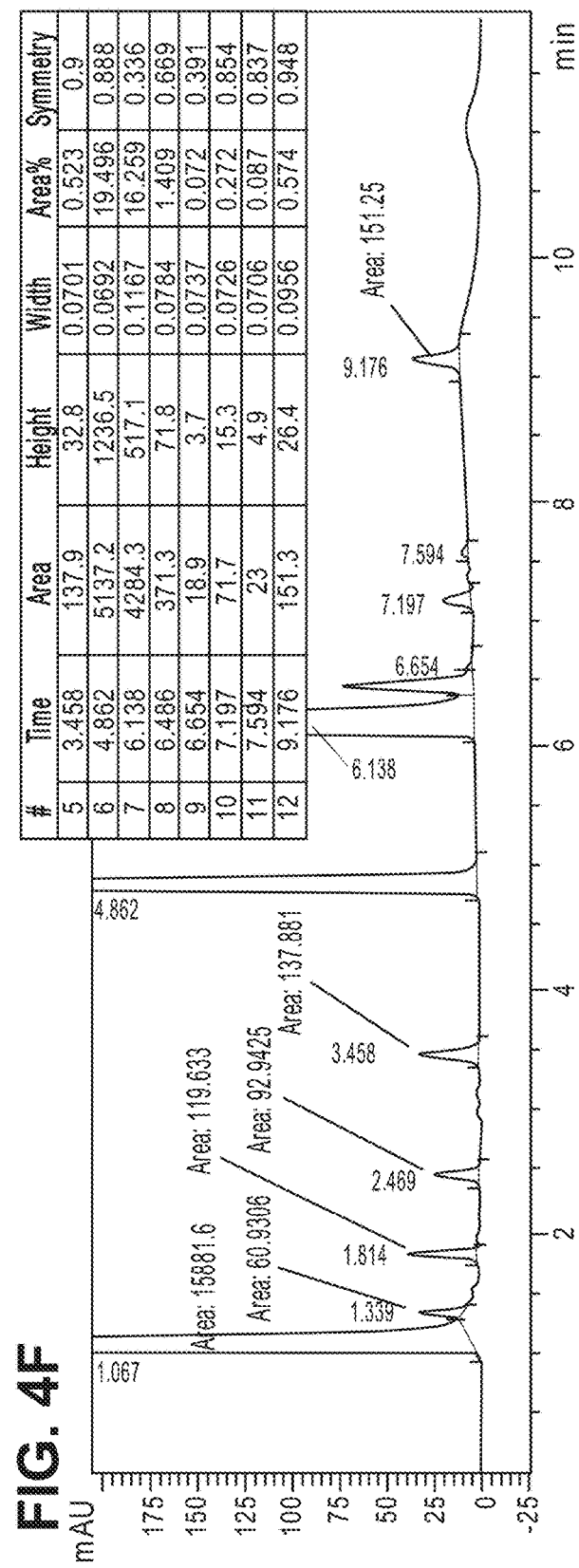

Degradation in oxidative solution: In 6% $H_2O_2$ at r.t. for 48 hr, there were two major and eight minor degradation peaks. The two major peaks were at $R_{T1}$=1.067 min; Area %=60.270 and $R_{T2}$=4.862 min; Area %=19.496. The eight minor peaks were at $R_{T3}$=1.339 min; Area %=0.231; $R_{T4}$=1.814 min; Area %=0.454; $R_{T5}$=2.469 min; Area %=0.353; $R_{T6}$=3.458 min; Area %=0.523; $R_{T7}$=6.486 min; Area %=1.409; $R_{T8}$=7.197 min; Area %=0.272; $R_{T9}$=7.594 min; Area %=0.087; $R_{T10}$=9.176 min; Area %=0.574. The HPLC traces for these experiments are shown in FIG. 4F.

These studies showed that $VarHCl \cdot 3H_2O$ demonstrated degradation in acidic, basic, and oxidative conditions per ICH Guidance. The extent of degradation was significant in basic and oxidative conditions, which is understandable because the sulfonamide group in $VarHCl \cdot 3H_2O$ is susceptible to hydrolysis, particularly in basic condition. The tertiary amine group may easily form amine oxide in oxidative condition and the amine oxide may undergo further degradation via a host of chemical reactions. These observations differ from literature reports on the degradation of $VarHCl \cdot 3H_2O$ (Rao et al, Chromatographia 2008, 68, 829-835, showing less extensive degradation in basic conditions). Similarly, it is expected that VarBase could also be oxidized more easily when the free tertiary amine is presented in the molecule.

The observed degradation patterns of $VarHCl \cdot 3H_2O$ in aqueous solution suggest that the development of a dry powder aerosol formulation may be desirable to maintain chemical stability of the compound. As noted above, no dry powder aerosol formulations of vardenafil compounds have been developed to date.

Example 3. Excipient Compatability Assessment of Vardenafil Compounds

Studies were performed to assess the chemical compatibility/stability of vardenafil compounds with excipients. The testing of vardenafil compounds with one or more pharmaceutically acceptable excipients/carriers is an aspect of developing a pharmaceutically-acceptable, stable, carrier-based vardenafil formulation. One of the most frequently used excipients for dry powder aerosol formulation is lactose. However, lactose is a reducing sugar. Vardenafil contains amine groups that could react with lactose via the Maillard reaction. In the absence of prior studies assessing the vardenafil and reducing sugar compatibility, the following experiments were performed to assess if lactose could be used to prepare a stable vardenafil blend formulation.

A. Materials and Methods $Var(HCl)_2 \cdot xH_2O$ and VarBase were purchased, and $VarHCl \cdot 3H_2O$ was prepared in house using $Var(HCl)_2 \cdot xH_2O$. Conversion of $Var(HCl)_2 \cdot xH_2O$ to $VarHCl \cdot 3H_2O$ was performed by the pH titration described above in Example 1, Section D. $Var(HCl)_2 \cdot xH_2O$ was used in micronized form (prepared using a commercial dry jet-miller) as described in Example 4. VarBase and VarHCl·3H$_2$O were not micronized. Respitose® ML006 ("ML006") (DMV-Fonterra Excipients), an inhalation grade lactose, was also purchased.

Blending ratios were selected based on powder surface area to ensure sufficient contact between API and excipient. The following blends were made: Var(HCl)$_2$·xH$_2$O: ML006 (1:9), VarBase: ML006 (1:1) and VarHCl·3H$_2$O: ML006 (1:1). Blends were prepared by geometric dilution preblending by hand, followed by mixing using a commercially available laboratory shaker-mixer. Where enclosed, blends were pouched using foil to prevent moisture ingress into the powder mixture.

Saturated NaCl and NaBr salt solutions were added separately to two desiccators to create equilibrium relative humidity of 75% at 40° C. and 60% at 25° C. (as described in Greenspan, J. Res. Natl. Bureau Std. —A, Phy Chem 1977, 81A (1), 89-96). Prior to use, the stability chambers were stored in incubators at preset temperature for at least 24 hr.

Samples were (1) pouched and stored at 25° C. and 60% relative humidity (RH), (2) pouched and stored at 40° C. and 75% RH, and (3) unpouched (exposed to ambient environment) at 40° C. and 75% RH. Samples were assessed for degradation by HPLC, as described above. Analysis was completed for the following time points: Var(HCl)$_2$·xH$_2$O blend at six month, VarBase blend at three months, and VarHCl·3H$_2$O blend at one month.

B. Results

Figure 5C:
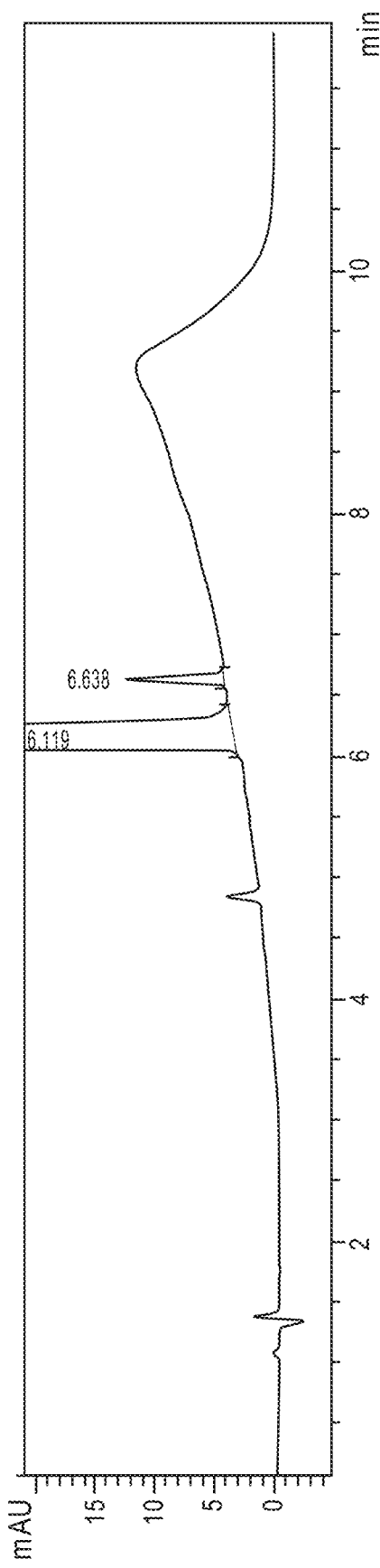
Figure 5D:
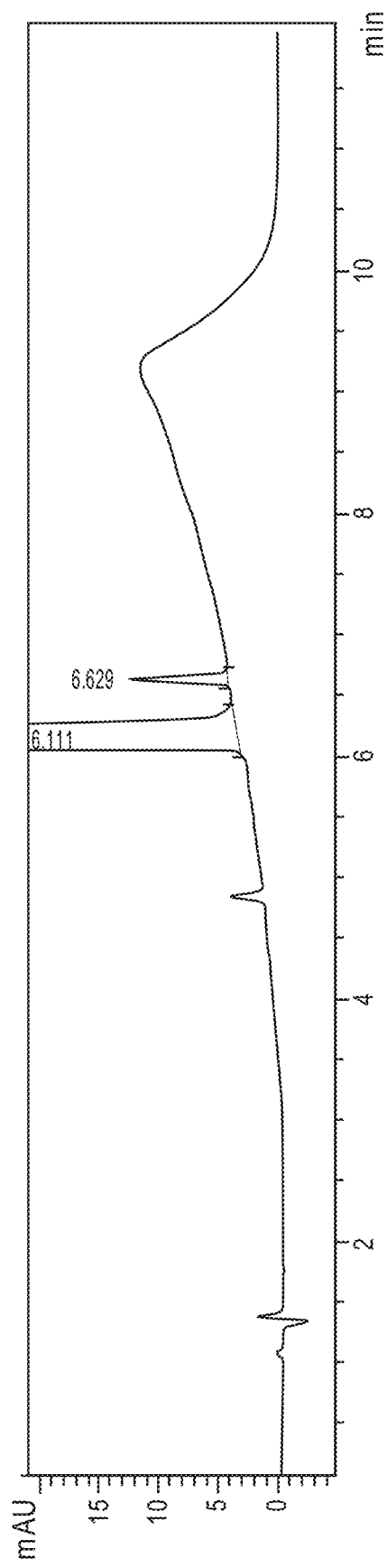

None of the samples showed chemical degradation products at any of the time points. Exemplary HPLC traces for the VarHCl·3H$_2$O blend at one month are shown in FIG. 5A (25/60 pouched), FIG. 5B (40/75 pouched), FIG. 5C (40/75 open), and FIG. 5D (VarHCl.3H$_2$O control). These results establish the stability of vardenafil-lactose blends as vardenafil was found to not undergo degradation when mixed with lactose under stable or accelerated conditions. This analysis is the first reporting that lactose appears to be an acceptable excipient for the preparation of vardenafil solid dosage forms.

Example 4. Particle Size Distribution of Micronized Vardenafil Compounds

Particle size of a dry powder aerosol formulation for administration by inhalation is closely linked to the deposition profile in the airways. Thus, a narrow size distribution allows better targeting of the aerosol. The median respirable particle size range is 0.5 to 5 microns, and more preferably 1-2 microns.

Var(HCl)$_2$·xH$_2$O, VarBase, and VarHCl·3H$_2$O were purchased and then micronized using a commercial dry jet-miller. The jet milling was achieved using typical jet milling conditions and a single milling process. As shown in Example 5, micronization leads to partial dehydration of VarHCl·3H$_2$O. As such, following micronization and absent rehydration, the compound is designated as VarHCl·xH$_2$O.

The APIs were dispersed in mineral spirit, and particle size analysis was performed by laser diffraction using a Microtrac X100 Particle Size Analyzer. Particle size span was calculated as $$\text{span} = \frac{D_{v0.9} - D_{v0.1}}{D_{v0.5}}$$

where $D_{v0.1}$, $D_{v0.5}$ and $D_{v0.9}$ are 10%, 50% and 90% of the volume size distributed below the respective values.

Figure 6A:
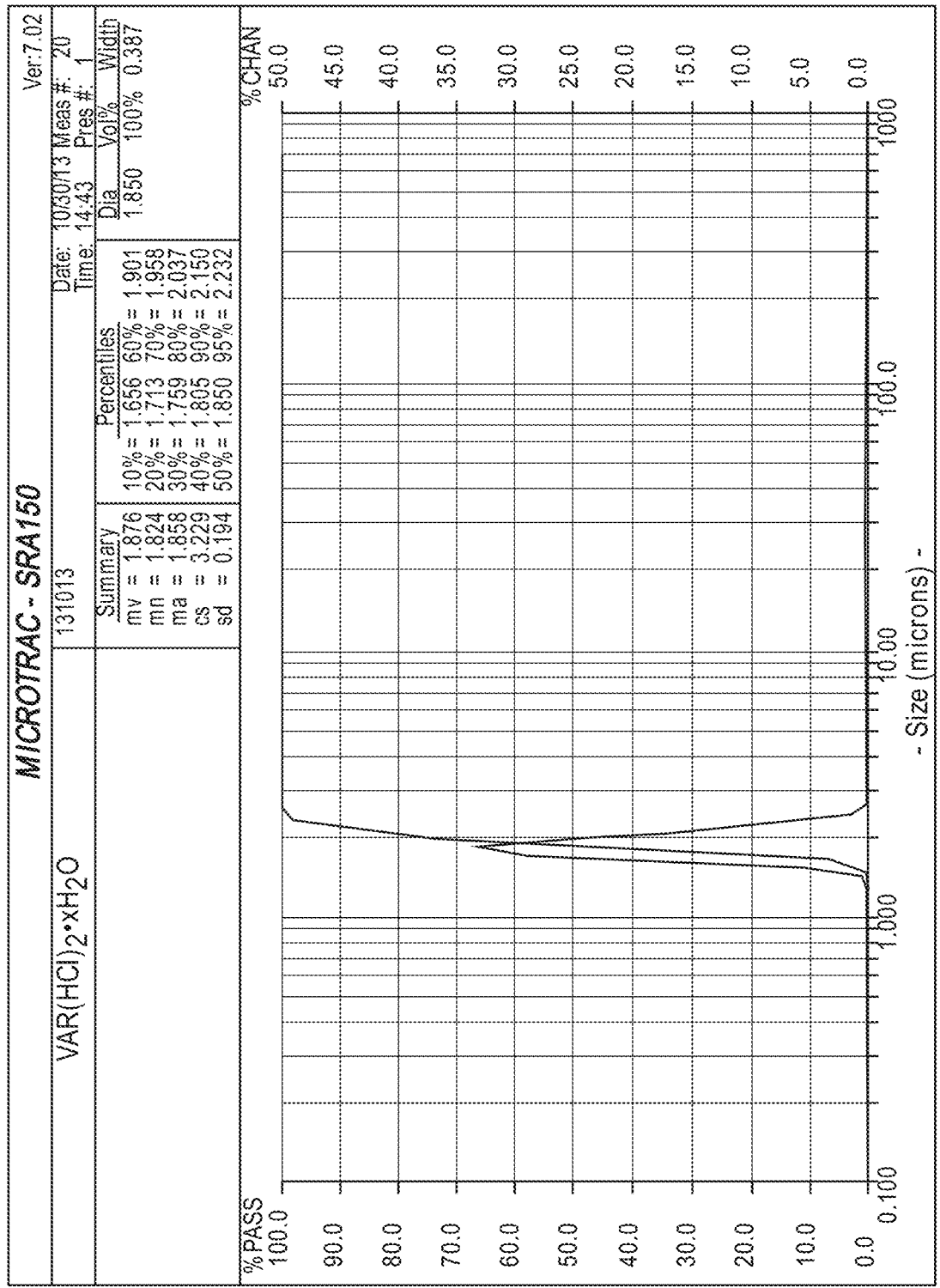
FIGS. 6A-6C illustrates the particle size distribution of micronized Var(HCl)$_2$·xH$_2$O, VarBase, and VarHCl·xH$_2$O, respectively, according to certain aspects.
Figure 6B:
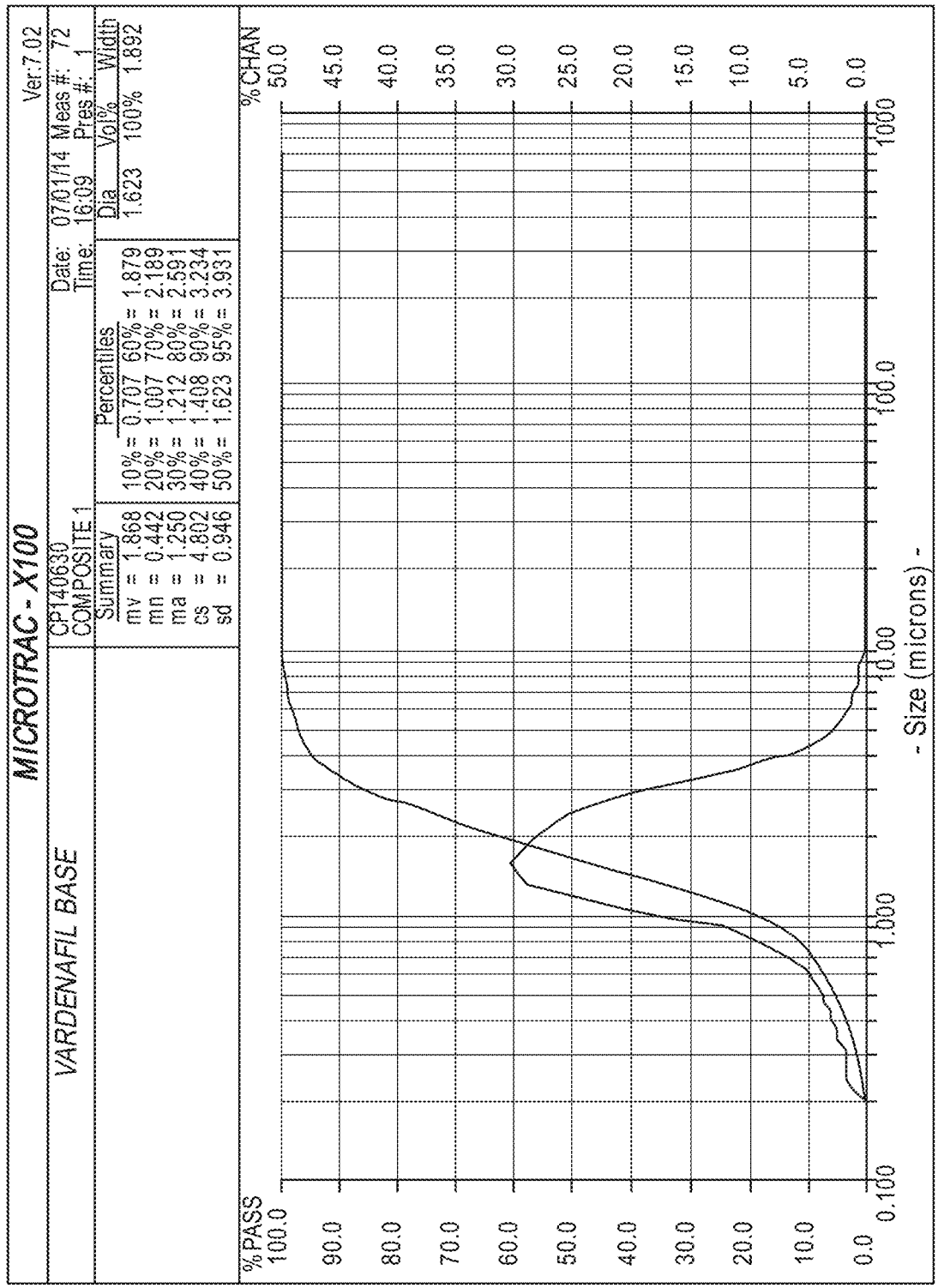
Figure 6C:
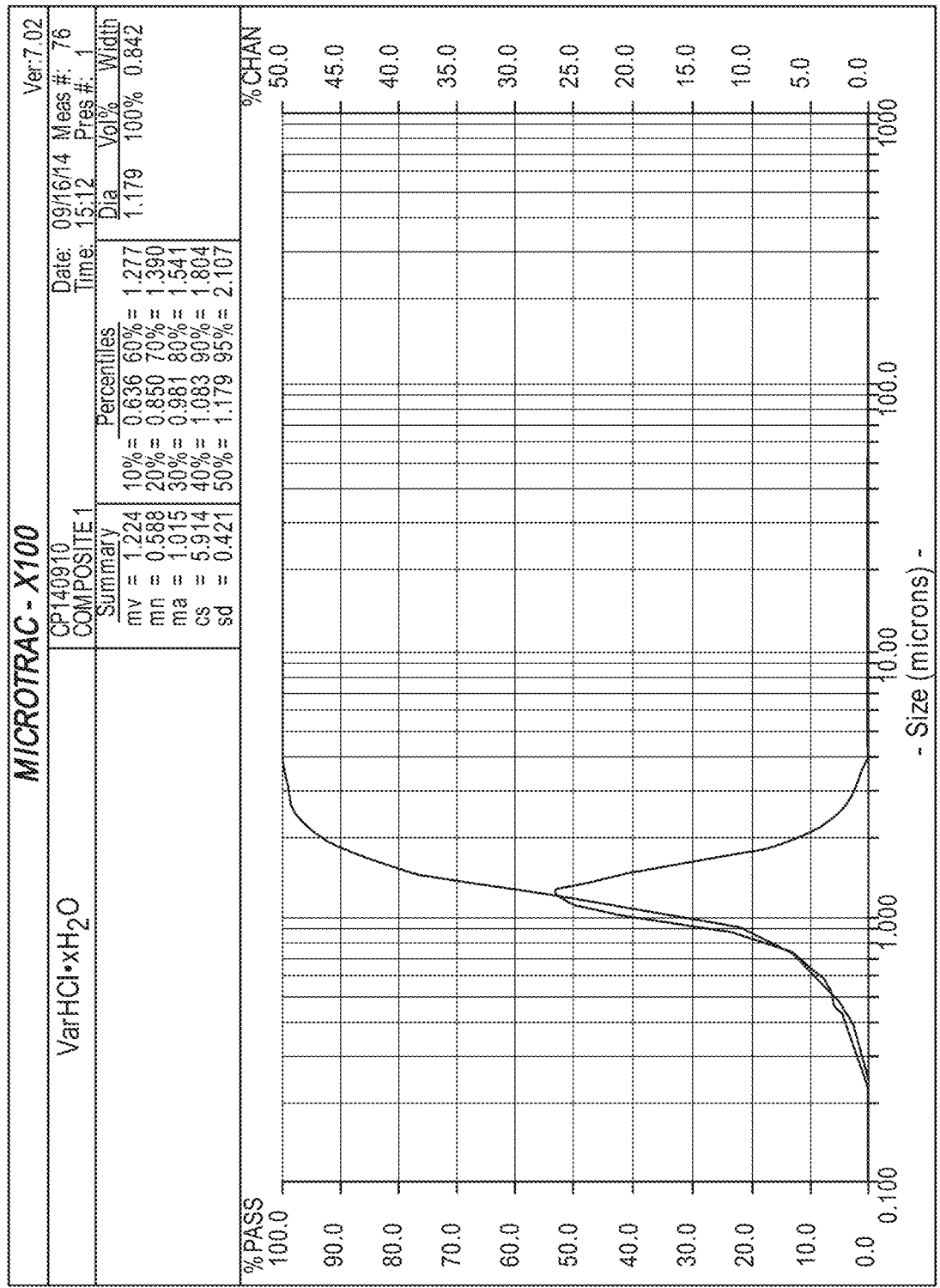

The particle size distributions of the micronized APIs are shown in FIG. 6A (Var(HCl)$_2$·xH$_2$O), FIG. 6B (VarBase), and FIG. 6C (VarHCl·xH$_2$O) and summarized in the Table 3 below. All three APIs were easily micronized into respirable size range. The particle size distributions were surprisingly narrow with spans less than 1.6 (VarHCl·xH$_2$O-0.99, Var (HCl)$_2$·xH$_2$O-0.27, VarBase—1.557). These experiments demonstrate that vardenafil compounds can be micronized to achieve a desirable median respirable particle size range with a narrow size distribution. Thus, dry powder formulations of vardenafil may be particularly suited for aerosol administration via inhalation.

TABLE 3

| Particle Size Distribution | | |
|---|---|---|
| Compound | $D_{V50}$ | Span |
| VarHCl•xH$_2$O | 1.179 | 0.99 |
| Var(HCl)$_2$•xH$_2$O | 1.85 | 0.267 |
| VarBase | 1.557 | 1.557 |

Figure 7A:
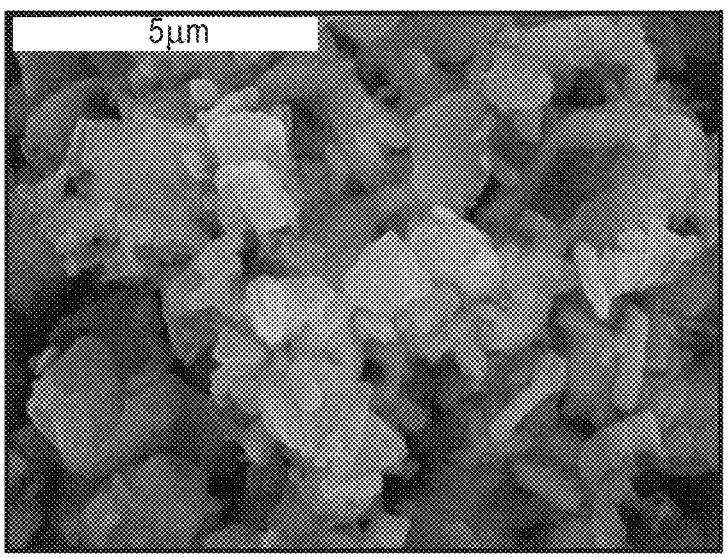
FIGS. 7A-7C provide scanning electron microscopy (SEM) images of micronized Var(HCl)$_2$·xH$_2$O, VarBase, and VarHCl·xH$_2$O, respectively, according to certain aspects.
Figure 7B:
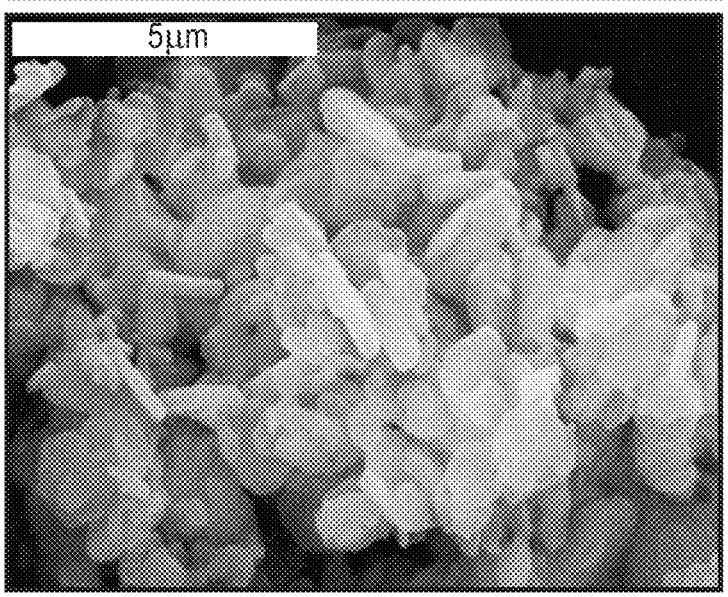
Figure 7C:
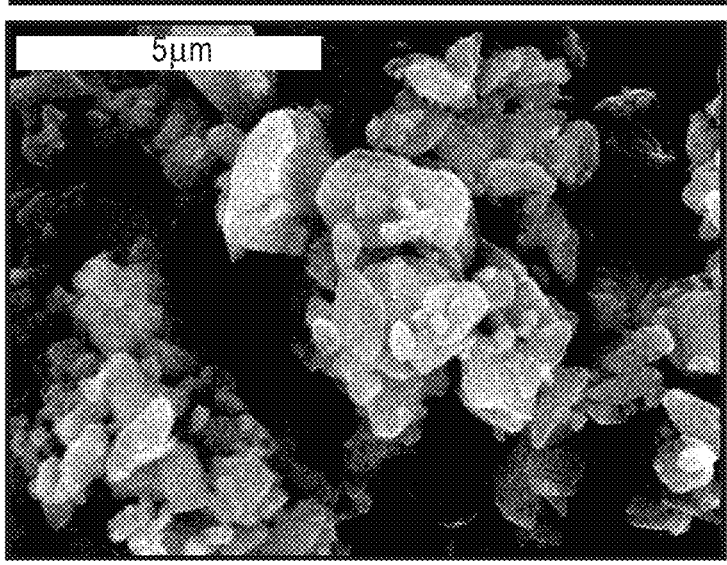

Scanning electron microscopy (SEM) imaging of the micronized APIs are shown in FIG. 7A (Var(HCl)$_2$·xH$_2$O), FIG. 7B (VarBase), and FIG. 7C (VarHCl·xH$_2$O). The powder was placed on the SEM stub and sputter coated with Pd—Au. Particle size distribution shown in SEM matches the laser diffraction data. The particles form aggregates which are typical for micronized powders via jet-milling.

Example 5. Physicochemical Characterization of Vardenafil Compounds

Several additional methods were used to characterize vardenafil compounds, including differential scanning calorimetry (DSC), thermogravimetric analysis (TGA), dynamic vapor sorption (DVS), and x-ray powder diffraction (XRPD). These analytical methods can be used to confirm identification of the vardenafil compound and assist with formulation development.

A. Material and Methods

APIs: Micronized Var(HCl)$_2$·xH$_2$O, VarBase, and VarHCl·xH$_2$O as described in Example 4 were characterized in these studies.

DSC Analysis: Compounds were deposited in non-hermetic crimped aluminum pan. Thermal properties were assessed using a Q2000 Modulated DSC (TA Instrument, New Castle, Del.). Method: scanning rate 10° C./min from 0-350° C.; heating; equilibrate at 0° C. for 4 min; modulation ±0.796° C./min.

DVS Analysis: No DVS results of these APIs have been previously reported. Moisture sorption and desorption behavior was assessed using a DVS-Advantage 1 (Surface Measurement Systems, Allentown, Pa.). Experimental parameters: sample % P/P$_0$ in a range of 0-80; 5% P/P$_0$ increment, equilibrium criteria, both sorption and desorption. Experiments conducted at 20° C.

XRPD Analysis: XRPD was performed for crystallinity and polymorphic form identification. Experimental parameters: 2° 2Theta range from 3-40 degree, 1° 2Theta degree/min. Experiments conducted at room temperature (ambient).

TGA Analysis: TGA was performed on micronized Var (HCl)$_2$·xH$_2$O to assess weight loss on heating. Active agent mass was monitored as it was exposed to a temperature program in a controlled atmosphere. Experimental parameters: scanning rate at 10° C./min, and temperature ranges from 40-280° C.

B. Results

The results for each of $Var(HCl)_2 \cdot xH_2O$, VarBase, and $VarHCl \cdot xH_2O$ using each of these methods are described below.

1. $Var(HCl)_2 \cdot xH_2O$

DSC of micronized $Var(HCl)_2 \cdot xH_2O$ is shown in FIG. 8A. $Var(HCl)_2 \cdot xH_2O$ exhibited an onset of glass transition $T_g$ ~50° C. that ended at ~110° C. This suggests that the high energy jet-milling process introduced amorphous content in the powder. A small endothermic peak was observed at ~140° C. that overlapped with the glass transition. This indicates that some trihydrate form was present and underwent partial water loss. Two large endothermic peaks were also observed at 222° C. and at 294° C. The former was the heat of fusion $T_m$. The nature of the latter is still under investigation. The result is similar to the DSC of $Var(HCl)_2 \cdot 3H_2O$ shown in U.S. Pat. No. 7,977,478 (FIG. 15) but covered a larger temperature range.

Figure 9A:
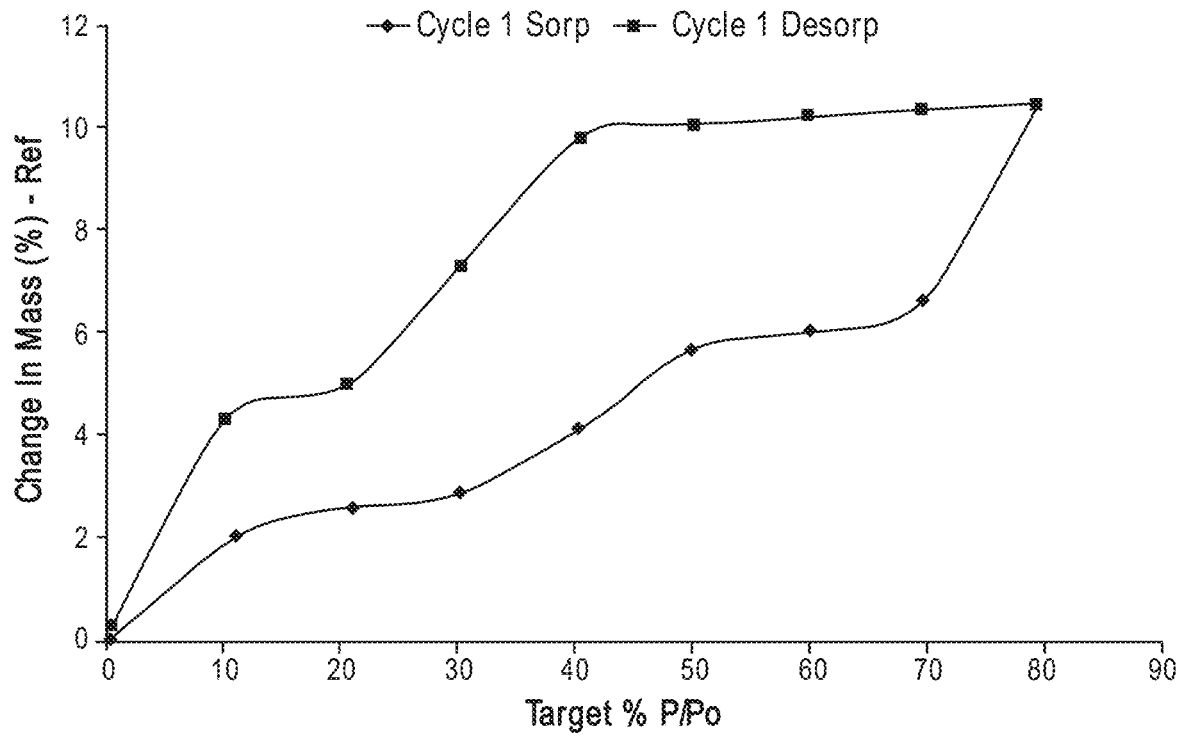
FIGS. 9A-9D illustrate dynamic vapor sorption (DVS) analysis of micronized vardenafil compounds to assess moisture sorption and desorption behavior according to certain aspects.

DVS of micronized $Var(HCl)_2 \cdot xH_2O$ is shown in FIG. 9A. A critical relative humidity was shown at 70% in sorption and 40% in desorption. In sorption phase, there were two step inflection points that occurred around 30% RH and 70% RH. The first may be a glass transition from amorphous to crystalline, and the second may reflect the formation of trihydrate. The desorption phase indicated that the trihydrate form is only stable in a short humidity range of 50% RH-80% RH. It is possible that, when RH is below 40% RH, loss of bound water may occur. Another desorption inflection point occurred around 20% RH. This suggests that $Var(HCl)_2 \cdot xH_2O$ is unstable in normal ambient condition and tends to lose bound water. A large hysteresis loop was observed due to the hydration of $Var(HCl)_2$.

Figure 16:
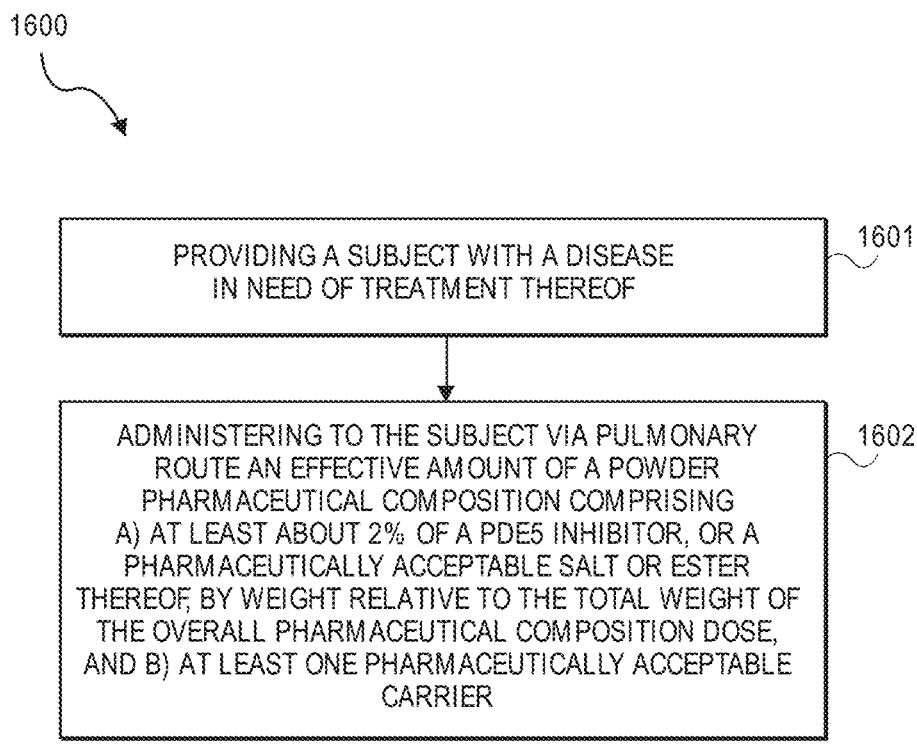

TGA of micronized $Var(HCl)_2 \cdot xH_2O$ is shown in FIG. 10. Based on the observed tilted curve, $Var(HCl)_2 \cdot xH_2O$ started to continuously lose water above 40° C. There was a transition at around 220° C. to 240° C. This could be the melting phase when the TGA result was combined with DSC thermogram. Another two transitions (inflection points) occurred around 80° C. and 130° C. The water loss upon heating profile is comparable to that described in U.S. Pat. No. 7,977,478 (FIG. 16).

XRPD of micronized $Var(HCl)_2 \cdot xH_2O$ is shown in FIG. 11A. The XRPD of $Var(HCl)_2 \cdot xH_2O$ (x=1, 2, or 3) were previously described in U.S. Pat. No. 7,977,478. The peaks of the micronized $Var(HCl)_2 \cdot xH_2O$ preparation were compared to those illustrated in that reference, which indicates that the $Var(HCl)_2 \cdot xH_2O$ preparation is likely a monohydrate and dihydrate mixture.

2. VarBase

DSC of micronized VarBase is shown in FIG. 8B. The VarBase preparation showed a sharp endothermic peak indicating heat of fusion $T_m$=190° C. The onset temperature was at ~177° C. when DSC scanning rate was set at 10° C./min. When the temperature increased above 250° C., decomposition peaks were observed. VarBase has two polymorphic forms: Form I and Form II. The Form II polymorph was previously determined to have a heat of fusion $T_m$=194° C. (U.S. Pat. No. 7,977,478), which is higher than the $T_m$ determined by this analysis. Thus, based on $T_m$, this VarBase preparation appeared to be the Form I polymorph. The Form I polymorph had previously been characterized by XRPD (WO/2011/079935). The XRPD analysis of the VarBase preparation confirmed that it is the Form I polymorph.

Figure 9B:
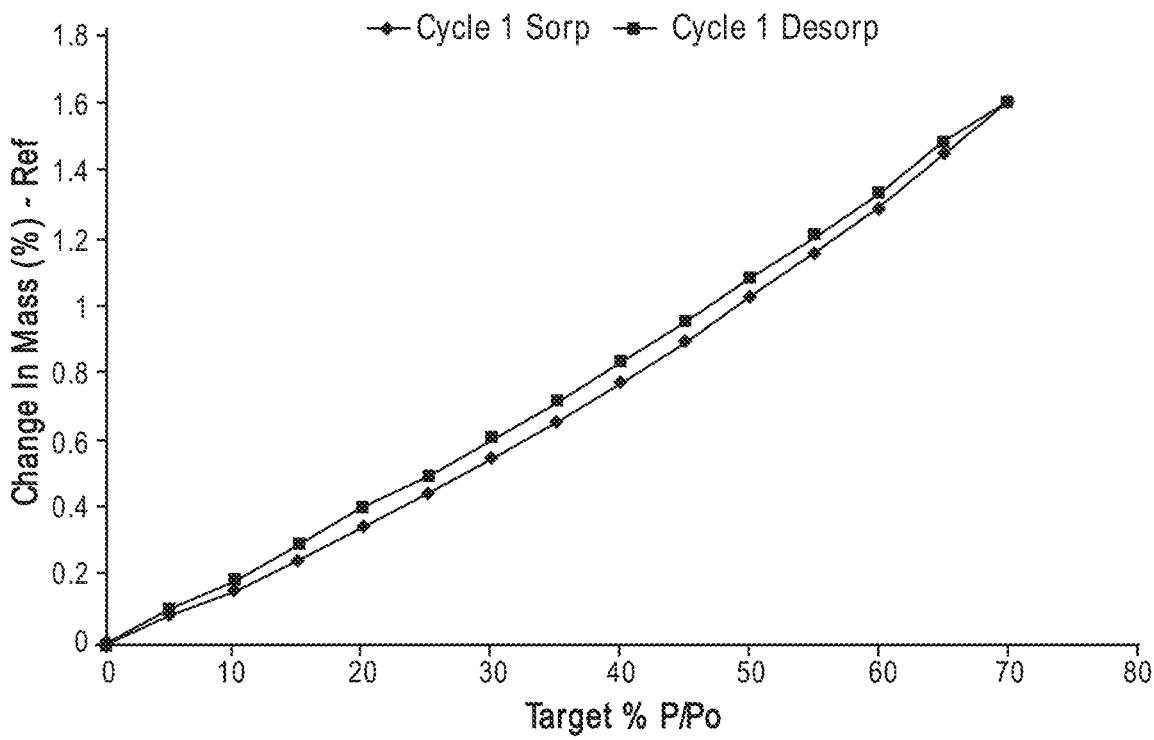

DVS of micronized VarBase is shown in FIG. 9B. The VarBase preparation sorption and desorption phases are much simpler as compared to $Var(HCl)2$ and VarHCl and their hydration forms, likely because VarBase cannot form hydrates and, thus, cannot for pseudopolymorphs. No obvious hysteresis loop was observed indicating that no hydration occurred. Some minor phase change was observed. This may be due to a small amount of amorphous content in the preparation caused by mechanical stress during jet-milling.

XRPD of micronized VarBase is shown in FIG. 11B. The comparison of 2θ values and % intensity with the crystalline Form I and Form II of VarBase revealed that the VarBase preparation is mainly crystalline Form I. The 2θ values of the major intensity peaks are: 9.8, 11.2, 12.4, 14.2, 15.3, 16.2, 17.1, 18.0, 20.1, 21.6, 23.2, 24.6, 27.3 degree. This result is in good agreement with DSC result.

3. $VarHCl \cdot xH_2O$

As noted above, $VarHCl \cdot 3H_2O$ is thermodynamically stable. However, under certain conditions (such as micronization), partial dehydration can occur. This is illustrated in the results described below.

DSC of micronized $VarHCl \cdot xH_2O$ is shown in FIG. 8C. $VarHCl \cdot xH_2O$ had a large endothermic peak at 107° C. showing the loss of bound water. The onset temperature was about 50~60° C. This indicates that $VarHCl \cdot xH_2O$ could be susceptible to elevated temperature above 50~60° C. The heat of fusion $T_m$ was 199.2° C. Above the heat of fusion temperature, the material quickly underwent decomposition. This is the first reporting of DSC analysis of micronized $VarHCl \cdot xH_2O$.

Figure 9C:
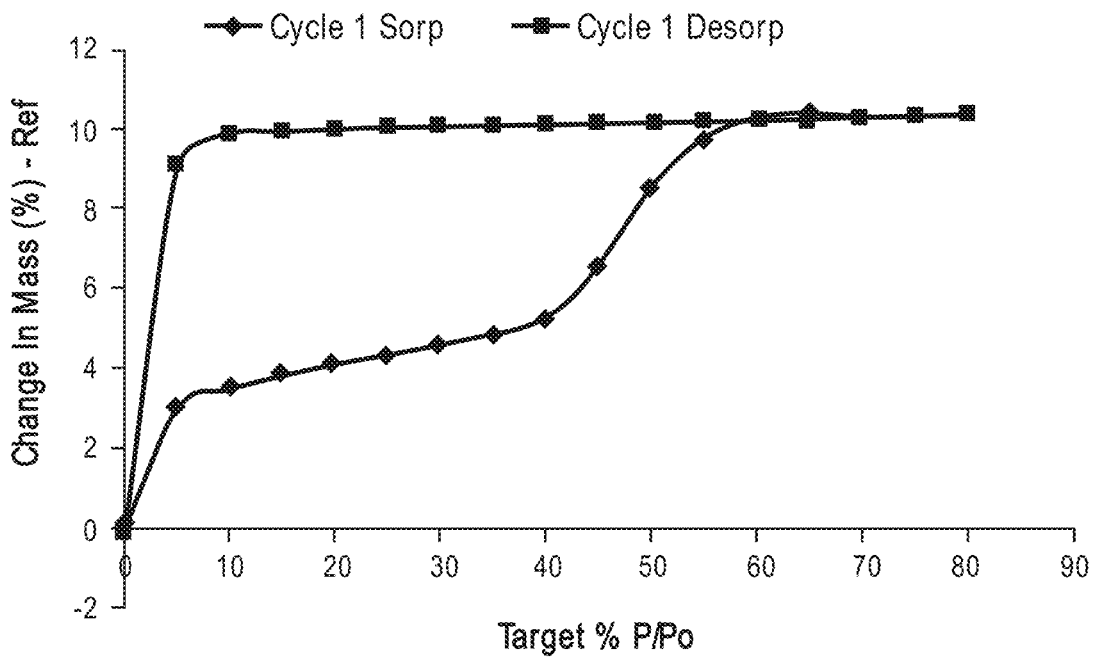
Figure 9D:
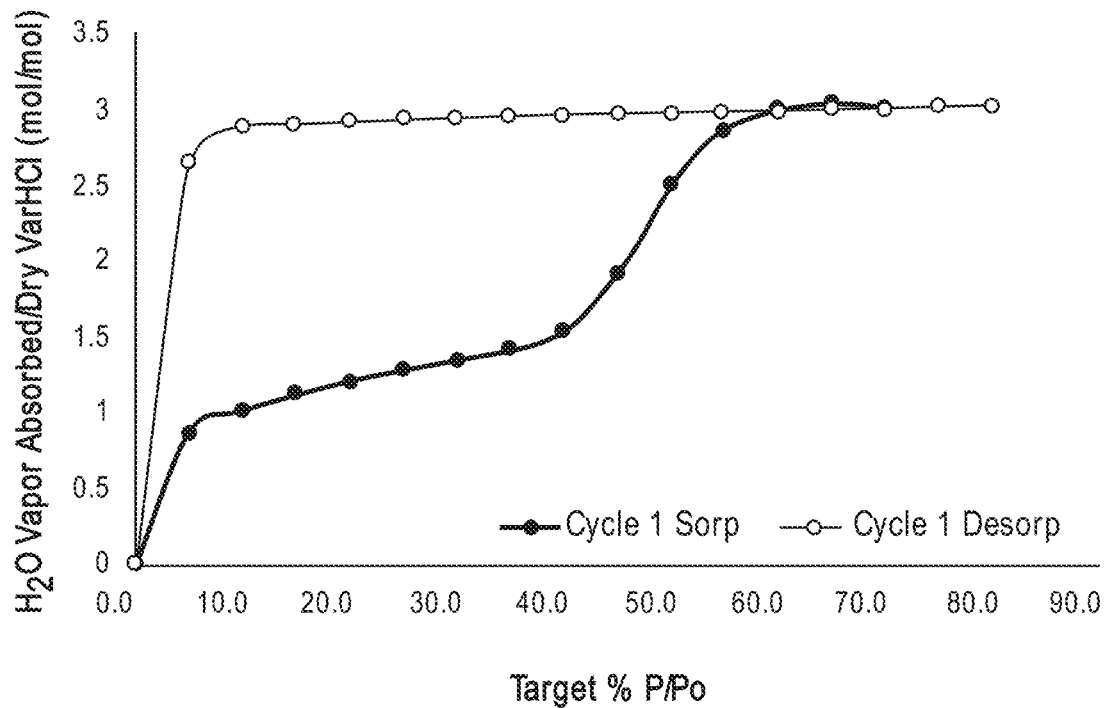

DVS of micronized $VarHCl \cdot xH_2O$ in FIG. 9C and FIG. 9D. In FIG. 9C, the Y-axis is % w/w $H_2O$ uptake, while in FIG. 9D the Y-axis is molar ratio. Together, these isotherm plots permit a clear understanding of stoichiometric water sorption and desorption of VarHCl.

In the VarHCl sorption phase, there were two inflection points. A first water molecule bound to anhydrous VarHCl at a relative humidity (RH) as low as 5% to form a monohydrate. This indicated that VarHCl is highly hygroscopic. Between RH 5-40%, a steady but slower water sorption occurred at increasing RH. This was followed by a more rapid water uptake between 40-60% RH. The sorption phase reached a plateau between 60-80% RH when the water content of the molecule reached the stoichiometric trihydrate form. This indicated that $VarHCl \cdot 3H_2O$ could maintain its integrity (not reaching deliquescence) up to 80% RH.

The quick water uptake at RH as low as 5% and preferential formation of monohydrate is presumably caused by different H-bond associations among the three water molecules that can bind to VarHCl. The first water molecule can preferentially form H-bonding with the acidic proton and the carbonyl group of vardenafil. This six-membered ring structure could result in stabilized H-bonding that the following $H_2O$ molecules may not have. See Scheme 1 below.

Scheme 1

In the VarHCl·3H$_2$O desorption phase, the trihydrate form was maintained between 10-80% RH. Water loss only occurred when RH is lower than 15%, and even more so 10%. These results indicated that VarHCl·3H$_2$O is a thermodynamically stable form and that, once the VarHCl·3H$_2$O is formed, it is unlikely to lose bound water in normal RH % when the powder is maintained at room temperature.

XRPD of micronized VarHCl·xH$_2$O is shown in FIG. 11C. The corresponding 2θ values of the major intensity peaks are: 5.1, 8.2, 10.3, 10.9, 15.4, 16.4, 17.3, 19.9, 20.2, 20.8, 22.4, 23.0, 24.5, 25.1, 26.1, 27.0, 27.9, 29.1 degree. The 2θ values of the intensity peaks for the micronized VarHCl·xH$_2$O were compared to previously reported values from the XRPD analysis of VarHCl·3H$_2$O (see, for example, U.S. Pat. No. 8,273,876). This comparison indicated that the micronized compound may lose some crystallinity due to the jet-milling process as the peaks are not as sharp (possibly due to loss of peak intensity due to the creation of amorphous content).

Example 6. Preparation of Vardenafil Formulations

Having established that lactose was a suitable excipient for vardenafil compound formulations, several lactose blends were prepared with various vardenafil compounds described in the previous examples. Mixing conditions were assessed to identify satisfactory blends.

The vardenafil compounds used were: Var(HCl)$_2$·xH$_2$O, VarBase, micronized VarHCl·xH$_2$O, and micronized VarHCl·3H$_2$O (rehydrated). Formulations were prepared using two different lactose carriers, a sieved grade of alpha-monohydrate lactose with an average particle size of about 50 μm (LAC1) and a fine particle lactose having a particle size distribution D$_{v50}$ below about 5 μm (LAC2).

To break up any large agglomerates and facilitate blending and blend homogeneity, the micronized APIs and LAC1 were passed through a 250 μm sieve. The API powders were then accurately weighed according to the API concentration using a micro balance. The pre-blend (1-5 g) was achieved by geometric dilution of API powder into LAC1. Trituration and gentle stirring with a spatula allowed for a good initial blending condition. The mixtures were then blended with a Turbula® T2C Shaker-Mixer. UV analysis was performed. The API was detected by UV spectrophotometry.

Various blending speeds were tested to determine what speed resulted in the best blending uniformity. The rotation speed of the shaker-mixer was calibrated using a stopwatch to slow (22 rpm), medium (49 rpm), and high (99 rpm) speeds. Blending was stopped at 5 min, 10 min, 15 min, and 20 min. At each time point, five accurately weighed samples (0.8-1 mg) from the top (2 samples), the bottom (2 samples) and the side (1 sample) of the jars were dissolved in 20 mL HPLC grade H$_2$O solution (H$_2$O: H$_3$PO$_4$=1L: 0.2 mL) and measured by UV spectrophotometry. The average concentration was analyzed and the relative standard deviation (% RSD) (also referred to as coefficient of variation (% CV) was used to evaluate the accuracy of blend concentration and blending uniformity, respectively. A % CV less than 5% was considered to be good blend uniformity.

Figure 12:
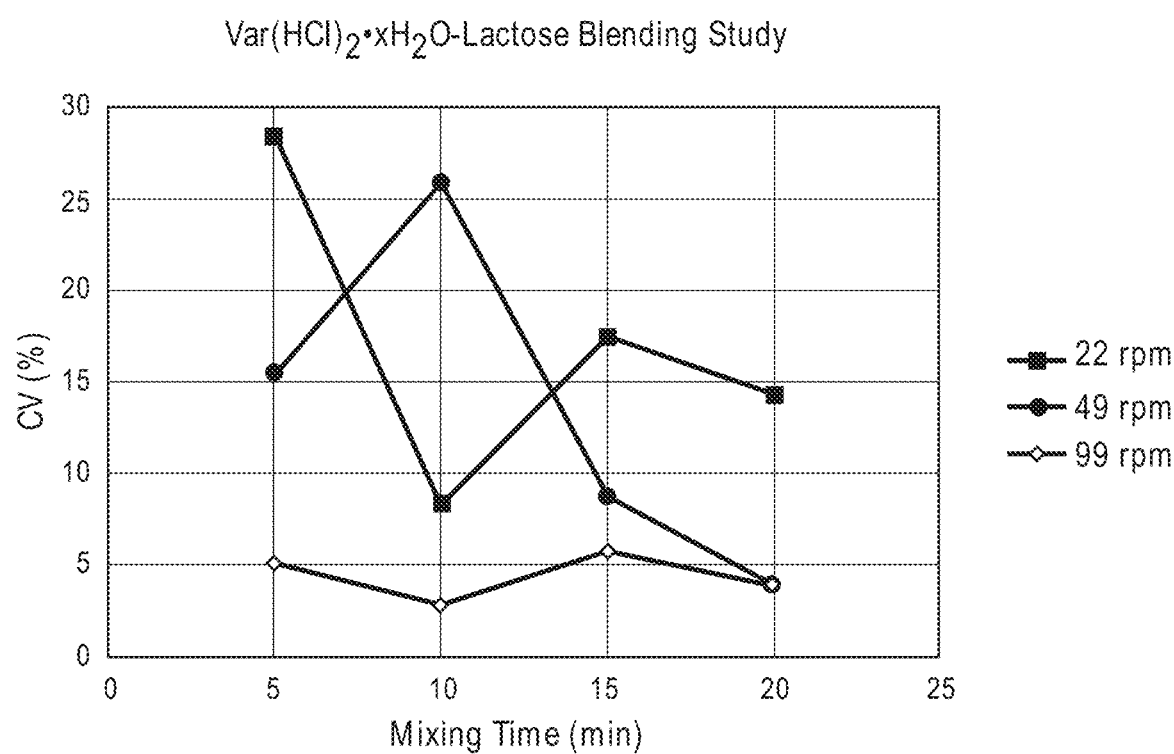
FIG. 12 and illustrates an exemplary conditions for preparation of a 5% Var(HCl)$_2$·xH$_2$O and lactose blend formulation. Components were hand blended and then mixed in a shaker-mixer at 22 rpm-, 49 rpm, and 99 rpm for 5 min, 10 min, 15 min, and 20 min. Extend of blend uniformity was assessed by the coefficient of variation (% CV) sampling.

An exemplary blending example using 5% Var(HCl)$_2$·xH$_2$O and LAC1 is shown in FIG. 12. Blending at high speed (99 rpm) gave the best blending uniformity. The % CV results were consistently within the range of 5% in 5-20 min. In contrast, blending at slow and medium speeds showed a pattern of mixing and de-mixing that is not suitable to reproducibly obtain a homogenous mixture.

Blending at high speed for 20 min generally resulted in an overall good blending uniformity for all API formulations. If UV analysis indicated that % CV was greater than 5% in any instances, formulations were mixed for an additional 10-20 min high speed to reduce the % CV to less than 5%.

Using the conditions outlined above, the formulation blends listed in Table 4 were prepared with satisfactory blend concentration and blend uniformity

TABLE 4

Formulation Blends

| | | |
|---|---|---|
| Var(HCl)$_2$•xH$_2$O + LAC1 | API Concentration: | 5% w/w |
| | | 13% w/w |
| | | 20% w/w |
| | | 40% w/w |
| | | 60% w/w |
| | | 80% w/w |
| Var(HCl)$_2$•xH$_2$O + LAC1 + LAC2 | Weight Ratio: | 20:77:3 |
| | | 20:20:60 |
| VarBase + LAC1 | API Concentration: | 5% w/w |
| | | 20% w/w |
| VarHCl•xH$_2$O + LAC1 (micronized API) | API Concentration: | 5% w/w |
| | | 20% w/w |
| VarHCl•3H$_2$O + LAC1 (micronized API) | API Concentration: | 20% w/w |

Example 7. Aerosol Performance of Vardenafil Formulations

One consideration when formulating a dry powder for inhalation is that its size should be small enough to permit aerosolization and the deposition at the appropriate site of the respiratory tract. A failure in deposition may result in a failure of efficacy.

There are several inertia sampling apparatuses that can be used to assess aerosol performance of dry powder formulations. (<601>Aerosols, Nasal Sprays, Metered-Dose Inhalers, and Dry Powder Inhalers Monograph, in USP 29-NF 24 The United States Pharmacopoeia and The National Formulary: The Official Compendia of Standards. 2006, The United States Pharmacopeial Convention, Inc.: Rockville, Md. p. 2617-2636 ("USP <601>").)

These apparatus classify aerosol particles on the basis of the particles' aerodynamic diameter. Each stage of the impactor includes a single or series of nozzles with specific cutoff size. Particles are entrained into the apparatus. Those having sufficient inertia will impact on that particular stage collection plate, while smaller particles with insufficient inertia will remain entrained in the airstream and pass to the next stage where the process is repeated. The aerodynamic size distribution of API can be assessed by collecting the deposited API mass and the ED %, RF %, FPF % and MMAD (μm) can be calculated from the API deposition pattern. The emitted dose fraction (ED(%); Eq. 4) is determined as the percentage powder mass emitted from the initial dosing chamber/capsule relative to the total dose in capsules (nominal dose) (TD). Emitted dose (ED) includes the sum of the API mass left on inhaler device and deposited on the device stages. Fine particle fraction (FPF(%); Eq. 5) is expressed as a percentage of fine particle dose (FPD) below a certain aerodynamic cutoff size to ED. Respirable fraction (RF(%); Eq. 6) is defined as the percentage of FPD to total dose (TD).

$$\text{Emitted dose fraction } (ED(\%)) = \left(\frac{ED}{TD}\right) \times 100\% \quad \text{(Eq. 4)}$$

$$\text{Fine particle fraction } (FPF(\%)) = \left(\frac{FPD}{ED}\right) \times 100\% \quad \text{(Eq. 5)}$$

$$\text{Respirable fraction } (RF(\%)) = \left(\frac{FPD}{TD}\right) \times 100\% \quad \text{(Eq. 6)}$$

A. Materials and Methods

Formulation aerosol performance tests were carried out using a powder deaggregator modified from that described in U.S. Patent Publication Nos. 2013/0340754 and 2013/0340747 combined with an off-the-shelf RS01 dry powder inhaler capsule piercing mechanism (Plastiape, IT) feeding method. The powder deaggregator had a 2.72 mm inlet diameter, a 10 mm oscillation chamber length, 5.89 mm oscillation chamber diameter, 4 mm polypropylene bead (density=0.90 mg/mm$^3$), 2 of 6 bypass channel open, and cross grid. With this capsule piercing mechanism, the delivery system had a resistance ($R_D$) of 0.104 (cmH$_2$O)$^{0.5}$/L/min. The experiments were conducted at an airflow rate that gave a system pressure drop of 2 kPa (about 40 L/min, 4 L inhalation volume duration: 5.5 sec) or 4 kPa (about 60 L/min, 4 L inhalation volume duration: 3.9 sec).

Formulations: Pure drug formulations (no excipient) of micronized VarBase, micronized VarHCl·xH$_2$O, micronized Var(HCl)$_2$·xH$_2$O (rehydrated), and micronized VarHCl·xH$_2$O were prepared as described in Examples 4 and 5. Vardenafil blends (5% API and 20% API) with LAC1 were prepared as described in Example 6 using micronized Var(HCl)$_2$·xH$_2$O, micronized VarBase, micronized VarHCl·xH$_2$O, and micronized VarHCl·3H$_2$O.

Packaging: The blends were packaged into size 3 HPMC capsules. Nominal dose amounts of 3 mg were prepared for each formulation; 10 mg nominal doses were also prepared for pure drug VarBase and Var(HCl)$_2$·xH$_2$O formulations.

Methods: Two inertial sampling systems were used to assess aerosol performance: (1) a Next Generation Impactor® ("NGI") (Copley Scientific, Shoreview, Minn.), and (2) a Twin Stage Liquid Impinge ("TSLI") (Copley Scientific, Shoreview, Minn.). Aerosol performance of the VarHCl·xH$_2$O formulation was assessed using the TSLI device, while the other formulations were all assessed using the NGI device. The NGI experiments were carried out using methods in general agreement with the USP <601>, and the TSLI experiments were carried using methods in general agreement with the British Pharmacopoeia, 2007, Vol. IV, Appendix XIIF. A291 Aerodynamic assessment of fine particles, fine particle dose and particle size distribution. The NGI experiments were run at a controlled airflow rate that gave a pressure drop of either 2 or 4 kPa across the device. Specifically, at Q=61.4 L/min with a delay time of 3.9 sec; and at Q=43.4 L/min with a delay time of 5.5 sec. Before the aerosol testing, the NGI collection plates were coated with suitable coating. Mass median aerodynamic diameter (MMAD) of aerosol particles distribution was determined based on a log-probability distribution (API particle size versus API deposition percentage) obtained from the NGI data. The TSLI experiments were run at Q=60 L/min, 4 sec to achieve ΔP≈4 kPa, with a cutoff size of 6.4 μm.

B. Pure Drug Formulations Aerosol Performance

Micronized pure drug formulations (100% API, no excipient) were found to generally have an emitted dose (ED) fraction in the range of 24-82% and an RF fraction in the range of 21-46%, as shown in Table 5. This was mainly due to poor powder flow with the delivery system described in Section A. However, the FPF(ED) was generally quite high, except for the 10 mg VarBase formulation. The micronized Var(HCl)$_2$·xH$_2$O resulted in the highest FPF(ED), followed by the VarHCl.xH$_2$O formulation, the VarHCl·3H$_2$O formulation, and the 3 mg VarBase formulation, each of which was well over 50%. Higher dose did not increase the aerosol performance but did negatively impact FPF(ED) for the VarBase formulation. Rehydration of Var(HCl)$_2$·xH$_2$O increased ED and RF markedly but decreased FPF(ED). The aerosol performance of the pure drug formulations is comparable to many currently marketed dry powder formulations. However, the way that the capsule piercing mechanism used in these experiments works results in a large amount of powder deposition within the mechanism itself, which reduces the ED %. Increasing the powder flow properties of the active agent, such as by adding a suitable dry powder base (carrier/diluent/excipient) may increase the ED % by facilitating powder fluidization during aerosolization. Thus, for use with the deaggregator-capsule piercing mechanism combination in these studies, improved aerosol performance may be obtained if the vardenafil compounds are blended with an excipient like lactose.

TABLE 5

Pure Drug Formulation Aerosol Performance

| Test | API | Dose (mg) | ED(%) | RF(%) | FPF(ED)(%) | % Recvy | MMAD (μm) |
|---|---|---|---|---|---|---|---|
| 1 | VarBase | 3 | 81.8 | 45.8 | 56.0 | — | 1.32 |
| 2 | VarBase | 10 | 64.2 | 23.9 | 37.2 | 115.2 | 1.51 |
| 3 | $Var(HCl)_2 \cdot xH_2O$ | 3 | 26.6 | 23.5 | 88.5 | — | 0.76 |
| 4 | $Var(HCl)_2 \cdot xH_2O$ | 10 | 24.5 | 21.2 | 86.5 | 114.0 | 0.82 |
| 5 | $Var(HCl)_2 \cdot xH_2O$ (rehydrated) | 3 | 71.4 | 45.4 | 63.6 | 100.1 | 1.37 |
| 6* | $VarHCl \cdot xH_2O$ | 3 | 40.7 | 28.1 | 68.9 | 112.0 | — |

*TSLI data cannot be used to determine MMAD.

C. API-Lactose Formulation Aerosol Performance

In a first experiment, aerosol performance of the 5% $Var(HCl)_2 \cdot xH_2O$ formulation was assessed. In addition to assessing impact of added lactose as an excipient, the impact of nominal load (or payload) on aerosol performance of this formulation was also assessed. Capsules were loaded with either 10 mg of formulation or 20 mg of formulation and assessed using the NGI device at 4 kPa airflow rate. The results are shown in Table 6 below (Mean±SD, n=3).

TABLE 6

5% Var(HCl)2•xH2O Formulation at 10 mg or 20 mg Nominal Load

| Nominal Load | ED (%) | RF (%) | FPF(ED) (%) | MMAD (μm) |
|---|---|---|---|---|
| 10 mg | 75.1 ± 4.2 | 51.1 ± 4.4 | 68.0 ± 2.9 | 0.81 ± 0.01 |
| 20 mg | 80.5 ± 1.4 | 53.0 ± 1.4 | 65.8 ± 0.7 | 0.84 ± 0.02 |

The ED and RF of the 5% $Var(HCl)_2 \cdot xH_2O$ formulation was found to be much higher than that of the pure drug $Var(HCl)_2 \cdot xH_2O$ formulation, though the FPF(ED) was reduced. The aerosol performance of the formulation was found to be independent of the nominal dose at 10 mg or 20 mg as the performance metrics [ED, RF, FPF(ED)] for each nominal dose were very similar. These results suggest that lactose-based formulations may improve aerosol performance of dry powder vardenafil formulations, at least when used with the delivery system described above in Example 7, Section A.

In a second study, the influence of API concentration on the aerosol performance of lactose-based $Var(HCl)_2 \cdot xH_2O$ formulations was evaluated. Capsules were loaded with 20 mg of either the 5% or 20% API formulation and assessed using the NGI device at 4 kPa airflow rate. The results are shown in Table 7 below (Mean±SD, n=3).

TABLE 7

5% + 20% Var(HCl)2•xH2O Formulation at 20 mg Nominal Load

| API conc (%) | ED (%) | RF (%) | FPF(ED) (%) | MMAD (μm) |
|---|---|---|---|---|
| 5 | 80.5 ± 1.4 | 53.0 ± 1.4 | 65.8 ± 0.7 | 0.84 ± 0.02 |
| 20 | 80.1 ± 7.8 | 60.8 ± 4.8 | 76.9 ± 1.4 | 0.92 ± 0.04 |

The results indicated that the RF can be improved by increasing the API concentration from 5% to 20% for this formulation. FPF(ED) also improved with increased concentration. These findings suggested that this delivery system may be particularly suitable for delivery of lactose-based formulation with high API concentration.

In order to evaluate if the other VarBase and $VarHCl \cdot xH_2O$ formulations have the same trend, a TSLI device experiment was designed to assess whether 20% API formulations for VarBase and $VarHCl \cdot xH_2O$ have better aerosol performance than 5% formulations when the deaggregator device-capsule piercing mechanism are used at 4 kPa airflow condition. For each active agent, the 20 mg payload of the 20% formulation includes 4 mg of the API, while the 5% formulation includes 1 g of the API. The results are shown in Table 8 below. The results for the 5% and 20% VarBase+LAC1 formulations are averaged data (Mean±SD, n=3).

TABLE 8

5% and 20% VarBase and VarHCl•xH2O Formulation at 60 L/min

| Test | Formulation | ED (%) | RF (%) | FPF(ED)(%) |
|---|---|---|---|---|
| 1 | 5% VarBase + LAC1 | 67.2 ± 3.9 | 26.6 ± 1.0 | 39.7 ± 0.9 |
| 2 | 20% VarBase + LAC1 | 76.4 ± 2.8 | 42.1 ± 2.7 | 55.0 ± 1.8 |
| 3 | 5% VarHCl•xH2O + LAC1 | 71.7 | 37.2 | 51.9 |
| 4 | 20% VarHCl•xH2O + LAC1 | 70.8 | 48.4 | 68.4 |

The results show that the 20% VarBase and $VarHCl \cdot xH_2O$ also have better aerosol performance than the corresponding 5% formulations. For the VarBase-LAC1 formulation, the increase of API concentration from 5% to 20% resulted in a RF increase from 26.6% to 42.1% and a FPF(ED) increase from 39.7% to 55%. For the $VarHCl \cdot xH_2O$-LAC1 formulation, the same trend held, with the RF increasing from 37.2% to 48.4% and the FPF(ED) increasing from 51.9% to 68.4%.

Example 8. Very High Dose Formulation Assessment of Aerosol Performance

As the 20% API-lactose blend formulations performed so well, an experiment was designed to assess the aerosol performance of very high concentration formulations. High concentration formulations may be desirable if ED is not reduced as a result. A Dose Unit Sampling Apparatus ("DUSA") (Copley Scientific, Shoreview, Minn.) was used to assess emitted dose of four $Var(HCl)_2 \cdot xH_2O$-LAC1 formulations were prepared as described in the preceding examples at an API concentration of 20%, 40%, 60%, and 80%. The DUSA experiments were carried out using methods in general agreement with the USP <601>. The same delivery device as described above in Example 7, Section A was used. As shown in FIG. 15A, a linear relationship ($R^2$=0.9718) was observed between ED and the API concentration of the formulation.

To investigate the reason for the observed decrease in emitted dose as seen in FIG. 15A, deposition of the API on the deaggregator and the capsule piercing mechanism were evaluated separately. These results show that the amount of the API that was retained in the device was mainly in the capsule piercing portion of the device, as the amount of deposition in this portion and the formulation concentration were positively correlated ($R^2$=0.9563; y=0.0052x+0.0873; $R^2$=0.9563) as shown in FIG. 15B. In contrast, the deposition of API on the deaggregator did not change as API concentration increased (data not shown). Thus, the 5-20% concentration range may result in about 80% ED for the Var(HCl)$_2$·xH$_2$O-LAC1 formulations when used with this delivery system at an airflow of 4 kPa. However, higher concentration formulations may be used with a different device capsule piercing mechanism that disperses the drug along the axis of the air flow and not toward the device internal walls like the capsule piercing mechanism used in these experiments. In such cases, it can be expected that less loss of drug to the internal surfaces will be achieved.

Example 9. Influence of Device Pressure Drop on Aerosol Performance

Having aerosol performance of a formulation be independent of airflow conditions is preferable because there is greater reproducibility in administration where airflow rate may be variable (for example, based on the user). The NGI device was used to assess the aerosol performance of the 20% Var(HCl)$_2$·xH2O+LAC1 formulation as described above in Example 7, Section A except at an airflow pressure of 4 kPa and 2 kPa (corresponding to about 60 and about 40 L/min airflow rate, respectively). Using the NGI stage cutoffs identified in the USP <601>, the aerosol performance data at the 2 kPa pressure drop was based on NGI cutoff stage 3 and below, and the aerosol performance data at the 4 kPa pressure drop was based on NGI cutoff stage 2 and below. The results are shown in Table 9 below (Mean±SD, n=3).

TABLE 9

20% Var(HCl)$_2$·xH$_2$O Formulation actuated at 2 kPa vs. 4 kPa

| Airflow | ED (%) | RF (%) | FPF(ED) (%) | MMAD (µm) |
|---|---|---|---|---|
| 2 kPa | 75.9 ± 7.5 | 51.6 ± 2.5 | 69.1 ± 2.2 | 1.15 ± 0.06 |
| 4 kPa | 80.1 ± 7.8 | 60.8 ± 4.8 | 76.9 ± 1.4 | 0.92 ± 0.04 |

The ED, RF, and FPF(ED) were decreased slightly at 2 kPa as compared to 4 kPa. However, the effective aerodynamic cutoff diameter ($D_{a50}$) for each impactor stage of the NGI device is different at different flow rates. At 4 kPa, the impactor stage cutoff is 4.41 µm (stage 2 and below). In contrast, at 2 kPa the impactor stage cutoff is 3.32 µm (stage 3 and below). As a result, at the faster airflow rate, larger size particles passed the cutoff and contributed to the aerosol performance. This suggests that the RF and FPF(ED) could be slightly underestimated at an airflow rate of 2 kPa. As such, the aerosol performance at 2 kPa did not appear to cause a substantial change in aerosol performance when compared at 4 kPa.

What is claimed is:

1. A powder pharmaceutical composition comprising:
 a) vardenafil hydrochloride as a PDE5 inhibitor,
 b) a first fraction of fine lactose particles, and
 c) a second fraction of lactose particles having an average diameter of about 5 µm to about 90 µm;
 wherein the PDE5 inhibitor is present in an amount of up to about 20% by weight relative to the total weight of the overall pharmaceutical composition; and
 wherein the first fraction of fine lactose particles is present in an amount of up to about 10% by weight relative to the total weight of the lactose in the composition.

2. The powder pharmaceutical composition of claim 1, wherein the composition comprises at least about 2% by weight of the PDE5 inhibitor.

3. The powder pharmaceutical composition of claim 1, wherein the fine lactose particles have an average diameter of less than about 7 µm.

4. The powder pharmaceutical composition of claim 3, wherein the second fraction of lactose particles has an average diameter about 50 µm to about 90 µm.

5. The powder pharmaceutical composition of claim 1, wherein the PDE5 inhibitor or salt or ester thereof is present as micronized particles.

6. The powder pharmaceutical composition of claim 5, wherein the $D_{V50}$ of the micronized particles is up to about 2 µm.

7. The powder pharmaceutical composition of claim 6, wherein the $D_{V50}$ of the micronized particles is between about 1 µm and about 2 µm.

8. The powder pharmaceutical composition of claim 1, further comprising calcium stearate, magnesium stearate, leucine, leucine derivatives, lecithin, human serum albumin, polylysine, polyarginine, or other force control agents, or combinations thereof.

9. The powder pharmaceutical composition of claim 1, wherein the composition is packaged to have a nominal load of about 3 mg to 30 mg.

10. The powder pharmaceutical composition of claim 1, wherein the composition is packaged to have a nominal dose of at least about 0.25 mg.

11. The powder pharmaceutical composition of claim 1, wherein the composition is packaged to have a delivered dose of at least about 0.075 mg.

* * * * *